(12) United States Patent
Collingwood et al.

(10) Patent No.: US 12,415,793 B2
(45) Date of Patent: Sep. 16, 2025

(54) MODULATORS OF TMEM16A FOR TREATING RESPIRATORY DISEASE

(71) Applicant: TMEM16A Limited, Welwyn Garden City (GB)

(72) Inventors: Stephen Collingwood, Brighton (GB); Jonathan David Hargrave, Abingdon (GB); Duncan Alexander Hay, Abingdon (GB); Edward Walker, Abingdon (GB)

(73) Assignee: TMEM16A Limited, Welwyn Garden City (GB)

( * ) Notice: Subject to any disclaimer, the term of this patent is extended or adjusted under 35 U.S.C. 154(b) by 885 days.

(21) Appl. No.: 17/547,967

(22) Filed: Dec. 10, 2021

(65) Prior Publication Data

US 2022/0098164 A1  Mar. 31, 2022

Related U.S. Application Data

(63) Continuation of application No. PCT/GB2020/051414, filed on Jun. 12, 2020.

(51) Int. Cl.

| C07D 333/38 | (2006.01) |
|---|---|
| A61K 31/166 | (2006.01) |
| A61K 31/167 | (2006.01) |
| A61K 31/381 | (2006.01) |
| A61K 31/44 | (2006.01) |
| A61P 11/00 | (2006.01) |
| C07C 233/07 | (2006.01) |
| C07D 213/127 | (2006.01) |
| C07D 213/56 | (2006.01) |
| C07D 213/72 | (2006.01) |
| C07D 213/81 | (2006.01) |
| C07D 213/82 | (2006.01) |
| C07D 333/36 | (2006.01) |

(52) U.S. Cl.
CPC .......... C07D 333/36 (2013.01); C07C 233/07 (2013.01); C07D 213/127 (2013.01); C07D 213/56 (2013.01); C07D 213/72 (2013.01)

(58) Field of Classification Search
CPC  C07D 333/38; C07D 213/127; C07D 213/56; C07D 213/72; C07D 213/81; C07D 213/82; C07D 237/42; A61K 31/166; A61K 31/44; A61K 31/167; A61K 31/381
See application file for complete search history.

(56) References Cited

U.S. PATENT DOCUMENTS

| 4,746,653 A | 5/1988 | Hutchison et al. |
|---|---|---|
| 2002/0151555 A1 | 10/2002 | Barvian et al. |
| 2003/0229103 A1 | 12/2003 | Welthmann et al. |
| 2005/0004111 A1 | 1/2005 | Klingler et al. |
| 2006/0173183 A1 | 8/2006 | Powers et al. |
| 2007/0155739 A1 | 7/2007 | Sucholeiki et al. |
| 2011/0269834 A1 | 11/2011 | Ghosh et al. |
| 2013/0303511 A1 | 11/2013 | Clark et al. |
| 2016/0152579 A1 | 6/2016 | Pérez Fernández et al. |

FOREIGN PATENT DOCUMENTS

| CN | 104672241 A | 6/2015 |
|---|---|---|
| CN | 107954977 A | 4/2018 |
| CN | 111683926 A | 9/2020 |
| DE | 10160357 A1 | 6/2003 |
| DE | 10251019 A1 | 5/2004 |
| DE | 10300017 A1 | 7/2004 |
| EP | 1291345 A1 | 3/2003 |
| EP | 2558085 A2 | 2/2013 |
| EP | 2558086 A1 | 2/2013 |
| JP | 2005513049 A | 5/2005 |
| WO | 9706138 A1 | 2/1997 |
| WO | 9926476 A1 | 6/1999 |
| WO | 02064568 A1 | 8/2002 |
| WO | 03014094 A2 | 2/2003 |
| WO | 2004060883 A1 | 7/2004 |
| WO | 2008009735 A1 | 1/2008 |
| WO | 2011129936 A2 | 10/2011 |
| WO | 2012053186 A1 | 4/2012 |
| WO | 2012142513 A1 | 10/2012 |
| WO | 2014062204 A1 | 4/2014 |
| WO | 2014195857 A1 | 12/2014 |
| WO | 2017075394 A1 | 5/2017 |
| WO | 2018200833 A1 | 11/2018 |
| WO | 2019079609 A1 | 4/2019 |
| WO | 2019145726 A1 | 8/2019 |
| WO | 2020249956 A1 | 12/2020 |

OTHER PUBLICATIONS

International Search Report and Written Opinion issued in International Application No. PCT/GB2020/051414, mailed on Jul. 29, 2020, 27 pages.

Augustin et al. (Nov. 1974) "Umsetzungen Von N-substituierten Maleinimiden Mit Thioharnstoffen Und Polarographische Untersuchung Des Reaktionsablaufs", Zeitschrift für Chemie, 14(11):434-435.

Balasubramaniyan et al. (1986) "Reactions of O-Aminothiophenol with Aβ-Unsaturated Dicarbonyl Systems. Facile Synthesis of Benzothiazines and Benzothiazepines", Tetrahedron, 42(10):2731-2738.

(Continued)

*Primary Examiner* — Bruck Kifle
(74) *Attorney, Agent, or Firm* — Robert C. Hall

(57) ABSTRACT

Compounds of general formula (I):

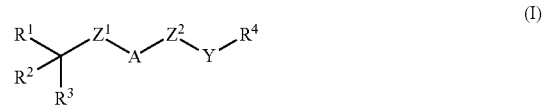

wherein $R^1$, $R^2$, $R^3$, $R^4$, A, $Z^1$, $Z^2$ and Y are as defined herein are useful for treating respiratory disease and other diseases and conditions modulated by TMEM16A.

13 Claims, 1 Drawing Sheet

(56) References Cited

OTHER PUBLICATIONS

Duro-Castano et al. (2018) "In Vivo Imaging of MMP-13 Activity Using a Specific Polymer-FRET Peptide Conjugate Detects Early Osteoarthritis and Inhibitor Efficacy", Advanced Functional Materials, 28(37):1802738.
Hodgkinson et al. (Jan. 1, 2012) "Design, Synthesis and Biological Evaluation of Non-Natural Modulators of Quorum Sensing In Pseudomonas Aeruginosa", Organic & Biomolecular Chemistry, 10(30):6032-6044.
Hugenberg et al. (2017) "Radiolabeled Selective Matrix Metalloproteinase 13 (MMP-13) Inhibitors: (Radio) Syntheses and in Vitro and First in Vivo Evaluation", Journal of Medicinal Chemistry, 60(1):307-321.
Jung et al. (2006) "Discovery of Novel and Potent Thiazoloquinazolines as Selective Aurora A and B Kinase Inhibitors", Journal of Medicinal Chemistry, 49(3):955-970.
Ramana et al. (Mar. 1, 1975) "Electron-Impact-Induced Hydrogen Migration in Organic Molecules I-Substituent Effects in the Mass Spectra of Pivlanilides", Organic Mass Spectrometry. 10(3):196-199.
Suarez-Pantaleon et al. (Jan. 1, 2011) "Forchlorfenuron-Mimicking Haptens: From Immunogen Design To Antibody Characterization by Hierarchical Clustering Analysis", Organic & Biomolecular Chemistry, 9(13):4863-4872.
Truong et al. (Jun. 8, 2017) "Substituted 2-Acylaminocycloalkylthiophene-3-Carboxylic Acid Arylamides as Inhibitors of the Calcium-Activated Chloride Channel Transmembrane Protein 16A (TMEM16A)", Journal of Medicinal Chemistry. 60(11):4626-4635.
Tyagi et al. (2012) "Iron(III) Complexes of Bis (Benzimidazol-2-yl) Methyl) Thiophene-2,5-Dicarboxamide: Synthesis, Spectral and Oxidation of O-Phenylenediamine", Spectrochimica Acta Part A Molecular and Biomolecular Spectroscopy, 96:759-767.
Yamagami et al. (1984) "Hydrophobic Properties of Anticonvulsant Phenylacetanilides. Relationship Between Octanol-Water Partition Coefficient and Capacity Factor Determined by Reversed-Phase Liquid Chromatography". Chemical And Pharmaceutical Bulletin, 32(12):4994-5002.
Yue et al. (2006) "Ring-Opening Polymerization of Coordination Complexes: Silver(I) Complexes with Bis (Amidopyridine) Ligands Derived from Thiophene", Dalton Transactions, (32):3886-3893.
Zhou et al. (Sep. 2018) "Rhodium(III)-Catalyzed C-H Vinylation of Arenes: Access to Functionalized Styrenes : Rhodium(III)-Catalyzed C—H Vinylation of Arenes: Access to Functionalized Styrenes", Chinese Journal of Chemistry, 36:1143-1146.
Accurso et al., Denufosol Tetrasodium in Patients with Cystic Fibrosis and Normal to Mildly Impaired Lung Function. Am J Respir Crit Care Med, 2011, vol. 183, pp. 627-634.
Boucher, R.C., Evidence for airway surface dehydration as the initiating event in CF airway disease, Journal of Internal Medicine, 2007, vol. 261, pp. 5-16.
Caputo et al., TMEM16A, A Membrane Protein Associated with Calcium-Dependent Chloride Channel Activity, Science, Oct. 24, 2008, vol. 322, pp. 590-594.
De La Fuente et al., Small-Molecule Screen Identifies Inhibitors of a Human Intestinal Calcium-Activated Chloride Channel, Molecular Pharmacology, 2008, vol. 73, No. 3, pp. 758-768.
Kellerman et al., Denufosol: A review of studies with inhaled P2Y2 agonists that led to Phase 3, Pulmonary Pharmacology & Therapeutics, 2008, vol. 21, pp. 600-607, Abstract.
Kunzelmann et al., Pharmacotherapy of the Ion Transport Defect in Cystic Fibrosis: Role of Purinergic Receptor Agonists and Other Potential Therapeutics, Am J Respir Med, 2003, vol. 2, No. 4, pp. 299-309.
Matsui et al., Evidence for Periciliary Liquid Layer Depletion, Not Abnormal Ion Composition, in the Pathogenesis of Cystic Fibrosis Airways Disease, Cell, Dec. 23, 1998, vol. 95, No. 7, pp. 1005-1015.
Moss, Richard B., Pitfalls of Drug Development: Lessons Learned from Trials of Denufosol in Cystic Fibrosis, The Journal of Pediatrics, 2013, vol. 162, No. 4, pp. 676-680.
Pedemonte et al., Structure and Function of TMEM16 Proteins (Anoctamins), Physiol Rev, 2014, vol. 94, pp. 419-459.
Pezzulo et al., Reduced airway surface pH impairs bacterial killing in the porcine cystic fibrosis lung, Nature, 2012, vol. 487, pp. 109-113.
Yang et al., TMEM16A confers receptor-activated calcium-dependent chloride conductance, Nature, 2008, vol. 455, pp. 1210-1215.
Database STN, Registry No. 1976179-02-8, entered Aug. 21, 2016.
Database STN, Registry No. 1960669-78-6, entered Jul. 27, 2016.
Database STN, Registry No. 1946505-08-3, entered Jul. 6, 2016.
Database STN, Registry No. 1919488-36-0, entered May 27, 2016.
Database STN, Registry No. 1912396-88-3, entered May 17, 2016.
Database STN, Registry No. 1877743-79-7, entered Mar. 2, 2016.
Database STN, Registry No. 1797767-52-2, entered Jul. 9, 2015.
Database STN, Registry No. 1777337-09-3, entered Jun. 10, 2015.
Database STN, Registry No. 1647877-05-1, entered Feb. 15, 2015.
Database STN, Registry No. 339226-31-2, entered Jun. 3, 2001.
Database STN, Registry No. 326181-74-2, entered Mar. 7, 2001.

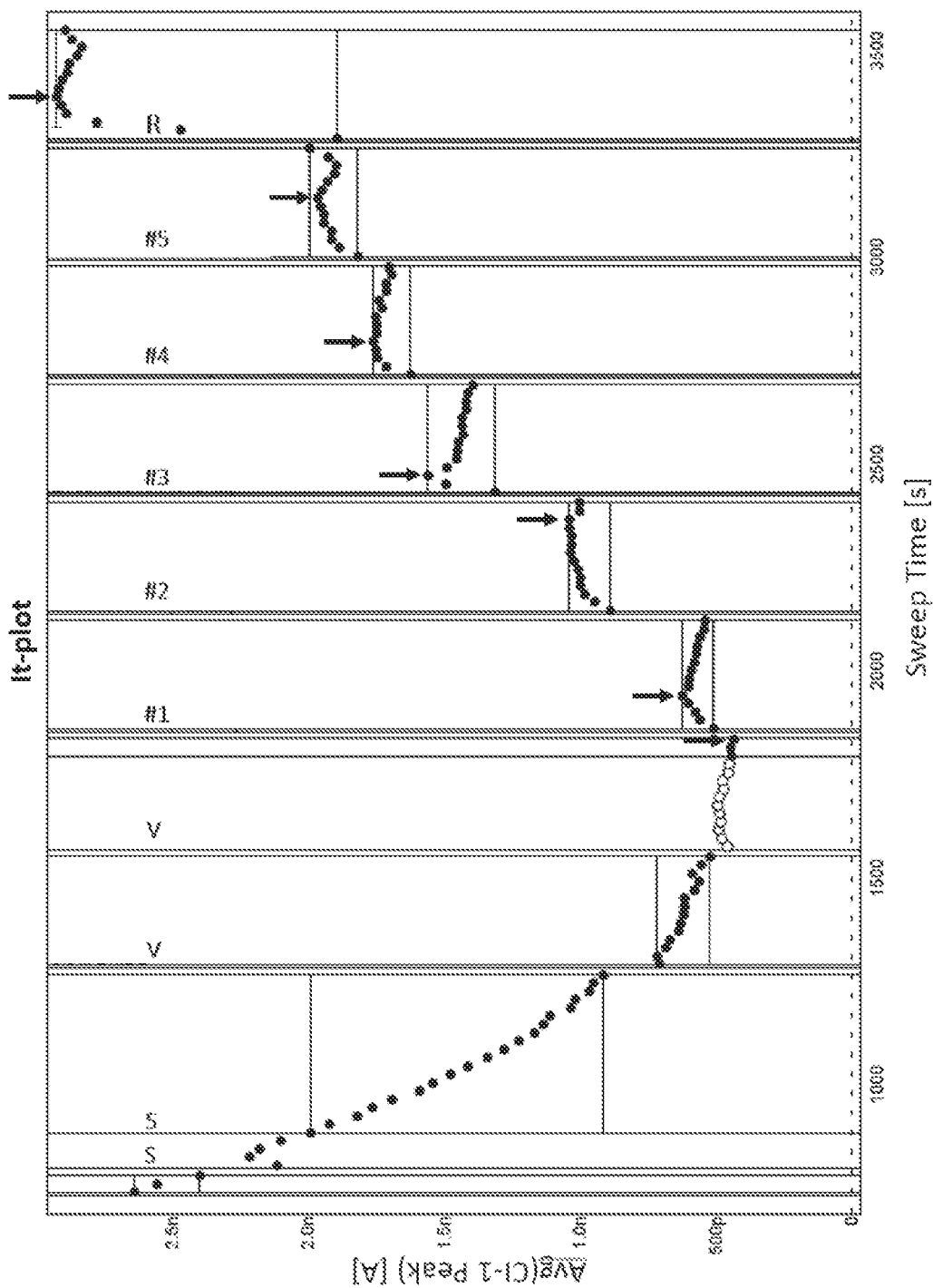

MODULATORS OF TMEM16A FOR TREATING RESPIRATORY DISEASE

This application is a continuation of the International Application No. PCT/GB2020/051414, filed Jun. 12, 2020, which claims the benefit of GB Application No. 1908453.2, filed Jun. 12, 2019, which are incorporated hereby by reference in their entirety for all purposes.

The present invention relates to novel compounds which have activity as positive modulators of the calcium-activated chloride channel (CaCC), TMEM16A. The invention also relates to methods of preparing the compounds and pharmaceutical compositions containing them as well as to the use of these compounds in treating diseases and conditions modulated by TMEM16A, particularly respiratory diseases and conditions.

Humans can inhale up to 12,000 L of air each day and with it comes the potential for airborne pathogens (such as bacteria, viruses and fungal spores) to enter the airways. To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% w/v solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Strategies to increase the hydration of the airway mucus include either the stimulation of anion and thereby fluid secretion or the inhibition of $Na^+$ absorption. To this end, stimulating the activity of TMEM16A channels will increase anion secretion and therefore increase fluid accumulation in the airway mucosa, hydrate mucus and enhance mucus clearance mechanisms.

TMEM16A, also referred to as Anoctamin-1 (Ano1), is the molecular identity of calcium-activated chloride channels (Caputo et al, 2008; Yang et al, 2008). TMEM16A channels open in response to elevation of intracellular calcium levels and allow the bidirectional flux of chloride, bicarbonate and other anions across the cell membrane. Functionally TMEM16A channels have been proposed to modulate transepithelial ion transport, gastrointestinal peristalsis, nociception and cell migration/proliferation (Pedemonte & Galietta, 2014).

TMEM16A channels are expressed by the epithelial cells of different organs including the lungs, liver, kidney, pancreas and salivary glands. In the airway epithelium TMEM16A is expressed at high levels in mucus producing goblet cells, ciliated cells and in submucosal glands. Physiologically TMEM16A is activated by stimuli which mobilise intracellular calcium, particularly purinergic agonists (ATP, UTP), which are released by the respiratory epithelium in response to cyclical shear stress caused by breathing and other mechanical stimuli such as cough. In addition to increasing anion secretion leading to enhanced hydration of the airways, activation of TMEM16A plays an important role in bicarbonate secretion. Bicarbonate secretion is reported to be an important regulator of mucus properties and in controlling airway lumen pH and hence the activity of native antimicrobials such as defensins (Pezzulo et al, 2012).

Indirect modulation of TMEM16A, via elevation of intracellular calcium, has been clinically explored e.g. denufosol (Kunzelmann & Mall, 2003). Although encouraging initial results were observed in small patient cohorts this approach did not deliver clinical benefit in larger patient cohorts (Accurso et al 2011; Kellerman et al 2008). This lack of clinical effect was ascribed to only a transient elevation in anion secretion, the result of a short half-life of denufosol on the surface of the epithelium and receptor/pathway desensitisation, and unwanted effects of elevating intracellular calcium such as increased release of mucus from goblet cells (Moss, 2013). Compounds which act directly upon TMEM16A to enhance channel opening at low levels of calcium elevation are expected to durably enhance anion secretion and mucociliary clearance in patients and improve innate defence. As TMEM16A activity is independent of CFTR function, TMEM16A positive modulators have the potential to deliver clinical benefit to all CF patients and non-CF respiratory diseases characterised by mucus congestion including chronic bronchitis and severe asthma.

TMEM16A modulation has been implicated as a therapy for dry mouth (xerostomia), resultant from salivary gland dysfunction in Sjorgen's syndrome and radiation therapy, dry eye, cholestasis and gastrointestinal motility disorders.

Our application, PCT/GB2019/050209 relates to compounds which are positive modulators of TMEM16A and which are therefore of use in the treatment of diseases and conditions in which modulation of TMEM16A plays a role, particularly respiratory diseases and conditions. The present inventors have developed further compounds which are positive modulators of TMEM16A.

In a first aspect of the present invention there is provided a compound of general formula (I) including all tautomeric forms all enantiomers and isotopic variants and salts and solvates thereof:

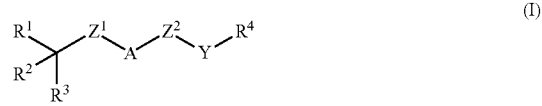

wherein
A is

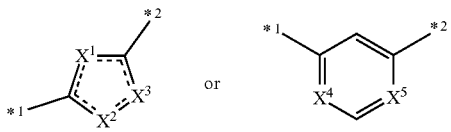

where
one of $X^1$, $X^2$, $X^3$ is S and the other two of $X^1$, $X^2$ and $X^3$ are CH;
=== represents a single or a double bond such that the ring A is aromatic; each of $X^4$ and $X^5$ is independently CH or N;
*¹ indicates the point of attachment to $Z^1$ and *² indicates the point of attachment to $Z^2$; each of $Z^1$ and $Z^2$ is independently selected from *—C(O)NH— and *—NHC(O)—, where * indicates the point of attachment to the ring A;
$R^1$ is H, CN, C(O)OR$^{12}$, $C_{1-3}$ alkyl, $C_{2-3}$ alkenyl or $C_{2-3}$ alkynyl, any of which alkyl, alkenyl or alkynyl groups are optionally substituted with one or more substituents, suitably one substituent, selected from fluoro, OR$^{12}$, N(R$^{12}$)$_2$, C(O)OR$^{12}$, C(O)N(R$^{12}$)$_2$, C(O)R$^{12}$ and N(R$^{13}$)C(O)R$^{12}$;
wherein each $R^{12}$ and $R^{13}$ is independently selected from H, $C_{1-6}$ alkyl and $C_{1-6}$ fluoroalkyl;
$R^2$ is H or $C_{1-6}$ alkyl optionally substituted with OR$^{12}$; and $R^3$ is:
$C_{1-6}$ alkyl, $C_{2-6}$ alkenyl or $C_{2-6}$ alkynyl, any of which $C_{1-6}$ alkyl, $C_{2-6}$ alkenyl or $C_{2-6}$ alkynyl groups are optionally substituted with one or more substituents selected from fluoro, CN, R$^{14}$ OR$^{14}$, OR$^{15}$, N(R$^{15}$)$_2$, C(O)OR$^{15}$, C(O)N(R$^{15}$)$_2$, N(R$^{16}$)C(O)R$^{15}$, N(R$^{15}$)S(O)$_2$R$^{14}$, N(R$^{15}$)S(O)$_2$R$^{16}$ and N(R$^{15}$)C(O)OR$^{16}$; or
$R^3$ is:
a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, OR$^{17}$ and N(R$^{17}$)$_2$;
wherein $R^{14}$ is a 6- to 10-membered aryl or 5- to 10-membered heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OR$^{17}$ and N(R$^{17}$)$_2$; wherein each $R^{17}$ is independently H, $C_{1-4}$ alkyl or $C_{1-4}$ haloalkyl; each $R^{15}$ and $R^{16}$ is independently H, $C_{1-6}$ alkyl or $C_{1-6}$ haloalkyl; or
$R^2$ and $R^3$ together with the carbon atom to which they are attached combine to form a 3- to 10-membered carbocyclic or heterocyclic ring system optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$; or
$R^1$, $R^2$ and $R^3$ together with the carbon atom to which they are attached combine to form a bridged 5- to 10-membered carbocyclic or heterocyclic ring system or phenyl, any of which carbocyclic or heterocyclic ring systems or phenyl groups are optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$;
each $R^9$ is independently selected from H, $C_{1-6}$ alkyl or $C_{1-6}$ haloalkyl;
Y is —CH$_2$— or —CH(CH$_3$)—;
$R^4$ is a 6- to 14-membered aryl, 5- to 14-membered heteroaryl or a 5- to 10-membered carbocyclic ring system, any of which is optionally substituted with one or more substituents selected from:
halo, CN, nitro, R$^{19}$, OR$^{19}$, OR$^6$, SR$^6$, NR$^6$R$^7$, C(O)R$^6$, C(O)R$^{19}$, C(O)OR$^6$, C(O)N(R$^6$)(R$^7$), N(R$^7$)C(O)R$^6$;
$C_{1-6}$ alkyl or O($C_{1-6}$ alkyl) either of which is optionally substituted with one or more substituents selected from halo, CN, nitro, R$^{19}$, OR$^6$, SR$^6$, NR$^6$R$^7$, C(O)R$^6$C(O) OR$^6$, C(O)N(R$^6$)(R$^7$) and N(R$^7$)C(O)R$^6$; and
when $R^4$ is not fully aromatic in character, oxo;
wherein $R^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, O($C_{1-4}$ alkyl), O($C_{1-4}$ haloalkyl);
$R^6$ is H, $C_{1-6}$ alkyl, $C_{1-6}$ haloalkyl, benzyl, 3- to 7-membered carbocyclyl or 3- to 7-membered heterocyclyl;
$R^7$ is H, $C_{1-6}$ alkyl or $C_{1-6}$ haloalkyl; or
$R^6$ and $R^7$ together with the nitrogen atom to which they are attached form a 4 to 7-membered heterocyclic ring optionally containing one or more further heteroatoms and optionally substituted with one or more substituents selected from $C_{1-4}$ alkyl, oxo and halo;
provided that:
i. when A is

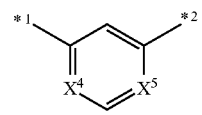

and $Z^1$ is *—C(O)NH—,
$Z^2$ is not *—NHC(O)—; and
ii. when A is

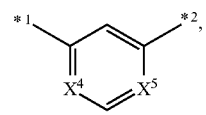

$Z^1$ is *—NHC(O)—, $Z^2$ is *—C(O)NH—; and
$R^1$ and $R^2$ are H and $R^3$ is a carbocyclic, heterocyclic, aryl or heteroaryl ring system optionally substituted as defined above; or
$R^1$ is H and $R^2$ and $R^3$ combine to form a carbocyclic or heterocyclic ring system optionally substituted as defined above; or
$R^1$, $R^2$ and $R^3$ together with the carbon atom to which they are attached combine to form a bridged 5- to 10-membered carbocyclic or heterocyclic ring system or phenyl optionally substituted as defined above; then R⁴ is not a 6- to 14-membered aryl group optionally substituted as defined above.

Throughout the specification and the claims which follow, unless the context requires otherwise, the word "comprise", and variations such as "comprises" and "comprising", will be understood to imply the inclusion of a stated integer, step, group of integers or group of steps but not to the exclusion of any other integer, step, group of integers or group of steps.

All literature and patent documents referred to herein are incorporated by reference to the fullest extent possible.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-10}$ alkyl are as defined above but contain different numbers of carbon atoms.

The term "$C_{2-6}$" alkenyl refers to a straight or branched hydrocarbon group having from 1 to 6 carbon atoms and at least one carbon-carbon double bond. The term encompasses ethenyl, propen-1-yl, propen-2-yl, buten-1-yl and buten-2-yl. Other alkenyl groups, for example $C_{2-10}$ alkenyl are as defined above but contain different numbers of carbon atoms.

The term "$C_{2-6}$" alkynyl refers to a straight or branched hydrocarbon group having from 1 to 6 carbon atoms and at least one carbon-carbon triple bond. The term encompasses ethynyl, propyn-1-yl, propyn-2-yl, butyn-1-yl and butyn-2-yl. Other alkynyl groups, for example $C_{2-10}$ alkynyl are as defined above but contain different numbers of carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged, where carbon atoms in a bridge are included in the number of ring carbon atoms. Examples include cyclopropyl, cyclobutyl, cyclopentyl, cyclohexyl, cyclopentenyl and cyclohexenyl as well as bridged systems such as bicyclo[1.1.1]pentyl, bicyclo-[2.2.1]heptyl, bicyclo-[2.2.2]octyl and adamantyl.

In the context of the present specification, the terms "heterocyclic" and "heterocyclyl" refer to a non-aromatic ring system containing 3 to 10 ring atoms, unless otherwise indicated, including at least one heteroatom selected from N, O and S. The heterocyclic group may be a single ring or may contain two or three rings which may be fused or bridged, where bridge atoms are included in the number of ring atoms. Examples include tetrahydrofuranyl, tetrahydropyranyl, pyrrolidinyl, piperidinyl, morpholinyl, piperazinyl and thiomorpholinyl, as well as fused systems such as cyclopropyl-f used pyrrolidine.

The terms "aryl" and "aromatic" in the context of the present specification refer to a ring system with aromatic character having from 5 to 14 ring carbon atoms, unless otherwise indicated, and containing up to three rings. Where an aryl group contains more than one ring, not all rings must be fully aromatic in character. Examples of aromatic moieties are benzene, naphthalene, fluorene, tetrahydronaphthalene, indane and indene.

The terms "heteroaryl" and "heteroaromatic" in the context of the specification refer to a ring system with aromatic character having from 5 to 14 ring atoms, unless otherwise indicated, at least one of which is a heteroatom selected from N, O and S, and containing up to three rings. Where a heteroaryl group contains more than one ring, not all rings must be aromatic in character. Examples of heteroaryl groups include pyridine, pyrimidine, indole, indazole, thiophene, benzothiophene, benzoxazole, benzofuran, dihydrobenzofuran, tetrahydrobenzofuran, benzimidazole, benzimidazoline, quinoline and indolene.

The term "oxo" refers to a C=O substituent, where the carbon atom is a ring atom of a carbocyclyl, heterocyclyl group or a ring of an aryl or heteroaryl group which is not aromatic in character.

The term "halogen" refers to fluorine, chlorine, bromine or iodine and the term "halo" to fluoro, chloro, bromo or iodo groups. Similarly, "halide" refers to fluoride, chloride, bromide or iodide.

The term "$C_{1-6}$ haloalkyl" as used herein refers to a $C_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. A fluoroalkyl group is a haloalkyl group in which halo is fluoro.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

In some compounds of general formula (I), A is:

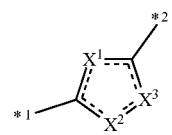

In this case, the compound of general formula (I) may be a compound of general formula (Ia), (Ib) or (Ic):

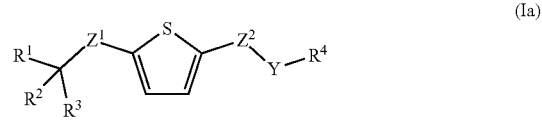

(Ia)

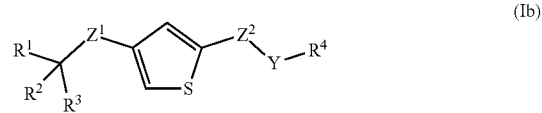

(Ib)

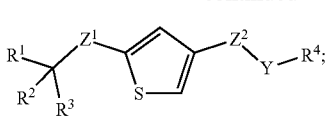 (Ic)

wherein $R^1$, $R^2$, $R^3$, $R^4$, $Z^1$, $Z^2$ and Y are as defined for general formula (I).

In some cases, the compound of general formula (I) is a compound of general formula (Ia).

In some cases, the compound of general formula (I) is a compound of general formula (Ib).

In some cases, the compound of general formula (I) is a compound of general formula (Ic).

Alternatively, A is:

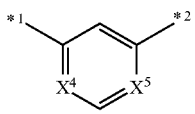

In this case, the compound of general formula (I) may be a compound of general formula (Id), (Ie), (If) or (Ig):

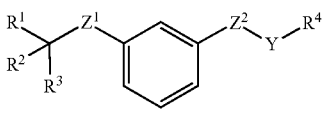 (Id)

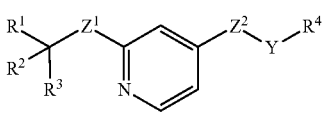 (Ie)

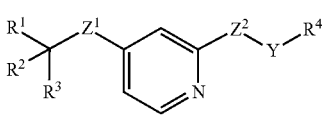 (If)

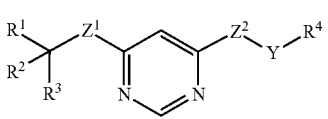 (Ig)

wherein $R^1$, $R^2$, $R^3$, $R^4$, $Z^1$, $Z^2$ and Y are as defined for general formula (I).

In some cases, the compound of general formula (I) is a compound of general formula (Id).

In some cases, the compound of general formula (I) is a compound of general formula (Ie).

In some cases, the compound of general formula (I) is a compound of general formula (If).

In some cases, the compound of general formula (I) is a compound of general formula (Ig).

In some compounds of (Id), (Ie), (If) and (Ig) neither $R^1$ nor $R^2$ is H.

In some compounds of (Id), (Ie), (If) and (Ig), $R^1$, $R^2$ and $R^3$ do not combine to form phenyl.

In some compounds of (Id), (Ie), (If) and (Ig), when $R^1$ is H and $R^2$ and $R^3$ together with the carbon atom to which they are attached combine to form a 3- to 10-membered carbocyclic or heterocyclic ring system optionally substituted as described above, $R^4$ is phenyl substituted with OH and halo. More suitably, $R^4$ is 2-hydroxy-5-halophenyl, for example 2-hydroxy-5-chlorophenyl.

In some compounds of (Id), (Ie), (If) and (Ig), when $Z^1$ is *—NHC(O)— and $Z^2$ is *—C(O)NH—, neither $R^1$ nor $R^2$ is H.

In some compounds of (Id), (Ie), (If) and (Ig), when $Z^1$ is *—NHC(O)— and $Z^2$ is *—C(O)NH—, $R^1$, $R^2$ and $R^3$ do not combine to form phenyl.

In some compounds of (Id), (Ie), (If) and (Ig), when $R^1$ is H and $R^2$ and $R^3$ together with the carbon atom to which they are attached combine to form a 3- to 10-membered carbocyclic or heterocyclic ring system optionally substituted as described above, $Z^1$ is *—NHC(O)— and $Z^2$ is *—C(O)NH—, $R^4$ is phenyl substituted with OH and halo. More suitably, $R^4$ is 2-hydroxy-5-halophenyl, for example 2-hydroxy-5-chlorophenyl.

In the compounds of general formula (I), Y is suitably —$CH_2$—.

In more suitable compounds of general formula (I) $R^1$ is H, CN, $C(O)OR^{12}$, $C_{1-3}$ alkyl, $C_{2-3}$ alkenyl or $C_{2-3}$ alkynyl, any of which alkyl, alkenyl or alkynyl groups are optionally substituted with one or more substituents selected from fluoro and $OR^{12}$;
  wherein each $R^{12}$ is as defined above but is more suitably H, $C_{1-3}$ alkyl or $C_{1-3}$ fluoroalkyl, for example H, methyl or trifluoromethyl.

More suitably when $R^1$ is an alkyl, alkenyl or alkynyl group, it is optionally substituted with one or more halo substituent and/or a single $OR^{12}$ substituent.

More suitably, $R^1$ is H, CN or $C_{1-3}$ alkyl, $C_{2-3}$ alkenyl or $C_{2-3}$ alkynyl, any of which is unsubstituted or substituted as defined above.

In still more suitable compounds, $R^1$ is H, CN or $C_{1-3}$ alkyl optionally substituted as described above, more especially CN, unsubstituted $C_{1-3}$ alkyl such as methyl or $C_{1-3}$ haloalkyl such as trifluoromethyl.

In some suitable compounds $R^2$ is H or $C_{1-3}$ alkyl optionally substituted with $OR^{12}$, wherein each $R^{12}$ is as defined above but is more suitably H, $C_{1-3}$ alkyl or $C_{1-3}$ fluoroalkyl and especially $C_{1-3}$ alkyl or $C_{1-3}$ fluoroalkyl, for example methyl or trifluoromethyl.

More suitably, $R^2$ is H or unsubstituted $C_{1-3}$ alkyl, especially unsubstituted $C_{1-3}$ alkyl such as methyl.

In some suitable compounds of the invention, $R^3$ is $C_{1-6}$ alkyl, $C_{2-6}$ alkenyl or $C_{2-6}$ alkynyl, any of which is optionally substituted with one or more substituents, suitably one substituent, selected from fluoro, CN, $R^{14}$ $OR^{14}$, $OR^{15}$, $N(R^{15})_2$, $C(O)OR^{15}$, $C(O)N(R^{15})_2$, $N(R^{16})C(O)R^{15}$, $N(R^{15})S(O)_2R^{14}$, $N(R^{15})S(O)_2R^{16}$ and $N(R^{15})C(O)OR^{16}$;
  wherein each $R^{15}$ and $R^{16}$ is independently as defined above but is especially H, $C_{1-3}$ alkyl or $C_{1-3}$ haloalkyl, for example H, methyl or trifluoromethyl.

More suitably, $R^3$ is $C_{1-3}$ alkyl, $C_{2-3}$ alkenyl or $C_{2-3}$ alkynyl, any of which is optionally substituted as described above. In particularly suitable compounds of the invention, $R^3$ is $C_{1-3}$ alkyl, optionally substituted as described above, especially unsubstituted $C_{1-3}$ alkyl such as methyl.

Alternatively, $R^2$ and $R^3$ together with the carbon atom to which they are attached may combine to form a 3- to 10-membered carbocyclic or heterocyclic ring system which is unsubstituted or is substituted as defined above. More suitable substituents for such ring systems include with one or more substituents selected from halo, CN, $OR^9$, $N(R^9)_2$ and $C_{1-4}$ alkyl optionally substituted with halo, $OR^9$ or $N(R^9)_2$; wherein $R^9$ is as defined above but is more suitably H, $C_{1-3}$ alkyl or $C_{1-3}$ haloalkyl, particularly H, methyl or trifluoromethyl.

Particularly suitable substituents for ring systems formed by $R^2$ and $R^3$ include halo, OH, methoxy, trifluoromethoxy, methyl and trifluoromethyl.

Suitable heterocyclic rings formed by $R^2$ and $R^3$ include; tetrahydropyran-yl, for example tetrahydropyran-4-yl; tetrahydrofuranyl, for example tetrahydrofuran-3-yl; oxetanyl, for example oxetan-3-yl; piperidinyl, for example piperidin-2-yl and piperidin-4-yl; morpholinyl, piperazinyl and cyclopropyl-f used pyrrolidine.

More suitably, the ring formed by $R^2$ and $R^3$ is a carbocyclic ring. Examples of such carbocyclic rings include: cyclopropyl, cyclobutyl, cyclopentyl, cyclohexyl; and bridged systems such as bicyclo[1.1.1]pentyl, bicyclo-[2.2.1]heptyl, bicyclo-[2.2.2]octyl and adamantyl, (provided that the atom to which $R^2$ and $R^3$ are attached is not a bridge atom).

More suitable carbocyclic rings formed by $R^2$ and $R^3$ include cyclopropyl, cyclobutyl, cyclopentyl and cyclohexyl.

In still other suitable compounds of the present invention, $R^1$, $R^2$ and $R^3$ combine with the carbon atom to which they are attached to form a bridged carbocyclic or heterocyclic ring system, especially a carbocyclic system such as bicyclo[1.1.1]pentanyl, bicyclo[2.1.1]hexanyl, bicyclo-[2.2.1]heptanyl, bicyclo-[2.2.2]octanyl or adamantyl.

In some cases, the carbocyclic system may be selected from 3-bicyclo[1.1.1]pentanyl, bicyclo-[2.2.1]heptanyl, bicyclo-[2.2.2]octanyl and 1-adamantyl.

In other cases, the carbocyclic ring system may be selected from bicyclo[1.1.1]pentanyl, bicyclo[2.1.1]hexanyl and adamantyl, especially, 3-bicyclo[1.1.1]pentanyl, 1-bicyclo[2.1.1]hexanyl and 1-adamantyl, Suitably, the ring system is unsubstituted or substituted with a single substituent selected from $OR^9$ and $C(O)OR^9$, where $R^9$ is as defined above but is suitably H, methyl or ethyl, especially H or methyl and more particularly methyl. More suitably, the ring system is unsubstituted.

In some particularly suitable compounds of the invention, each of $R^1$, $R^2$ and $R^3$ is $C_{1-3}$ alkyl which is unsubstituted or is substituted as described above. More particularly, each of $R^1$, $R^2$ and $R^3$ is unsubstituted $C_{1-3}$ alkyl, for example methyl.

In other particularly suitable compounds of the invention, $R^1$ is cyano and each of $R^2$ and $R^3$ is $C_{1-3}$ alkyl which is unsubstituted or is substituted as described above. More particularly, each of $R^2$ and $R^3$ is unsubstituted $C_{1-3}$ alkyl, for example methyl.

In other particularly suitable compounds of the invention, $R^1$ is H or $CF_3$ and $R^2$ and $R^3$ together with the carbon atom to which they are attached form a 3- to 10-membered carbocyclic or heterocyclic ring system which is unsubstituted or is substituted as defined above. More especially, $R^1$ is H or $CF_3$ and $R^2$ and $R^3$ together with the carbon atom to which they are attached form a 3- to 10-membered carbocyclic ring system, especially a cyclopropyl, cyclobutyl, cyclopentyl or cyclohexyl ring.

In the compounds of the present invention $R^4$ is a 6-14-membered aryl, 5-14-membered heteroaryl or a 5- to 10-membered carbocyclic ring system, any of which is unsubstituted or substituted as defined above. More suitably, $R^4$ is 6-10-membered aryl, 5- to 10-membered heteroaryl or a 5- to 10-membered carbocyclic or heterocyclic ring system, any of which is optionally substituted with one or more substituents as described above.

In some more suitable compounds of general formula (I), $R^4$ is a 6- to 11-membered aryl group, for example a group selected from phenyl, naphthyl, indanyl, 1,2,3,4-tetrahydronaphthyl and benzocycloheptanyl, any of which is unsubstituted or is substituted as described above.

In other more suitable compounds of general formula (I), $R^4$ is a 5- to 10-membered heteroaryl group, for example a group selected from pyridyl, quinolinyl, quinoxalinyl, indazolyl, indolyl, benzoxazolyl, dihydrobenzofuranyl, furyl and thienyl, any of which is unsubstituted or substituted as described above.

In other more suitable compounds of general formula (I), $R^4$ is a carbocyclyl group, for example a group selected from cyclohexyl and adamantyl, any of which is unsubstituted or substituted as described above.

In some suitable compounds of the present invention, $R^4$ is phenyl optionally substituted with one or more substituents as described above.

Alternatively, $R^4$ is 5-10-membered heteroaryl optionally substituted with one or more substituents as described above. More suitably in this case $R^4$ is pyridyl, pyrrolyl, thienyl, furyl, benzoxazolyl, imidazolyl, indolyl or indazolyl.

In some suitable compounds, $R^4$ is substituted with one or more substituents selected from:
halo, CN;
$OR^6$, $NR^6R^7$, $C(O)OR^6$, $C(O)N(R^6)(R^7)$;
$C_{1-6}$ alkyl optionally substituted with one or more substituents selected from halo, CN, $OR^6$,
$NR^6R^7$, $C(O)OR^6$ and $C(O)N(R^6)(R^7)$;
wherein $R^6$ is H, $C_{1-6}$ alkyl, $C_{1-6}$ haloalkyl, 3-7 membered carbocyclyl or 3-7 membered heterocyclyl;
$R^7$ is H, $C_{1-6}$ alkyl or $C_{1-6}$ haloalkyl; or
$R^6$ and $R^7$ together with the nitrogen atom to which they are attached may form a 5- or 6-membered heterocyclic ring optionally containing one or more further heteroatoms and optionally substituted with one or more oxo substituents.

In other suitable compounds, wherein $R^4$ is an aryl group, it is more suitably unsubstituted or substituted with one or more substituents selected from:
halo, CN, $R^{19}$, $OR^{19}$;
$OR^6$, $C(O)OR^6$;
$C_{1-4}$ alkyl or $O(C_{1-4}$ alkyl) optionally substituted with one or more substituents selected from halo, CN, $R^{19}$, $OR^{19}$, $OR^6$ and $NR^6R^7$;
wherein $R^6$, $R^7$ and $R^{19}$ are as defined above.

More suitably, however, $R^6$ is H, $C_{1-4}$ alkyl or $C_{1-4}$ haloalkyl or, for a moiety $NR^6R^7$, $R^6$ and $R^7$ combine with the nitrogen atom to which they are attached to form a 5- or 6-membered heterocyclic ring, optionally containing one or more further heteroatoms and optionally substituted with one or more halo substituents.

$R^{19}$ is more suitably a 3- to 6-membered carbocyclyl group or phenyl, either or which is optionally substituted with one or more substituents selected from halo, methyl and methoxy.

In particularly suitable compounds, $R^4$ is phenyl substituted with an OH group at either the 2- or the 3-position and optionally with one or more further substituents as defined for general formula (I), more suitably with one or more further substituents, for example one or two further substituents, selected from those defined immediately above. Suitably, when further substituents are present, one of the further substituents is halo, for example chloro or fluoro. The halo substituent is suitably positioned in the para orientation with respect to the OH group. If a third substituent is present, this is most suitably $C_{1-4}$ alkyl which is unsubstituted or substituted as defined above, most suitably unsubstituted or substituted with an OH group.

When $R^4$ is a bicyclic aryl group it is more suitably unsubstituted or substituted with one or two substituents selected from OH and halo.

When $R^4$ is a heteroaryl group, it is more suitably unsubstituted or substituted with one or more substituents selected from OH and halo.

When $R^4$ is a carbocyclic group it is more suitably unsubstituted or substituted with one or more substituents selected from OH and halo. Still more suitably, it is unsubstituted.

In particularly suitable compounds of the present invention, Y is —$CH_2$—, $R^4$ is phenyl and the compound is a compound of general formula (Ii):

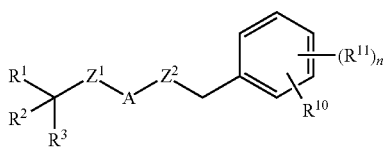
(Ii)

wherein
$R^1$, $R^2$, $R^3$, A, $Z^1$ and $Z^2$ are as defined for general formula (I);
$R^{10}$ is H, OH, halo, $C_{1-6}$ alkyl, —O($C_{1-6}$ alkyl);
each $R^{11}$ is independently H, halo, OH, CN, $C_{1-6}$ alkyl, $C_{1-6}$ haloalkyl, —O($C_{1-6}$ alkyl) or C(O)O—($C_{1-6}$ alkyl); and
n is 1 or 2.

Still more suitably, the compound is a compound of general formula (Iii) or (Iiii):

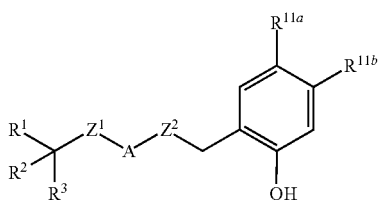
(Iii)

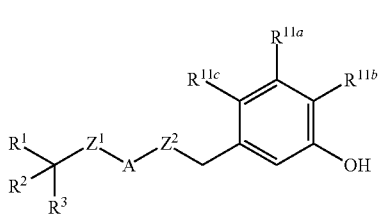
(Iiii)

wherein
$R^1$, $R^2$, $R^3$, A, $Z^1$ and $Z^2$ are as defined for general formula (I);
$R^{11a}$ is H, halo, $C_{1-4}$ alkyl, $C_{1-4}$ haloalkyl or C(O)O($C_{1-4}$ alkyl);
$R^{11b}$ is H, halo, $C_{1-4}$ alkyl or $C_{1-4}$ haloalkyl; and
$R^{11c}$ is H, halo, CN, $C_{1-4}$ alkyl or $C_{1-4}$ haloalkyl.

In compounds of general formula (Ii) where A is:

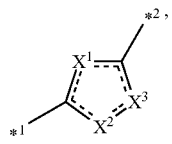

the compound of general formula (Ii) may be a compound of general formula (Iai), (Ibi) or (Ici):

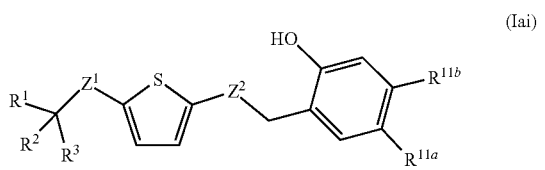
(Iai)

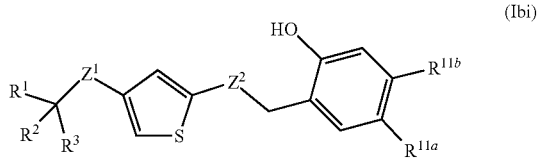
(Ibi)

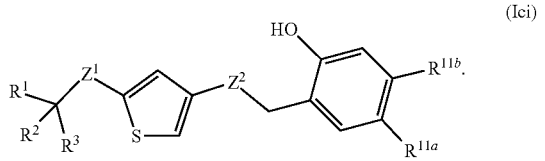
(Ici)

In cases where A is:

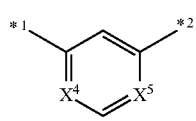

the compound of general formula (Ii) may be a compound of general formula (Idi), (Iei), (Ifi) or (Iqi):

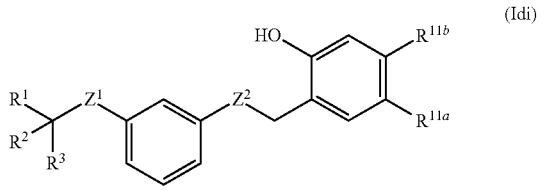
(Idi)

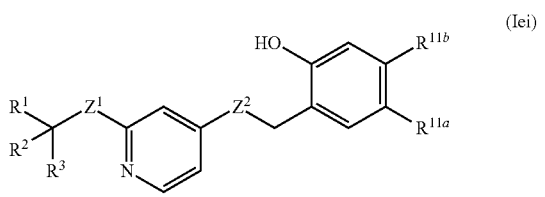
(Iei)

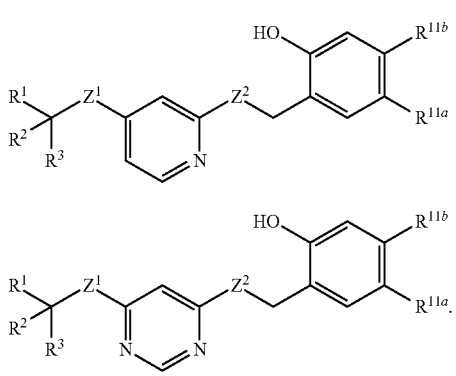

In particularly suitable compounds of general formulae (Ii), (Iai), (Ibi), (Ici), (Idi), (Iei), (Ifi) and (Igi), one or both of $R^{11a}$ and $R^{11b}$ is H.

In some such compounds, $R^{11a}$ is H, halo, $C_{1-4}$ alkyl or $C(O)O(C_{1-4}$ alkyl) and $R^{11b}$ is H.

More suitably, $R^{11a}$ is H, chloro, $C_{1-4}$ alkyl or $C(O)OCH_3$ and $R^{11b}$ is H.

In some compounds of general formulae (Ii), (Iai), (Ibi), (Ici), (Idi), (Iei), (Ifi) and (Igi), $R^{11a}$ is chloro and $R^{11b}$ is H.

In other such compounds of general formulae (Ii), (Iai), (Ibi), (Ici), (Idi), (Iei), (Ifi) and (Igi), $R^{11a}$ is H and $R^{11b}$ is H, halo or $C_{1-6}$ haloalkyl.

More suitably, $R^{11a}$ is H and $R^{11b}$ is H, chloro, bromo or trifluoromethyl.

Alternatively, in other particularly suitable compounds of general formulae (Ii), (Iai), (Ibi), (Ici), (Idi), (Iei), (Ifi) and (Igi), both $R^{11a}$ and $R^{11b}$ are halo, particularly chloro or bromo.

In compounds of general formula (Iii) where A is:

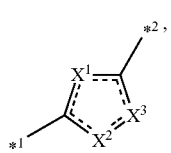

the compound of general formula (Iii) may be a compound of general formula (Iaii), (Ibii) or (Icii):

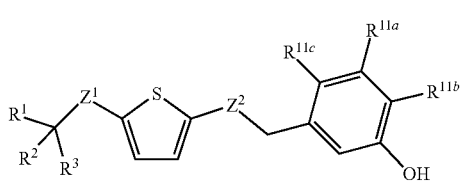

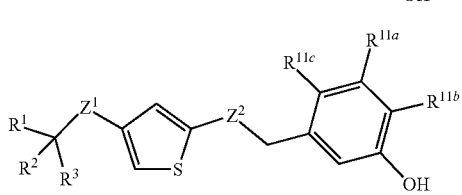

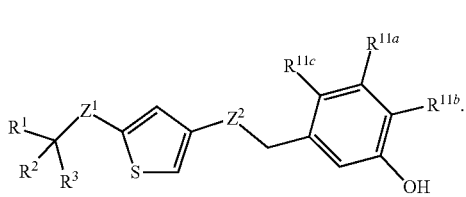

In cases where A is:

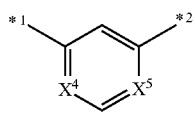

the compound of general formula (Iii) may be a compound of general formula (Idii), (Ieii), (Ifii) or (Igii):

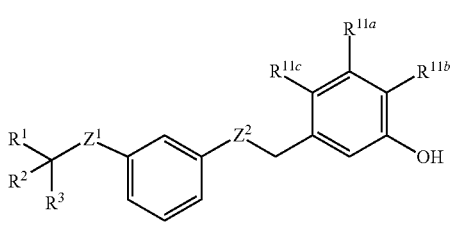

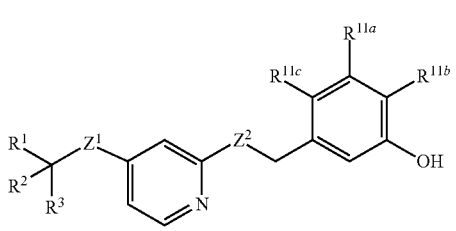

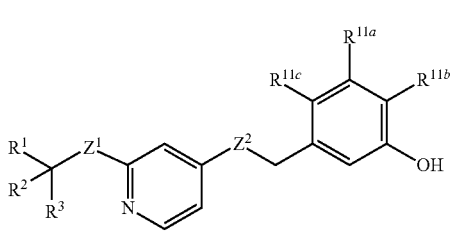

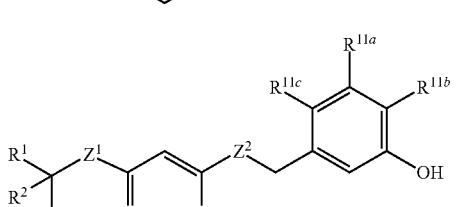

In some suitable compounds of general formulae (Iii), (Iaii), (Ibii), (Icii), (Idii), (Ieii), (Ifii) and (Igii), $R^{11a}$ is H, $R^{11b}$ is $C_{1-4}$ alkyl, $C_{1-4}$ alkyl substituted with OH or $C_{1-4}$ haloalkyl, and $R^{11c}$ is H, halo, methyl or ethyl.

In more suitable compounds of general formulae (Iii), (Iaii), (Ibii), (Icii), (Idii), (Ieii), (Ifii) and (Igii), $R^{11a}$ is H, $R^{11b}$ is $C_{1-4}$ alkyl, $C_{1-4}$ alkyl substituted with OH or $C_{1-4}$ halo alkyl, for example t-butyl, or 2-hydroxy-1,1-dimethylethyl, and $R^{11c}$ is chloro of fluoro.

Specific examples of compounds of general formula (I) include the following:
N-tert-Butyl-5-[[2-(5-chloro-2-hydroxy-phenyl)acetyl] amino]thiophene-2-carboxamide (Compound 1);
N-tert-Butyl-5-[[2-(5-chloro-2-hydroxy-phenyl)acetyl] amino]thiophene-3-carboxamide (Compound 1.2);
N-tert-Butyl-4-[[2-(5-chloro-2-hydroxy-phenyl)acetyl] amino]thiophene-2-carboxamide (Compound 1.3);
N-[(5-Chloro-2-hydroxy-phenyl)methyl]-3-(2,2-dimethyl-propanoylamino)benzamide (Compound 2);
N-[(5-Chloro-2-hydroxy-phenyl)methyl]-4-(2,2-dimethyl-propanoylamino)pyridine-2-carboxamide (Compound 3);
N2-tert-Butyl-N4-[(2-hydroxyphenyl)methyl]pyridine-2,4-dicarboxamide (Compound 4);
N1-tert-Butyl-N3-[(2-hydroxyphenyl)methyl]benzene-1,3-dicarboxamide (Compound 5);
N-[3-[[2-(5-Chloro-2-hydroxy-phenyl)acetyl]amino]phenyl]-2,2-dimethyl-propanamide (Compound 6);
N-[4-[[2-(5-Chloro-2-hydroxy-phenyl)acetyl]amino]-2-pyridyl]-2,2-dimethyl-propanamide (Compound 7);
N-[4-[[2-(5-Chloro-2-hydroxy-phenyl)acetyl]amino]-2-pyridyl]cyclohexane carboxamide (Compound 7.1);
5-[[2-(4-tert-Butyl-2-fluoro-5-hydroxy-phenyl)acetyl] amino]-N-(1-cyano-1-methyl-ethyl)thiophene-2-carboxamide (Compound 8);
5-[[2-[2-Fluoro-5-hydroxy-4-(2-hydroxy-1,1-dimethyl-ethyl)phenyl]acetyl]amino]-N-[1-(trifluoromethyl)cyclo-propyl]thiophene-2-carboxamide (Compound 9); and salts and solvates of the above.

A compound of general formula (I) in which $Z^1$ is *—C (O)NH—, $Z^2$ is *—NHC(O)— and A is:

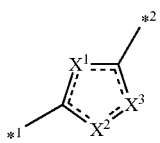

may be prepared by reacting a compound of general formula (II):

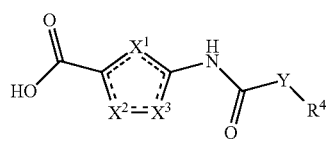

(II)

wherein $X^1$, $X^2$, $X^3$, Y and $R^4$ are as defined for general formula (I);
with a compound of general formula (III):

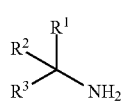

(III)

wherein $R^1$, $R^2$ and $R^3$ are as defined in general formula (I).

Suitably, the reaction is conducted in the presence of a coupling reagent and under basic conditions, for example in the presence of an amine such as diisopropylethylamine (DIPEA) and in an organic solvent such as DMF.

Suitable coupling reagents include known peptide coupling agents such as O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP) carbodiimides such as 1-ethyl-3-(3-dimethylaminopropyl)carbodiimide (EDCI) and triazoles such as 1-hydroxy-7-azabenzotriazole (HOAt) or hydroxybenzotriazole (HOBt). Suitably, the reaction is conducted under basic conditions, for example in the presence of an amine such as diisopropylethylamine (DIPEA) and in an organic solvent such as DMF.

Alternatively, the coupling reagent may be propylphosphonic anhydride (T3P®). When T3P is used as the coupling reagent, the reaction may be conducted under basic conditions, for example in the presence of an amine such as diisopropylethylamine (DIPEA) or triethylamine (TEA) and in an organic solvent such as dioxane.

Compounds of general formula (III) are readily available or may be synthesised by known methods.

The compound of general formula (II) may be prepared by the hydrolysis of a compound of general formula (IV):

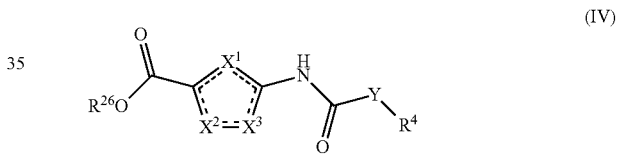

(IV)

wherein $X^1$, $X^2$, $X^3$, Y and $R^4$ are as defined for general formula (I) and $R^{26}$ is $C_{1-6}$ alkyl or benzyl.

Suitably, the hydrolysis is carried out under basic conditions, for example using a metal hydroxide such as lithium hydroxide, sodium hydroxide or potassium hydroxide in an aqueous organic solvent.

A compound of general formula (IV) may be prepared by reacting a compound of general formula (V):

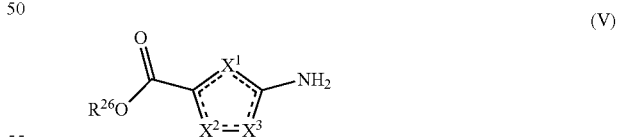

(V)

wherein $X^1$, $X^2$ and $X^3$ are as defined for general formula (I) and $R^{26}$ is as defined for general formula (IV);
with a carboxylic acid of general formula (VI):

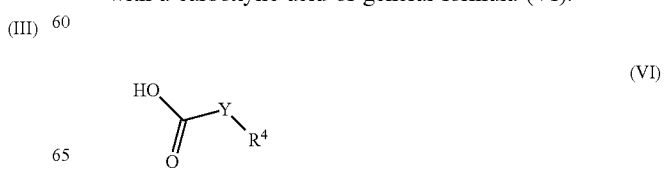

(VI)

wherein Y and R$^4$ are as defined for general formula (I);
or
an acid halide of general formula (VII):

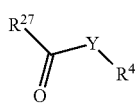

(VII)

wherein Y and R$^4$ are as defined for general formula (I) and R$^{27}$ is a halide for example chloride or bromide.

When the compound of general formula (V) is reacted with the carboxylic acid of general formula (VI), the reaction is suitably carried out in the presence of a coupling agent under basic conditions, for example in the presence of an amine such as diisopropylethylamine (DIPEA) and in an organic solvent such as DMF. Suitable coupling agents are as described above.

When the compound of general formula (V) is reacted with an acid halide of general formula (VII), the reaction is suitably carried out under basic conditions, for example in the presence of an amine such as diisopropylethylamine (DIPEA) and in an organic solvent such as dichloromethane.

Compounds of general formulae (V) and (VI) are readily available or can be prepared by known methods. Compounds of general formula (VII) can be prepared by known methods from compounds of general formula (VI). For example, an acid chloride of general formula (VII) may be obtained by treating the corresponding acid of general formula (VI) with thionyl chloride, suitably at elevated temperature, for example about 60 to 80° C., typically about 70° C.

A compound of general formula (I) in which Z$^1$ is *—NHC(O)— and Z$^2$ is *—C(O)NH— may be prepared by reacting a compound of general formula (X):

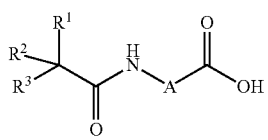

(X)

wherein R$^1$, R$^2$, R$^3$ and A are as defined for general formula (I);
with a compound of general formula (XI):

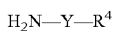

(XI)

wherein Y and R$^4$ are as defined for general formula (I).

Suitably, the reaction is carried out using a coupling agent such as T3P® under basic conditions, for example in the presence of an amine such as diisopropylethylamine (DIPEA) or triethylamine (TEA) and in an organic solvent such as dioxane.

A compound of general formula (XI) in which Y is —CH$_2$— may be prepared by reducing a nitrile of general formula (XII):

(XII)

wherein Y and R$^4$ are as defined for general formula (I).

The reduction may be carried out using a reducing agent such as a hydride, for example lithium aluminium hydride in an organic solvent such as tetrahydrofuran.

Compounds of general formula (XII) are known and are readily available or may be prepared by methods known to those of skill in the art.

A carboxylic of general formula (X) may be prepared by the hydrolysis of an ester of general formula (XIII):

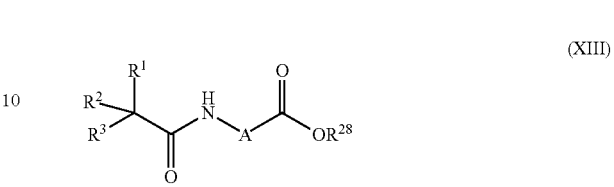

(XIII)

wherein R$^1$, R$^2$, R$^3$ and A are as defined for general formula (I) and R$^{28}$ is C$_{1-6}$ alkyl or benzyl.

Suitably, the hydrolysis is carried out under basic conditions, for example using a metal hydroxide such as lithium hydroxide, sodium hydroxide or potassium hydroxide in an aqueous organic solvent.

A compound of general formula (XIII) may be prepared by reacting a compound of general formula (XIV):

(XIV)

wherein A is as defined for general formula (I) and R$^{28}$ is as defined for general formula (XIII);
with a compound of general formula (XV):

(XV)

wherein R$^1$, R$^2$ and R$^3$ are as defined for general formula (I) and R$^{29}$ is halo, for example chloro or bromo.

Suitably, the reaction is carried out under basic conditions, for example in the presence of an amine such as triethylamine or disopropylethylamine, and in an organic solvent such as dichloromethane.

Compounds of general formulae (XIV) and (XV) are known and are readily available or may be prepared by methods well known to those of skill in the art.

A compound of general formula (I) in which Z$^1$ is *—NHC(O)— and Z$^2$ is *—C(O)NH— may alternatively be prepared by reacting a compound of general formula (XV) as defined above with a compound of general formula (XVI):

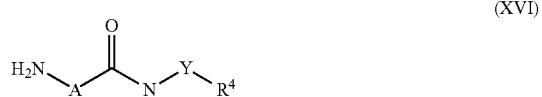

(XVI)

wherein A, Y and R$^4$ are as defined for general formula (I).
Suitably, the reaction is carried out under basic conditions, for example in the presence of an amine such as triethylamine or disopropylethylamine, and in an organic solvent such as dichloromethane.

A compound of general formula (XVI) may be prepared by reacting a compound of general formula (XVII):

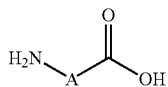

(XVII)

wherein A is as defined for general formula (I);
with a compound of general formula (XI) as defined above.

Suitably, the reaction is carried out using a coupling agent such as HATU under basic conditions, for example in the presence of an amine such as diisopropylethylamine (DIPEA) or triethylamine (TEA) and in an organic solvent such as N,N'-dimethylformamide.

Compounds of general formula (XVII) are known and are readily available or may be prepared by methods well known to those of skill in the art.

Compounds of general formula (I) in which $Z^1$ is *—C(O)NH— and $Z^2$ is *—C(O)NH— may be prepared by reacting a compound of general formula (XX):

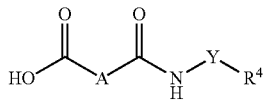

(XX)

wherein A, Y and $R^4$ are as defined for general formula (I);
with a compound of general formula (III) as defined above.

Suitably, the reaction is carried out using a coupling agent such as TBTU under basic conditions, for example in the presence of an amine such as diisopropylethylamine (DIPEA) or triethylamine (TEA) and in an organic solvent such as N,N'-dimethylformamide.

A carboxylic acid of general formula (XX) may be prepared by the hydrolysis of a compound of general formula (XXI):

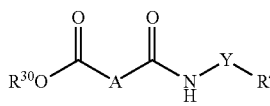

(XXI)

wherein A, Y and $R^4$ are as defined for general formula (I) and $R^{30}$ is $C_{1-6}$ alkyl or benzyl.

Suitably, the hydrolysis is carried out under basic conditions, for example using a metal hydroxide such as lithium hydroxide, sodium hydroxide or potassium hydroxide in an aqueous organic solvent.

A compound of general formula (XXI) may be prepared by reacting a compound of general formula (XXII):

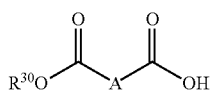

(XXII)

wherein A and Y are as defined for general formula (I) and $R^{30}$ is as defined for general formula (XXI);
with a compound of general formula (XI) as defined above.

Suitably, the reaction is carried out using a coupling agent such as HATU under basic conditions, for example in the presence of an amine such as diisopropylethylamine (DIPEA) or triethylamine (TEA) and in an organic solvent such as N,N'-dimethylformamide.

Compounds of general formula (XXII) are known and are readily available or may be prepared by methods well known to those of skill in the art.

Alternatively, compounds of general formula (I) in which $Z^1$ is *—C(O)NH— and $Z^2$ is *—C(O)NH— may be prepared by reacting a compound of general formula (XXV):

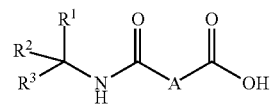

(XXV)

wherein $R^1$, $R^2$, $R^3$ and A are as defined for general formula (I);
with a compound of general formula (XI) as defined above.

Suitably, the reaction is carried out using a coupling agent such as HATU under basic conditions, for example in the presence of an amine such as diisopropylethylamine (DIPEA) or triethylamine (TEA) and in an organic solvent such as N,N'-dimethylformamide. A carboxylic acid of general formula (XXV) may be prepared by the hydrolysis of an ester of general formula (XXVI):

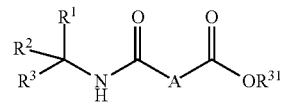

(XXVI)

wherein $R^1$, $R^2$, $R^3$ and A are as defined for general formula (I) and $R^{31}$ is $C_{1-6}$ alkyl or benzyl.

Suitably, the hydrolysis is carried out under basic conditions, for example using a metal hydroxide such as lithium hydroxide, sodium hydroxide or potassium hydroxide in an aqueous organic solvent.

A compound of general formula (XXVI) may be prepared by reacting a compound of general formula (XXVII):

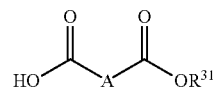

(XXVII)

wherein A is as defined for general formula (I) and $R^{31}$ is as defined for general formula (XXVI),
with a compound of general formula (III) as defined above.

Suitably, the reaction is carried out using a coupling agent such as HATU under basic conditions, for example in the presence of an amine such as diisopropylethylamine (DIPEA) or triethylamine (TEA) and in an organic solvent such as N,N'-dimethylformamide.

Compounds of general formula (XXVII) are known and are readily available or may be prepared by methods well known to those of skill in the art.

Compounds of general formula (I) in which $Z^1$ is *—NHC(O)— and $Z^2$ is *—NHC(O)— may be prepared by reacting a compound of general formula (XXX):

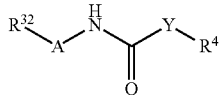
(XXX)

wherein A, Y and $R^4$ are as defined for general formula (I) and $R^{32}$ is halo, for example chloro or bromo;
with a compound of general formula (XXXI)

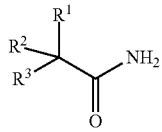
(XXXI)

wherein $R^1$, $R^2$ and $R^3$ are as defined for general formula (I);
in the presence of a phosphorus ligand such as XantPhos, a palladium catalyst and a base such as potassium carbonate.

Compounds of general formula (XXXI) are known and are readily available or may be prepared by methods well known to those of skill in the art.

A compound of general formula (XXX) may be prepared by reacting a compound of general formula (XXXII):

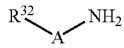
(XXXII)

Wherein A is as defined for general formula (I) and $R^{32}$ is as defined for general formula (XXX);
with a compound of general formula (VI) or (VII) as defined above.

When the compound of general formula (XXXII) is reacted with the carboxylic acid of general formula (VI), the reaction is suitably carried out in the presence of a coupling agent under basic conditions, for example in the presence of an amine such as diisopropylethylamine (DIPEA) and in an organic solvent such as DMF. Suitable coupling agents are as described above.

When the compound of general formula (XXXII) is reacted with an acid halide of general formula (VII), the reaction is suitably carried out under basic conditions, for example in the presence of an amine such as diisopropylethylamine (DIPEA) and in an organic solvent such as dichloromethane.

Compounds of general formula (XXXII) are known and are readily available or may be prepared by methods well known to those of skill in the art.

Compounds of general formula (I) in which $Z^1$ is *—NHC(O)—, $Z^2$ is *—NHC(O)—, Y is —CH$_2$— and $R^4$ is phenyl substituted with OH at the 2-position and $R^{11a}$ at the 5-position may be prepared by reacting a compound of general formula (XXXV):

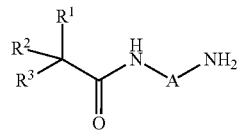
(XXXV)

wherein $R^1$, $R^2$, $R^3$ and A are as defined for general formula (I);
with a 5-substituted 3H-benzofuran-2-one of general formula (XXXIV):

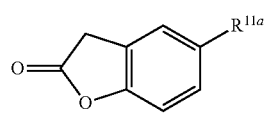
(XXXIV)

where $R^{11a}$ is H, halo, $C_{1-4}$ alkyl, $C_{1-4}$ haloalkyl or C(O)O($C_{1-4}$ alkyl) but is especially halo, particularly fluoro or chloro.

Suitably, the reaction is conducted at elevated temperature, for example at about 100 to 140° C., typically at about 120° C., in an organic solvent such as toluene.

5-Chloro-3H-benzofuran-2-one may be prepared by the method described in *Journal of Fluorine Chemistry* 99 (1999) 189-195.

A compound of general formula (XXXV) may also be reacted with a compound of general formula (XXXIX):

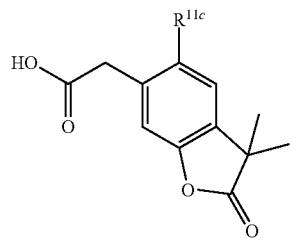
(XXXIX)

wherein $R^{11c}$ is H, halo, CN, $C_{1-4}$ alkyl or $C_{1-4}$ haloalkyl, especially halo such as fluoro or chloro;
followed by reduction, for example with a hydride reducing agent such as lithium borohydride to give a compound of general formula (I) in which $R^4$ is phenyl substituted with OH at the 3-position, with —C(CH$_3$)$_2$—CH$_2$OH at the 4-position and with $R^{11}$ at the 6-position.

The reaction between the compounds of general formulae (XXXV) and (XXXIX) is suitably conducted in the presence of a coupling reagent such as T3P® under basic conditions, for example in the presence of DIPEA.

A compound of general formula (XXXV) may be prepared by reacting a compound of general formula (XXXVI):

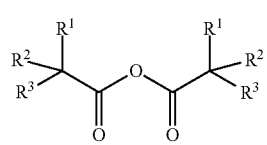
(XXXVI)

wherein $R^1$, $R^2$ and $R^3$ are as defined for general formula (I);

with a compound of general formula (XXXVII):

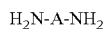     (XXXVII)

wherein A is as defined for general formula (I);

in the presence of a base, typically an amine such as DIPEA.

The reaction may initially be conducted at reduced temperature, for example about 0° C., before being allowed to warm to room temperature (about 15 to 25° C.). Suitable reaction solvents include organic solvents such as dichloromethane.

Compounds of general formula (XXXVI) and (XXXVII) are known and are readily available or may be prepared by methods well known to those of skill in the art. Benzene-1,3-diamine is an example of a compound of general formula (XXXVII).

A compound of general formula (XXXIX) may be prepared from a compound of general formula (XL):

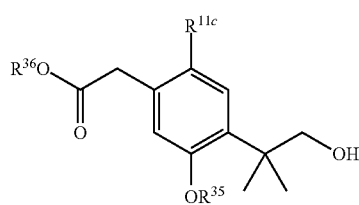     (XL)

wherein $R^{11c}$ is as defined above for general formula (XXXIX); $R^{35}$ is $C_{1-6}$ alkyl or benzyl;

and $R^{36}$ is $C_{1-6}$ alkyl or benzyl;

by reaction with boron tribromide as described in Example 9 below.

A compound of general formula (XL) may be prepared from a compound of general formula (XLI):

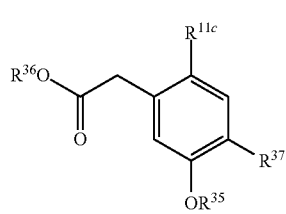     (XLI)

wherein $R^{11c}$ is as defined above for general formula (XXXIX); $R^{35}$ and $R^{36}$ are as defined above for general formula (XL) and $R^{37}$ is halo, for example chloro or bromo and especially bromo;

by reaction with (1-methoxy-2-methyl-prop-1-enoxy)-trimethyl-silane.

The reaction is carried out in the presence of a palladium catalysts such as $Pd(PtBu_3)_2)$ in the presence of $ZnF_2$ and suitably under inert conditions, for example under a nitrogen atmosphere in a degassed organic solvent such as N,N-dimethylformamide at elevated temperature, for example 60 to 100° C.

A compound of general formula (XLI) may be prepared by the reaction of a compound of general formula (XLII):

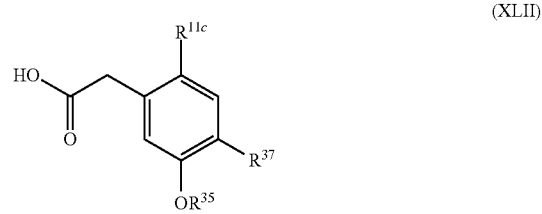     (XLII)

wherein $R^{11c}$ is as defined above for general formula (XXXIX); $R^{35}$ is as defined above for general formula (XL) and $R^{37}$ is as defined above for general formula (XLI);

with a compound of general formula (XLIII):

     (XLIII)

wherein $R^{36}$ is as defined above for general formula (XL) and $R^{38}$ is halo, especially bromo. Compounds of general formula (XLIII) are readily available or may be prepared by methods familiar to those of skill in the art.

A compound of general formula (XLII) may be prepared by halogenating a compound of general formula (XLIV):

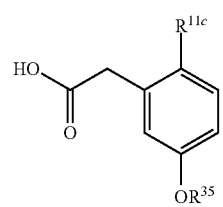     (XLIV)

wherein $R^{11c}$ is as defined above for general formula (XXXIX); and $R^{35}$ is as defined above for general formula (XL).

Suitable halogenating agents are well known to those of skill in the art and, for example, when $R^{37}$ is bromo, the halogenating agent may be bromine, for example a solution of bromine in acetonitrile as described in Example 9 below.

An alternative method for preparing a compound of general formula (I) in which $Z^1$ is *—C(O)NH—, $Z^2$ is *—NHC(O)—, A is:

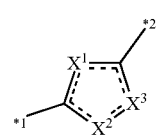

and $R^4$ is phenyl substituted with OH at the 3-position, with —C(CH$_3$)$_2$—CH$_2$OH at the 4-position and with $R^{11}$ at the 6-position is by reaction of a compound of general formula (XLV):

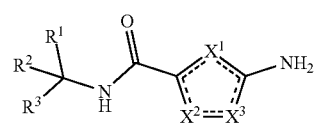     (XLV)

wherein R¹, R², R³, X¹, X² and X³ are as defined for general formula (I);

with a compound of general formula (XXXIX) as defined above, followed by reduction, for example with a hydride reducing agent such as lithium borohydride.

Suitably, the reaction is conducted in the presence of a coupling reagent such as T3P® under basic conditions, for example in the presence of DIPEA.

A compound of general formula (XLV) may be prepared by reducing a compound of general formula (XLVI):

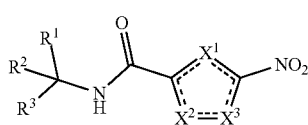

(XLVI)

wherein R¹, R², R³, X¹, X² and X³ are as defined for general formula (I).

Suitably, the reduction is carried out by catalytic hydrogenation, for example using a palladium on carbon catalyst.

A compound of general formula (XLVI) may be prepared by reacting a compound of general formula (XLVII):

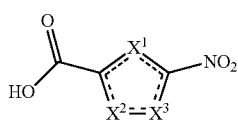

(XLVII)

wherein

X¹, X² and X³ are as defined for general formula (I).

with a compound of general formula (III) as defined above. Suitably, the reaction is carried out in the presence of a coupling reagent under conditions similar to those discussed above for the reaction of the compound of general formula (II) with the compound of general formula (III).

Compounds of general formulae (II), (X), (XVI), (XX), (XXV), (XXX) or (XXXV) form a further aspect of the invention.

Compounds of general formula (I) may also be prepared from other compounds of general formula (I). For example, when either R³; R¹, R² and R³ together; or R⁴ includes a phenyl group substituted with alkoxy, this can be converted to phenyl substituted with OH by treatment with boron tribromide.

Other interconversions of the various substituent groups can be carried out by methods familiar to those of skill in the art.

The compounds of general formula (I) are modulators of TMEM16A and therefore, in a further aspect of the invention, there is provided a compound of general formula (I) as defined above for use in medicine, particularly in the treatment or prophylaxis of diseases and conditions affected by modulation of TMEM16A.

There is also provided the use of a compound of general formula (I) in the manufacture of a medicament for the treatment or prophylaxis of diseases and conditions affected by modulation of TMEM16A.

There is also provided a method for the treatment or prophylaxis of diseases and conditions affected by modulation of TMEM16A, the method comprising administering to a patient in need of such treatment an effective amount of a compound of general formula (I).

The diseases and conditions affected by modulation of TMEM16A include respiratory diseases and conditions, dry mouth (xerostomia), intestinal hypermobility, cholestasis and ocular conditions.

There is also provided:

A compound of general formula (I) for use in the treatment or prophylaxis of respiratory diseases and conditions.

A compound of general formula (I) for use in the treatment or prophylaxis of dry mouth (xerostomia).

A compound of general formula (I) for use in the treatment or prophylaxis of intestinal hypermobility.

A compound of general formula (I) for use in the treatment or prophylaxis of cholestasis.

A compound of general formula (I) for use in the treatment or prophylaxis of ocular conditions.

The invention also provides:

The use of a compound of general formula (I) in the manufacture of a medicament for the treatment or prophylaxis of respiratory diseases and conditions.

The use of a compound of general formula (I) in the manufacture of a medicament for the treatment or prophylaxis of dry mouth (xerostomia).

The use of a compound of general formula (I) in the manufacture of a medicament for the treatment or prophylaxis of intestinal hypermobility.

The use of a compound of general formula (I) in the manufacture of a medicament for the treatment or prophylaxis of cholestasis.

The use of a compound of general formula (I) in the manufacture of a medicament for the treatment or prophylaxis of ocular conditions.

There is further provided:

A method for the treatment or prophylaxis of respiratory diseases and conditions, the method comprising administering to a patient in need of such treatment an effective amount of a compound of general formula (I).

A method for the treatment or prophylaxis of dry mouth (xerostomia), the method comprising administering to a patient in need of such treatment an effective amount of a compound of general formula (I).

A method for the treatment or prophylaxis of intestinal hypermobility, the method comprising administering to a patient in need of such treatment an effective amount of a compound of general formula (I).

A method for the treatment or prophylaxis of cholestasis, the method comprising administering to a patient in need of such treatment an effective amount of a compound of general formula (I).

A method for the treatment or prophylaxis of ocular conditions, the method comprising administering to a patient in need of such treatment an effective amount of a compound of general formula (I).

Respiratory diseases and conditions which may be treated or prevented by the compounds of general formula (I) include cystic fibrosis, chronic obstructive pulmonary disease (COPD), chronic bronchitis, emphysema, bronchiectasis, including non-cystic fibrosis bronchiectasis, asthma and primary ciliary dyskinesia.

Dry mouth (xerostomia) which may be treated or prevented by the compounds of general formula (I) may result from Sjorgens syndrome, radiotherapy treatment and xerogenic drugs.

Intestinal hypermobility which may be treated or prevented by the compounds of general formula (I) may be associated with gastric dyspepsia, gastroparesis, chronic constipation and irritable bowel syndrome.

Ocular conditions which may be treated or prevented by the compounds of by the compounds of general formula (I) include dry eye disease.

The compounds of the present invention will generally be administered as part of a pharmaceutical composition and therefore the invention further provides a pharmaceutical composition comprising a compound of general formula (I) together with a pharmaceutically acceptable excipient.

More suitable compounds of general formula (I) for use in the pharmaceutical compositions are as discussed above.

The pharmaceutical composition may be formulated for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The composition may be prepared by bringing into association the above defined active agent with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac® 70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 μm e.g. around 1-5 μm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 μm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

Parenteral formulations will generally be sterile.

The medical practitioner, or other skilled person, will be able to determine a suitable dosage for the compound of general formula (I) and hence the amount of the compound of the invention that should be included in any particular pharmaceutical formulation (whether in unit dosage form or otherwise).

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

There is also provided a compound of general formula (I) in combination with an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

Suitable additional active agents which may be included in a pharmaceutical composition or a combined preparation with the compounds of general formula (I) include: β2 adrenoreceptor agonists such as metaproterenol, isoproterenol, isoprenaline, albuterol, salbutamol, formoterol, salmeterol, indacaterol, terbutaline, orciprenaline, bitolterol mesylate, pirbuterol, olodaterol, vilanterol and abediterol;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

dornase alpha;

corticosteroids such as prednisone, prednisolone, flunisolide, triamcinolone acetonide, beclomethasone dipropionate, budesonide, fluticasone propionate mometasone furoate and fluticasone furoate;

Leukotriene antagonists such as montelukast and zafirlukast;

anticholinergic compounds, particularly muscarinic antagonists such as ipratropium, tiotropium, glycopyrrolate, aclidinium and umeclidinium;

CFTR repair therapies (e.g. CFTR potentiators, correctors or amplifiers) such as Ivacaftor, QBW251, Bamacaftor (VX659), Elexacaftor (VX445), VX561/CPT-656, VX152, VX440, GLP2737, GLP2222, GLP2451, PTI438, PTI801, PTI808, FDL-169 and FDL-176 and CFTR correctors such as Lumacaftor and Tezacaftor or combinations thereof (for example a combination of Ivacaftor, Tezacaftor and Elexacaftor);

ENaC modulators, particularly ENaC inhibitors;

Antibiotics;

Antivirals such as ribavirin and neuraminidase inhibitors such as zanamivir;

Antifungals such as PUR1900;

Airway hydrating agents (osmoloytes) such as hypertonic saline and mannitol (Bronchitol®); and Mucolytic agents e.g. N-acetyl cysteine.

When the additional active agent is an ENaC modulator, it may be an ENaC inhibitor such as amiloride, VX-371, AZD5634, QBW276, SPX-101, B1443651, B11265162 and ETD001. Other suitable ENaC blockers are disclosed in our applications WO 2017/221008, WO 2018/096325, WO 2019/077340 and WO 2019/220147 and any of the example compounds of those applications may be used in combination with the compounds of general formula (I), (Ix), (IA), (IB), (IC), (ID) or (IE). Particularly suitable compounds for use in combination with the compounds of general formula (I), (Ix), (IA), (IB), (IC), (ID) or (IE) include compounds having a cation selected from:

2-[({3-amino-5H-pyrrolo[2,3-b]pyrazin-2-yl}formamido)ethyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;

2-[({3-amino-5H-pyrrolo[2,3-b]pyrazin-2-yl}formamido)methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

and a suitable anion, for example halide, sulfate, nitrate, phosphate, formate, acetate, trifluoroacetate, fumarate, citrate, tartrate, oxalate, succinate, mandelate, methane sulfonate or p-toluene sulfonate.

The invention is illustrated by the following non-limiting Examples and the drawing in which:

FIG. 1 is an example trace from a whole-cell patch clamp (Qpatch) TMEM16A potentiator assay as used in Biological Example 95 and illustrates the methodology used in the assay.

EXAMPLES

General Conditions

Mass spectra were run on LC-MS systems using electrospray ionization. These were run using either a Waters Acquity uPLC system with Waters PDA and ELS detectors or Shimadzu LCMS-2010EV systems. [M+H]+ refers to mono-isotopic molecular weights.

NMR spectra were recorded on a Bruker Avance III HD 500 MHz with a 5 mm Broad Band Inverse probe, a Bruker Avance III HD 250 MHz or a 400 MHz Avance III HD Nanobay fitted with a 5 mm Broad Band Observed SmartProbe using the solvent as internal deuterium lock. Spectra were recorded at room temperature unless otherwise stated and were referenced using the solvent peak.

Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

Compounds were purified by flash column chromatography on normal phase silica on Biotage® Isolera systems using the appropriate SNAP cartridge and gradient. Alternatively, compounds were purified on reverse phase silica using Biotage® Isolera systems with the appropriate SNAP C18 cartridges and reverse phase eluent or by preparative HPLC (if stated otherwise).

Preparative HPLC Using Acidic pH, Early Elution Method

Purifications by were performed on a Gilson LC system using Waters Sunfire C18 columns (30 mm×100 mm, 10 µM; temperature: RT) and a gradient of 10-95% B (A=0.1% formic acid in water; B=0.1% formic acid in acetonitrile) over 14.44 min then 95% B for 2.11 min, with an injection volume of 1500 µL and a flow rate of 40 mL/min. UV spectra were recorded at 215 nm using a Gilson detector.

Preparative HPLC Using Acidic pH, Standard Elution Method

Purifications by preparative HPLC (acidic pH, standard elution method) were performed on a Gilson LC system using Waters Sunfire C18 columns (30 mm×100 mm, 10 µM; temperature: RT) and a gradient of 30-95% B (A=0.1% formic acid in water; B=0.1% formic acid in acetonitrile) over 11 min then 95% B for 2.11 min, with an injection volume of 1500 µL and a flow rate of 40 mL/min. UV spectra were recorded at 215 nm using a Gilson detector.

Preparative HPLC Using Basic pH, Early Elution Method

Purifications by preparative HPLC (basic pH, early elution method) were performed on a Gilson LC system using Waters Xbridge C18 columns (30 mm×100 mm, 10 µM; temperature: RT) and a gradient of 10-95% (A=0.2% ammonium hydroxide in water; B=0.2% ammonium hydroxide in acetonitrile) over 14.44 min then 95% B for 2.11 min, with an injection volume of 1500 µL and a flow rate of 40 mL/min. UV spectra were recorded at 215 nm using a Gilson detector.

Preparative HPLC Using Basic pH, Standard Elution Method

Purifications by preparative HPLC (basic pH, standard elution method) were performed on a Gilson LC system using Waters Xbridge C18 columns (30 mm×100 mm, 10 µM; temperature: RT) and a gradient of 30-95% (A=0.2% ammonium hydroxide in water; B=0.2% ammonium hydroxide in acetonitrile) over 11 min then 95% B for 2.11 min, with an injection volume of 1500 µL and a flow rate of 40 mL/min. UV spectra were recorded at 215 nm using a Gilson detector.

If not indicated otherwise, the analytical HPLC conditions are as follows:

Method A

Column: Phenomenex Kinetix-XB 018 2.1×100 mm, 1.7 µm

Column Temp: 40° C.

Eluents: A: $H_2O$+0.1% formic acid, B: acetonitrile+0.1% formic acid
Flow Rate: 0.6 mL/min
Gradient: 0-5.3 min 5-100% B, 5.3-5.8 min 100% B, 5.8-5.82 min 100-5% B, 5.82-7.00 min 5% B Method B Column: Waters UPLC® BEH™ C18 2.1×100 mm, 1.7 μm
Column Temp: 40° C.
Eluents: A: 2 mM ammonium bicarbonate, buffered to pH10, B: acetonitrile
Flow Rate: 0.6 mL/min
Gradient: 0-5.3 min 5-100% B, 5.3-5.8 min 100% B, 5.8-5.82 min 100-5% B, 5.82-7.00 min 5% B Method C Column: Kinetex Core-Shell C18 2.1×50 mm, 5 μm
Column Temp: 40° C.
Eluents: A: $H_2O$+0.1% formic acid, B: acetonitrile+0.1% formic acid
Flow Rate: 1.2 mL/min
Gradient: 0-1.20 min 5-100% B, 1.20-1.30 min 100% B, 1.30-1.31 min 100-5% B, 1.31-1.7 min 5% B Method G Column: Waters UPLC® BEH™ C18, 2.1 mm×50 mm, 1.7 μm,
Column Temp: 40° C.
Eluents: A: $H_2O$+0.1% formic acid, B: acetonitrile+0.1% formic acid
Flow Rate: 0.9 mL/min
Gradient: 0-1.10 mins 5-100% B, 1.10-1.35 mins 100% B, 1.35-1.40 mins 100-1% B Method H Column: Kinetex Core-Shell C18 2.1×50 mm, 5 μm
Column Temp: 40° C.
Eluents: A: $H_2O$+0.1% formic acid, B: acetonitrile+0.1% formic acid
Flow Rate: 1.2 mL/min
Gradient: 0-1.83 min 5-100% B, 1.83-2.25 min 100% B, 2.25-2.26 min The following example are intended to illustrate the invention and are not to be construed as being limitations thereon. Temperatures are given in degrees centigrade. If not mentioned otherwise, all evaporations are performed in vacuo, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, and NMR. Abbreviations used are those conventional in the art. If not defined, the terms have their generally accepted meanings.

ABBREVIATION aq. aqueous
br broad
d doublet
dd doublet of doublets
DCM dichloromethane
DIPEA diisopropylethylamine
DMF N,N-dimethylformamide
EtOAc ethyl acetate
HATU 2-(7-aza-1H-benzotriazole-1-yl)-1,1,3,3-tetramethyluronium hexafluorophosphate
HPLC high pressure liquid chromatography
MeCN acetonitrile
MS mass spectrometry
m multiplet
min minute(s)
mL milliliter(s)
m/z mass to charge ratio
NMR nuclear magnetic resonance
Rt retention time
s singlet
t triplet
TBTU N,N,N',N'-tetramethyl-O-(benzotriazol-1-yl)uronium tetrafluoroborate
TEA triethylamine
TFA trifluoroacetic acid
THF tetrahydrofuran

PREPARATION EXAMPLES

Example 1

N-tert-Butyl-5-[[2-(5-chloro-2-hydroxy-phenyl)acetyl]amino]thiophene-2-carboxamide

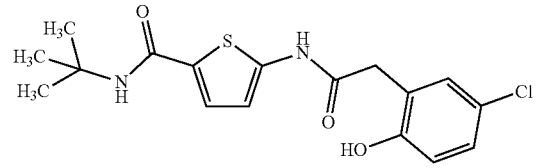 [SMILES: CC(C)(C)NC(=O)c1ccc(NC(=O)Cc2cc(Cl)ccc2O)s1]

Step 1: Methyl 5-[[2-(5-chloro-2-methoxy-phenyl)acetyl]amino]thiophene-2-carboxylate

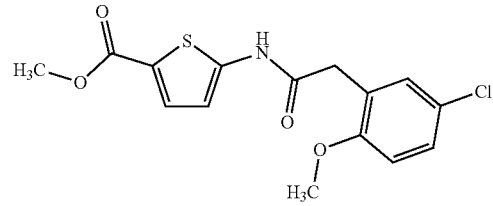 [SMILES: COC(=O)c1ccc(NC(=O)Cc2cc(Cl)ccc2OC)s1]

To a solution of 2-(5-chloro-2-methoxy-phenyl)acetic acid (351 mg, 1.75 mmol) and DIPEA (306 μL, 1.75 mmol) in DMF (8 mL) was added HATU (665 mg, 1.75 mmol) followed by methyl 5-aminothiophene-2-carboxylate (250 mg, 1.59 mmol) and the mixture stirred at room temperature overnight. The resulting mixture was diluted with EtOAc (30 mL) and washed with 1M HCl (30 mL) solution and brine (30 mL). The organic portion was separated, dried over $Na_2SO_4$ and concentrated in vacuo. The crude residue was absorbed onto silica and purification by chromatography on silica eluting with 0-50% EtOAc in heptanes afforded the title compound as a colourless waxy solid.

LC-MS (Method C): Rt 1.15 min; MS m/z 340.0/341.9=[M+H]+ (81%@215 nm)

1H NMR (500 MHz, DMSO-d6) δ 11.79 (s, 1H), 7.60 (d, J=4.2 Hz, 1H), 7.33-7.26 (m, 2H), 7.02-6.98 (m, 1H), 6.72 (d, J=4.2 Hz, 1H), 3.76 (s, 3H), 3.75 (s, 3H), 3.72 (s, 2H).

Step 2: 5-[[2-(5-Chloro-2-methoxy-phenyl)acetyl]amino]thiophene-2-carboxylic acid

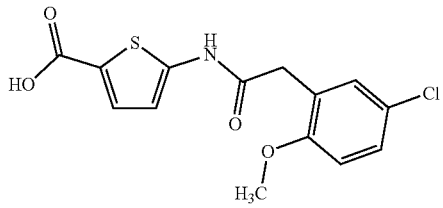 [SMILES: COc1ccc(Cl)cc1CC(=O)Nc1ccc(C(=O)O)s1]

To a solution of methyl 5-[[2-(5-chloro-2-methoxy-phenyl)acetyl]amino]thiophene-2-carboxylate (step 1) (95%, 268 mg, 0.75 mmol) in EtOAc (1.33 mL), THF (1.33 mL) and water (1.33 mL) was added LiOH·H₂O (63 mg, 1.5 mmol) and the mixture was stirred at room temperature for 4 h. Further LiOH·H₂O (95 mg, 2.25 mmol) was added and the mixture stirred at room temperature for 2 days followed by heating to 50° C. for 2 h. After cooling to room temperature, the mixture was acidified to pH 2 using 1M HCl (4 mL). The resulting precipitate was filtered, washed with water and dried in a vacuum oven to afford the title compound.

LC-MS (Method C): Rt 1.06 min; MS m/z 323.9/325.8= [M−H] (96%@215 nm)

1H NMR (500 MHz, DMSO-d6) δ 11.70 (s, 1H), 7.51 (d, J=4.1 Hz, 1H), 7.33-7.28 (m, 2H), 7.01 (d, J=9.4 Hz, 1H), 6.69 (d, J=4.1 Hz, 1H), 3.75 (s, 3H), 3.71 (s, 2H).

Step 3: N-tert-Butyl-5-[[2-(5-chloro-2-methoxy-phenyl)acetyl]amino]thiophene-2-carboxamide

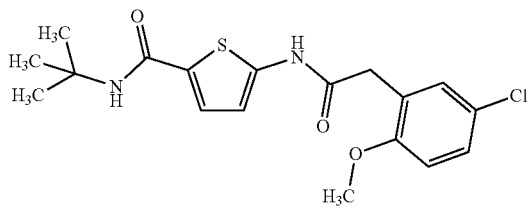 [SMILES: COc1ccc(Cl)cc1CC(=O)Nc1ccc(C(=O)NC(C)(C)C)s1]

To a solution of 5-[[2-(5-chloro-2-methoxy-phenyl)acetyl]amino]thiophene-2-carboxylic acid (step 2) (130 mg, 0.40 mmol) and DIPEA (84 µL, 0.48 mmol) in DMF (2 mL) was added HATU (182 mg, 0.48 mmol) followed by 2-methylpropan-2-amine (50 µL, 0.48 mmol) and the mixture was stirred at room temperature overnight. The resulting mixture was diluted with EtOAc (10 mL) and washed with 1M HCl (10 mL) and brine (10 mL), dried over Na₂SO₄ and concentrated in vacuo. The crude residue was absorbed onto silica and purified by chromatography on silica eluting with 0-50% EtOAc in heptanes to afford the title compound as a colourless powder.

LC-MS (Method C): Rt 1.17 min; MS m/z 381.0/383.0= [M+H]+ (100%@215 nm) 1H NMR (500 MHz, DMSO-d6) δ 11.44 (s, 1H), 7.54 (d, J=4.1 Hz, 1H), 7.49 (s, 1H), 7.32-7.29 (m, 2H), 7.01 (d, J=8.4 Hz, 1H), 6.61 (d, J=4.1 Hz, 1H), 3.75 (s, 3H), 3.68 (s, 2H), 1.34 (s, 9H).

Step 4: N-tert-Butyl-5-[[2-(5-chloro-2-hydroxy-phenyl)acetyl]amino]thiophene-2-carboxamide To a solution of N-tert-butyl-5-[[2-(5-chloro-2-methoxy-phenyl)acetyl]amino]thiophene-2-carboxamide (step 3) (100%, 130 mg, 0.34 mmol) in DCM (1.5 mL) at 0° C. was added 1M BBr₃ in DCM (0.51 mL, 0.51 mmol) and the mixture was stirred at room temperature for 1 h. The reaction was quenched by addition of sat. NaHCO₃ solution (10 mL) and the resulting mixture extracted with CHCl₃/IPA (3:1, 2×10 mL). The combined organic extracts were washed with brine (10 mL), dried over Na₂SO₄ and concentrated in vacuo. The crude residue was absorbed onto silica and purification by chromatography on silica eluting with 0-50% EtOAc in heptanes afforded the title compound as a colourless powder.

LC-MS (Method A): Rt 2.97 min; MS m/z 367.1/369.1= [M+H]+ (98%@215 nm)

1H NMR (500 MHz, DMSO-d6) δ 11.41 (s (br), J=14.4 Hz, 1H), 9.83 (s (br), 1H), 7.55 (d, J=4.1 Hz, 1H), 7.50 (s, 1H), 7.21 (d, J=2.7 Hz, 1H), 7.13 (dd, J=8.6, 2.7 Hz, 1H), 6.81 (d, J=8.6 Hz, 1H), 6.61 (d, J=4.1 Hz, 1H), 3.64 (s, 2H), 1.35 (s, 9H).

Example 1.1

N-tert-Butyl-5-[[2-(5-chloro-2-hydroxy-phenyl)acetyl]amino]thiophene-3-carboxamide

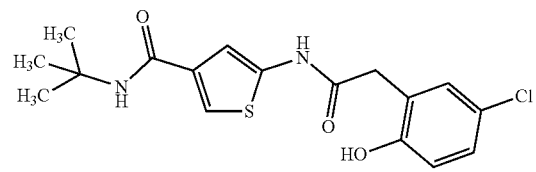 [SMILES: CC(C)(C)NC(=O)c1csc(NC(=O)Cc2cc(Cl)ccc2O)c1]

The title compound was prepared analogously to Example 1 by replacing methyl 5-aminothiophene-2-carboxylate (step 1) with methyl 5-aminothiophene-3-carboxylate.

LC-MS (Method A): Rt 2.97 min; MS m/z 367.2/369.1= [M+H]+ (97%@215 nm)

1H NMR (500 MHz, DMSO-d6) δ 11.29 (s (br), 1H), 9.84 (s (br), 1H), 7.53 (d, J=1.7 Hz, 1H), 7.46 (s, 1H), 7.20 (d, J=2.7 Hz, 1H), 7.12 (dd, J=8.6, 2.7 Hz, 1H), 6.95 (d, J=1.7 Hz, 1H), 6.80 (d, J=8.6 Hz, 1H), 3.62 (s, 2H), 1.34 (s, 9H).

Example 1.2

N-tert-Butyl-4-[[2-(5-chloro-2-hydroxy-phenyl)acetyl]amino]thiophene-2-carboxamide

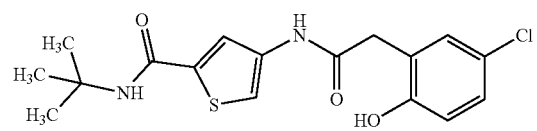 [SMILES: CC(C)(C)NC(=O)c1cc(NC(=O)Cc2cc(Cl)ccc2O)cs1]

Step 1: Methyl 4-[[2-(5-chloro-2-methoxy-phenyl)acetyl]amino]thiophene-2-carboxylate

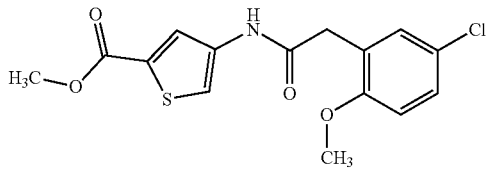 [SMILES: COC(=O)c1cc(NC(=O)Cc2cc(Cl)ccc2OC)cs1]

2-(5-Chloro-2-methoxy-phenyl)acetic acid (0.16 g, 0.82 mmol) was dissolved in thionyl chloride (0.73 mL, 8.24 mmol) and the mixture heated to 70° C. for 1 h. The resulting mixture was concentrated in vacuo and the residue azeotroped with toluene (2×2 ml). The crude acid chloride was dissolved in DCM (1 mL) and added to a cooled (0° C.) solution of methyl 4-aminothiophene-2-carboxylate (125 mg, 0.80 mmol) and DIPEA (0.28 mL, 1.59 mmol) in DCM (2 mL). The resulting mixture was stirred and allowed to warm to room temperature. After 1 hour the mixture was diluted with DCM (4 ml) and water (5 mL), the phases separated and the aqueous portion extracted with DCM (5 mL). The combined organic extracts were concentrated in vacuo to give a pale brown solid. The product was by purified by chromatography on silica eluting with 0-80% EtOAc in heptanes to afford the title compound as a white waxy solid.

LC-MS (Method C): Rt 1.16 min; MS m/z 339.9/341.9=[M+H]+ (100%@215 nm)

1H NMR (500 MHz, DMSO-d6) δ 10.57 (s, 1H), 7.79 (d, J=1.6 Hz, 1H), 7.78 (d, J=1.6 Hz, 1H), 7.31-7.27 (m, 2H), 7.02-6.98 (m, 1H), 3.81 (s, 3H), 3.76 (s, 3H), 3.62 (s, 2H).

Step 2-4: N-tert-Butyl-4-[[2-(5-chloro-2-hydroxy-phenyl)acetyl]amino]thiophene-2-carboxamide The title compound was prepared from methyl 4-[[2-(5-chloro-2-methoxy-phenyl)acetyl]amino]thiophene-2-carboxylate (step 1) analogously to Example 1 steps 2-4.

LC-MS (Method A): Rt 3.09 min; MS m/z 367.2/369.1=[M+H]+ (97% @215 nm)

1H NMR (500 MHz, DMSO-d6) δ 10.44 (s, 1H), 9.78 (s, 1H), 7.85 (s, 1H), 7.80 (d, J=1.4 Hz, 1H), 7.49 (d, J=1.4 Hz, 1H), 7.19 (d, J=2.6 Hz, 1H), 7.10 (dd, J=8.6, 2.7 Hz, 1H), 6.79 (d, J=8.6 Hz, 1H), 3.56 (s, 2H), 1.35 (s, 9H).

Example 2

N-[(5-Chloro-2-hydroxy-phenyl)methyl]-3-(2,2-dimethylpropanoylamino)benzamide

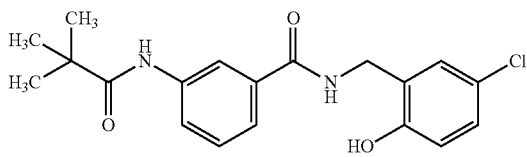

Step 1: Methyl 3-(2,2-dimethylpropanoylamino)benzoate

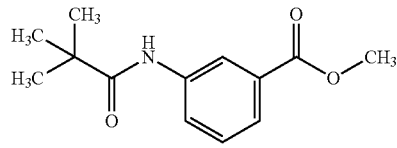 [SMILES: COC(=O)c1cccc(NC(=O)C(C)(C)C)c1]

To a cooled (0° C.) mixture of methyl 3-aminobenzoate (500 mg, 3.31 mmol) and TEA (1.73 mL, 9.92 mmol) in DCM (5.5 mL) was added 2,2-dimethylpropanoyl chloride (0.61 mL, 4.96 mmol) and the resulting mixture stirred for 2 h. The reaction mixture was diluted with DCM (5 mL) and the organic portion was washed with sat. aqueous sodium hydrogen carbonate solution (5 mL), brine (5 mL), dried over Na2SO4 and concentrated in vacuo to afford the title compound as a light brown solid.

LC-MS (Method C): Rt 1.08 min; MS m/z 236.1=[M+H]+ (99%@215 nm)

1H NMR (250 MHz, DMSO-d6) δ 9.43 (s, 1H), 8.30 (t, J=1.9 Hz, 1H), 7.95 (ddd, J=8.1, 2.2, 1.1 Hz, 1H), 7.63 (dt, J=7.7, 1.2 Hz, 1H), 7.43 (t, J=7.9 Hz, 1H), 3.85 (s, 3H), 1.23 (s, 9H).

Step 2: 3-(2,2-Dimethylpropanoylamino)benzoic acid

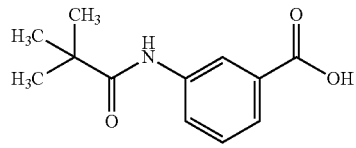 [SMILES: CC(C)(C)C(=O)Nc1cccc(C(=O)O)c1]

To a solution of methyl 3-(2,2-dimethylpropanoylamino)benzoate (step 1) (99%, 706 mg, 2.97 mmol) in 2:1 THF/water (11 mL) was added 1M LiOH (14.85 mL, 14.85 mmol) and the mixture was stirred for 1 h. The resulting mixture was diluted with water (20 mL) and acidified to pH 1 by the dropwise addition of 6M HCl. The mixture was extracted with EtOAc (3×15 mL) and the combined organic extracts were washed with brine (30 mL), dried over Na2SO4 and concentrated in vacuo to afford the title compound as a light brown solid.

LC-MS (Method C): Rt 0.97 min; MS m/z 222.0=[M+H]+ (100%@215 nm)

1H NMR (500 MHz, DMSO-d6) δ 9.38 (s, 1H), 8.25 (t, J=1.8 Hz, 1H), 7.91 (ddd, J=8.1, 2.2, 1.0 Hz, 1H), 7.61 (dt, J=7.7, 1.3 Hz, 1H), 7.40 (t, J=7.9 Hz, 1H), 1.23 (s, 9H).

Step 3: (5-Chloro-2-methoxy-phenyl)methanamine

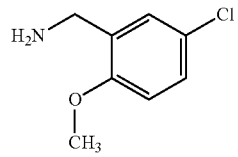

A cooled (0° C.) solution of 5-chloro-2-methoxy-benzonitrile (500 mg, 2.98 mmol) in THF (7.5 mL) was added dropwise to a cooled solution of 2.4M LiAlH₄ solution in THF (1.86 mL, 4.48 mmol) in THF (5.5 mL). The mixture was allowed to warm to room temperature and stirred for 3 h. The reaction was quenched by slow addition of water (0.25 mL) followed by 4M NaOH (0.25 mL). The mixture was filtered through Celite® (filter material) rinsing through with EtOAc (2×5 mL). The filtrate was concentrated in vacuo to afford the title compound as a yellow oil.

LC-MS (Method B): Rt 2.43 min; MS m/z 171.7/173.7= [M+H]+ (89%@215 nm)

1H NMR (500 MHz, DMSO-d6) δ 7.38 (d, J=2.7 Hz, 1H), 7.21 (dd, J=8.7, 2.7 Hz, 1H), 6.94 (d, J=8.7 Hz, 1H), 3.77 (s, 3H), 3.64 (s, 2H), 1.89 (s (br), 2H).

Step 4: N-[(5-Chloro-2-methoxy-phenyl)methyl]-3-(2,2-dimethylpropanoylamino) benzamide

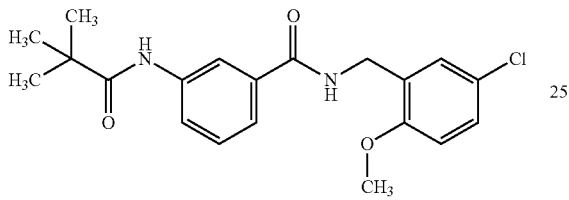

To a solution of 3-(2,2-dimethylpropanoylamino)benzoic acid (step 2) (100 mg, 0.45 mmol) and (5-chloro-2-methoxyphenyl)methanamine (step 3)(89%, 95.9 mg, 0.50 mmol) in 1,4-dioxane (3 mL) was added TEA (0.20 mL, 1.13 mmol) and 50% T3P® solution in EtOAc (0.27 mL, 0.45 mmol) and the mixture stirred at room temperature for 2 h. The reaction mixture was diluted with water (5 mL) and extracted into EtOAc (3×5 mL). The combined organic extracts were washed with sat. aqueous sodium hydrogen carbonate (10 mL), brine (10 mL), dried over Na₂SO₄ and concentrated in vacuo to afford the title compound as a yellow oil.

LC-MS (Method C): Rt 1.18 min; MS m/z 375.1/377.0= [M+H]+ (95%@215 nm) 1H NMR (500 MHz, DMSO-d6) δ 9.37 (s, 1H), 8.86 (t, J=5.9 Hz, 1H), 8.11 (t, J=1.8 Hz, 1H), 7.88-7.85 (m, 1H), 7.60-7.56 (m, 1H), 7.40 (t, J=7.9 Hz, 1H), 7.28 (dd, J=8.7, 2.7 Hz, 1H), 7.13 (d, J=2.7 Hz, 1H), 7.03 (d, J=8.8 Hz, 1H), 4.41 (d, J=5.9 Hz, 2H), 3.83 (s, 3H), 1.23 (s, 9H).

Step 5: N-[(5-Chloro-2-hydroxy-phenyl)methyl]-3-(2,2-dimethylpropanoylamino) benzamide To a cooled (0° C.) solution N-[(5-chloro-2-methoxyphenyl)methyl]-3-(2,2-dimethyl propanoylamino)benzamide (step 4) (95%, 150 mg, 0.38 mmol) in DCM (3.23 mL) was added 1M BBr₃ in DCM (1.14 mL, 1.14 mmol) dropwise and allowed to warm to room temperature, stirring for 100 min. The reaction was quenched with sat. aqueous sodium hydrogen carbonate (5 mL) and the mixture extracted into EtOAc (3×5 mL). The combined organic extracts were dried over Na₂SO₄ and concentrated in vacuo. Purification of the crude residue by preparative HPLC (acidic pH, early elution method) afforded the title compound as a white solid.

LC-MS (Method A): Rt 3.20 min; MS m/z 361.1/363.2= [M+H]+ (98%@215 nm)

1H NMR (500 MHz, DMSO-d6) δ 9.91 (s, 1H), 9.37 (s, 1H), 8.90 (t, J=5.9 Hz, 1H), 8.11 (t, J=1.8 Hz, 1H), 7.88-7.84 (m, 1H), 7.57 (d, J=7.9 Hz, 1H), 7.39 (t, J=7.9 Hz, 1H), 7.11 (dd, J=8.5, 2.7 Hz, 1H), 7.08 (d, J=2.6 Hz, 1H), 6.83 (d, J=8.5 Hz, 1H), 4.38 (d, J=5.9 Hz, 2H), 1.23 (s, 9H).

Example 3

N-[(5-Chloro-2-hydroxy-phenyl)methyl]-4-(2,2-dimethylpropanoylamino)pyridine-2-carboxamide

Step 1: 4-Amino-N-[(5-chloro-2-methoxy-phenyl)methyl]pyridine-2-carboxamide

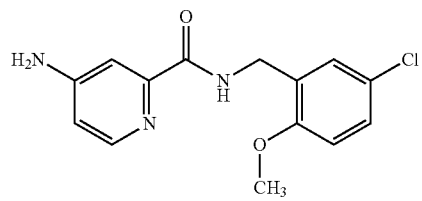 [SMILES: COc1ccc(Cl)cc1CNC(=O)c1cc(N)ccn1]

A mixture of (5-chloro-2-methoxy-phenyl)methanamine (0.34 mL, 2.72 mmol) and 4-aminopyridine-2-carboxylic acid (250 mg, 1.81 mmol) in DMF (5 mL) was treated with DIPEA (0.63 mL, 3.62 mmol) followed by HATU (1.03 g, 2.72 mmol) and stirred at room temperature for 16 hours. The resulting mixture was diluted with EtOAc (25 mL) and water (25 mL) and the phases separated. The organic portion was washed with water (2×25 mL), brine (25 mL), dried over Na₂SO₄ and concentrated in vacuo. Purification of the crude residue by chromatography on silica (Biotage® SNAP KP-NH) eluting with 0-100% EtOAc in heptanes afforded the title compound as a yellow oil, LC-MS (Method C): Rt 0.89 min; MS m/z 292.0/294.0= [M+H]+ (89%@215 nm)

1H NMR (500 MHz, DMSO-d6) δ 8.95 (t, J=6.4 Hz, 1H), 8.04 (d, J=5.5 Hz, 1H), 7.27 (dd, J=8.7, 2.7 Hz, 1H), 7.22 (d, J=2.3 Hz, 1H), 7.07 (d, J=2.7 Hz, 1H), 7.02 (d, J=8.8 Hz, 1H), 6.61 (dd, J=5.6, 2.4 Hz, 1H), 6.33 (s, 2H), 4.39 (d, J=6.4 Hz, 2H), 3.83 (s, 3H).

Step 2: N-[(5-Chloro-2-methoxy-phenyl)methyl]-4-(2,2-dimethylpropanoylamino)pyridine-2-carboxamide

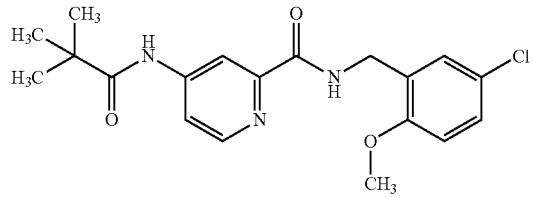 [SMILES: COc1ccc(Cl)cc1CNC(=O)c1cc(NC(=O)C(C)(C)C)ccn1]

A cooled (0° C.) mixture of 4-amino-N-[(5-chloro-2-methoxy-phenyl)methyl]pyridine-2-carboxamide (step 1) (89%, 58 mg, 0.18 mmol) and DIPEA (47 μL, 0.27 mmol) in DCM (4 mL) was treated with a solution of pivaloyl chloride (26 μL, 0.21 mmol) in DCM (1 mL). The mixture was allowed to warm to room temperature and stirred for 24 h. Additional DIPEA (47 μL, 0.27 mmol) was added followed by a solution of pivaloyl chloride (26 μL, 0.21 mmol) in DCM (1 mL). The resulting mixture was stirred for a further 6 hours and then allowed to stand at room temperature for 2 days. The mixture was concentrated in vacuo and purification of the crude residue by chromatography on silica eluting with 0-80% EtOAc in heptanes afforded the title compound as a yellow film.

LC-MS (Method C): Rt 1.23 min; MS m/z 376.1, 378.1=[M+H]+ (95%@215 nm)

1H NMR (500 MHz, DMSO-d6) δ 9.80 (s, 1H), 9.14 (t, J=6.4 Hz, 1H), 8.51 (d, J=5.5 Hz, 1H), 8.34 (d, J=2.1 Hz, 1H), 8.01 (dd, J=5.6, 2.2 Hz, 1H), 7.28 (dd, J=8.7, 2.7 Hz, 1H), 7.09 (d, J=2.7 Hz, 1H), 7.03 (d, J=8.8 Hz, 1H), 4.44 (d, J=6.3 Hz, 2H), 3.84 (s, 3H), 1.24 (s, 9H).

Step 3: N-[(5-Chloro-2-hydroxy-phenyl)methyl]-4-(2,2-dimethylpropanoylamino)pyridine-2-carboxamide The title compound was prepared from N-[(5-chloro-2-methoxy-phenyl)methyl]-4-(2,2-dimethylpropanoylamino)pyridine-2-carboxamide (step 2) and 1M BBr3 in DCM analogously to Example 1 step 4.

LC-MS (Method A): Rt 3.28 min; MS m/z 362.2, 364.2=[M+H]+ (100%@215 nm) 1H NMR (500 MHz, DMSO-d6) δ 9.99 (s, 1H), 9.81 (s, 1H), 9.14 (t, J=6.4 Hz, 1H), 8.50 (d, J=5.6 Hz, 1H), 8.34 (d, J=2.1 Hz, 1H), 8.01 (dd, J=5.6, 2.2 Hz, 1H), 7.11 (dd, J=8.5, 2.7 Hz, 1H), 7.07 (d, J=2.7 Hz, 1H), 6.83 (d, J=8.5 Hz, 1H), 4.42 (d, J=6.3 Hz, 2H), 1.24 (s, 9H).

Example 4

N2-tert-Butyl-N4-[(2-hydroxyphenyl)methyl]pyridine-2,4-dicarboxamide

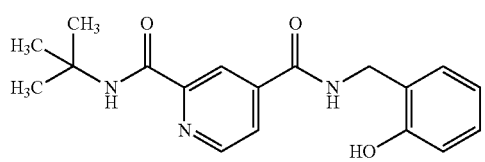 [SMILES: CC(C)(C)NC(=O)c1cc(C(=O)NCc2ccccc2O)ccn1]

Step 1: Methyl 4-[(2-methoxyphenyl)methylcarbamoyl]pyridine-2-carboxylate

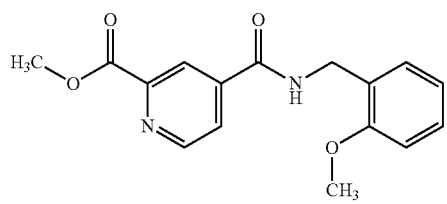 [SMILES: COC(=O)c1cc(C(=O)NCc2ccccc2OC)ccn1]

The title compound was prepared from 2-methoxycarbonylpyridine-4-carboxylic acid and (2-methoxyphenyl)methanamine analogously to Example 3 step 1.

LC-MS (Method C): Rt 1.01 min; MS m/z 301.1=[M+H]+ (97%@215 nm)

1H NMR (500 MHz, DMSO-d6) δ 9.34 (t, J=5.7 Hz, 1H), 8.87 (dd, J=4.9, 0.7 Hz, 1H), 8.48 (dd, J=1.7, 0.8 Hz, 1H), 8.06 (dd, J=5.0, 1.7 Hz, 1H), 7.26 (td, J=8.2, 1.7 Hz, 1H), 7.21 (dd, J=7.5, 1.5 Hz, 1H), 7.01 (dd, J=8.2, 0.7 Hz, 1H), 6.91 (td, J=7.4, 1.0 Hz, 1H), 4.48 (d, J=5.8 Hz, 2H), 3.92 (s, 3H), 3.83 (s, 3H).

Step 2: 4-[(2-Methoxyphenyl)methylcarbamoyl]pyridine-2-carboxylic acid

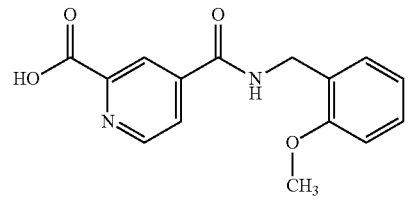 [SMILES: COc1ccccc1CNC(=O)c1ccnc(C(=O)O)c1]

1M LiOH (0.85 mL, 0.85 mmol) was added to a mixture of methyl 4-[(2-methoxyphenyl)methylcarbamoyl]pyridine-2-carboxylate (step 1) (97%, 220 mg, 0.71 mmol) in THF (2 mL) and water (1 mL). After stirring at room temperature for 1 hour, the mixture was acidified to pH 1 using 1M HCl and diluted with EtOAc (15 ml) and water (15 ml). The phases were separated and the organic layer was washed with brine (15 ml), dried over Na2SO4 and concentrated in vacuo to afford the title compound as a beige foamy solid.

LC-MS (Method C): Rt 0.89 min; MS m/z 287.0=[M+H]+ (98%@215 nm)

1H NMR (500 MHz, DMSO-d6) δ 9.32 (t, J=5.8 Hz, 1H), 8.85 (d, J=4.9 Hz, 1H), 8.50-8.45 (m, 1H), 8.02 (dd, J=5.0, 1.7 Hz, 1H), 7.28-7.23 (m, 1H), 7.22-7.19 (m, 1H), 7.01 (d, J=7.8 Hz, 1H), 6.91 (td, J=7.4, 0.9 Hz, 1H), 4.47 (d, J=5.8 Hz, 2H), 3.83 (s, 3H).

Step 3: N2-tert-Butyl-N4-[(2-methoxyphenyl)methyl]pyridine-2,4-dicarboxamide

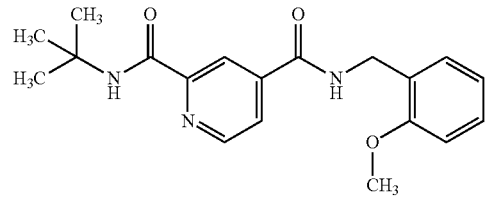 [SMILES: COc1ccccc1CNC(=O)c1ccnc(C(=O)NC(C)(C)C)c1]

TEA (0.18 mL, 1.03 mmol) was added to a mixture of 4-[(2-methoxyphenyl)methylcarbamoyl]pyridine-2-carboxylic acid (step 2) (98%, 100 mg, 0.34 mmol) and TBTU (131.9 mg, 0.41 mmol) in DMF (2 mL). The resulting mixture was stirred for 5 min then treated with 2-methylpropan-2-amine (0.04 mL, 0.41 mmol) and stirring continued at room temperature for 1 hour. The resulting mixture was diluted with EtOAc (20 ml) and water (20 ml) and the phases separated. The organic portion was washed with water (2×20 ml), brine (20 ml), dried over Na2SO4 and concentrated in vacuo to yield a yellow oil. Purification of the crude product by chromatography on silica eluting with 0-60% EtOAc in heptanes afforded the title compound as a thick yellow gum.

LC-MS (Method C): Rt 1.18 min; MS m/z 342.1=[M+H]+ (100%@215 nm)

1H NMR (500 MHz, DMSO-d6) δ 9.33 (t, J=5.7 Hz, 1H), 8.76 (d, J=4.9 Hz, 1H), 8.49-8.44 (m, 1H), 8.08 (s, 1H), 7.98 (dd, J=5.0, 1.7 Hz, 1H), 7.26 (dd, J=7.6, 1.6 Hz, 1H), 7.20 (dd, J=7.5, 1.3 Hz, 1H), 7.01 (d, J=7.8 Hz, 1H), 6.91 (dd, J=7.4, 0.7 Hz, 1H), 4.47 (d, J=5.8 Hz, 2H), 3.83 (s, 3H), 1.43 (s, 9H).

Step 4: N2-tert-Butyl-N4-[(2-hydroxyphenyl)methyl]pyridine-2,4-dicarboxamide The title compound was prepared from N2-tert-butyl-N4-[(2-methoxyphenyl)methyl]pyridine-2,4-dicarboxamide (step 3) and 1M BBr3 in DCM analogously to Example 1 step 4.

LC-MS (Method A): Rt 2.94 min; MS m/z 328.1=[M+H]+ (100%@215 nm)

1H NMR (500 MHz, DMSO-d6) δ 9.56 (s, 1H), 9.35 (t, J=5.8 Hz, 1H), 8.76 (dd, J=5.0, 0.7 Hz, 1H), 8.46 (dd, J=1.7, 0.7 Hz, 1H), 8.08 (s, 1H), 7.98 (dd, J=5.0, 1.8 Hz, 1H), 7.14 (dd, J=7.5, 1.4 Hz, 1H), 7.08 (td, J=7.9, 1.7 Hz, 1H), 6.82 (dd, J=8.0, 1.0 Hz, 1H), 6.76 (td, J=7.4, 1.1 Hz, 1H), 4.44 (d, J=5.8 Hz, 2H), 1.42 (s, 9H).

Example 5

N1-tert-Butyl-N3-[(2-hydroxyphenyl)methyl]benzene-1,3-dicarboxamide

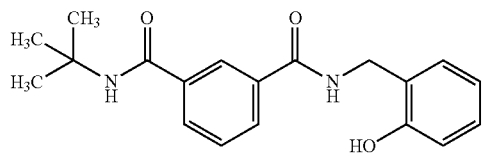 [SMILES: CC(C)(C)NC(=O)c1cccc(C(=O)NCc2ccccc2O)c1]

Step 1: Methyl 3-(tert-butylcarbamoyl)benzoate

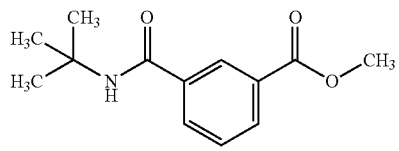 [SMILES: COC(=O)c1cccc(C(=O)NC(C)(C)C)c1]

The title compound was prepared from 3-methoxycarbonylbenzoic acid and 2-methylpropan-2-amine analogously to Example 1 step 3.

LC-MS (Method C): Rt 1.09 min; MS m/z 236.1=[M+H]+ (64%@215 nm)

1H NMR (500 MHz, Chloroform-d) δ 8.30 (t, J=1.7 Hz, 1H), 8.13 (dt, J=7.8, 1.3 Hz, 1H), 7.99 (dt, J=7.8, 1.4 Hz, 1H), 7.51 (t, J=7.8 Hz, 1H), 6.01 (s, 1H), 3.94 (s, 3H), 1.48 (s, 9H).

Step 2: 3-(tert-Butylcarbamoyl)benzoic acid

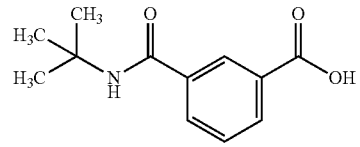 [SMILES: CC(C)(C)NC(=O)c1cccc(C(=O)O)c1]

To a solution of methyl 3-(tert-butylcarbamoyl)benzoate (step 1) (219 mg, 0.93 mmol) in 1,4-dioxane (3 mL) was added 2M LiOH (0.93 mL, 1.86 mmol) and the mixture was shaken at room temperature for 80 min. The solvent was removed in vacuo and the residue was acidified to pH1 with 1M HCl (2 mL). The mixture was extracted with DCM (2×5 mL) and the organic extracts were passed through a hydrophobic frit. The filtrate was concentrated in vacuo to afford the title compound as a white solid.

LC-MS (Method C): Rt 0.93 min; MS m/z 222.2=[M+H]+ (97%@215 nm)

1H NMR (500 MHz, Methylene Chloride-d2) δ 8.33 (t, J=1.6 Hz, 1H), 8.06-7.96 (m, 3H), 7.55 (t, J=7.7 Hz, 1H), 1.39 (s, 9H).

Step 3: N1-tert-Butyl-N3-[(2-hydroxyphenyl)methyl]benzene-1,3-dicarboxamide

To a solution of 3-(tert-butylcarbamoyl)benzoic acid (step 2) (70 mg, 0.32 mmol) and 2-(aminomethyl)phenol (0.13 mL, 0.35 mmol) in DCM (5 mL) was added DIPEA (0.06 mL, 0.32 mmol) followed by HATU (120.3 mg, 0.32 mmol) and the mixture was shaken at room temperature overnight. The resulting mixture was washed with water (3 mL) and passed through a hydrophobic frit. The filtrate was concentrated in vacuo to afford the title compound as an off white solid, LC-MS (Method A): Rt 2.79 min; MS m/z 327.2=[M+H]+ (95%@215 nm)

1H NMR (500 MHz, Chloroform-d) δ 8.10 (d, J=1.6 Hz, 1H), 7.88 (d, J=7.8 Hz, 1H), 7.83 (d, J=7.8 Hz, 1H), 7.46 (t, J=7.8 Hz, 1H), 7.23 (td, J=8.1, 1.7 Hz, 1H), 7.20-7.13 (m, 2H), 6.97 (dd, J=8.1, 1.0 Hz, 1H), 6.85 (td, J=7.4, 1.1 Hz, 1H), 6.06 (s, 1H), 4.56 (d, J=6.5 Hz, 2H), 1.47 (s, 9H).

Example 6

N-[3-[[2-(5-Chloro-2-hydroxy-phenyl)acetyl]amino]phenyl]-2,2-dimethyl-propanamide

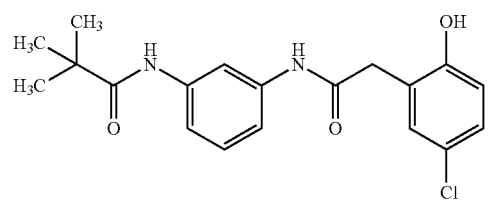 [SMILES: CC(C)(C)C(=O)Nc1cccc(NC(=O)Cc2cc(Cl)ccc2O)c1]

Step 1: N-(3-Aminophenyl)-2,2-dimethyl-propanamide

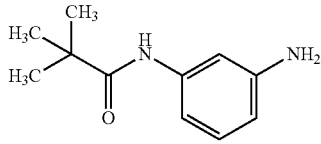

A cooled (0° C.) solution of benzene-1,3-diamine (1.0 g, 9.25 mmol) in DCM (5 mL) was treated with DIPEA (4.85 mL, 27.74 mmol) and 2,2-dimethylpropanoyl 2,2-dimethyl-propanoate (2.06 mL, 10.17 mmol) and stirred at 0° C. for 2 h. The resulting mixture was allowed to warm to room temperature and stirred for 20 h. The mixture was diluted with water (12.5 mL), saturated NaHCO$_3$ (25 mL) and DCM (30 mL) and passed through a hydrophobic frit. The organic portion was further washed with saturated brine (25 mL) and collected using a hydrophobic frit. Purification of the crude product by chromatography on silica eluting with 25-100% EtOAc in heptanes afforded the title compound as a light red brown solid.

LC-MS (Method C): Rt 0.69 min; MS m/z 193=[M+H]+ (100%@215 nm) 1H NMR (500 MHz, DMSO-d6) δ 8.84 (s, 1H), 6.93 (t, J=2.1 Hz, 1H), 6.88 (t, J=7.9 Hz, 1H), 6.71 (ddd, J=8.0, 1.9, 0.9 Hz, 1H), 6.24 (ddd, J=7.9, 2.2, 0.9 Hz, 1H), 4.97 (s, 2H), 1.19 (s, 9H).

Step 2: N-[3-[[2-(5-Chloro-2-hydroxy-phenyl)acetyl]amino]phenyl]-2,2-dimethyl-propanamide A solution of N-(3-aminophenyl)-2,2-dimethyl-propanamide (step 1) (48 mg, 0.25 mmol) and 5-chloro-3H-benzofuran-2-one (prepared according to the literature procedure of Journal of Fluorine Chemistry 99 (1999) 189-195) (40 mg, 0.24 mmol) in toluene (2 mL) was stirred at 120° C. for 2 h. The resulting mixture was concentrated in vacuo and purification of the residue by preparative HPLC (acidic pH, early elution method) afforded the title compound as an off-white powder.

LC-MS (Method A): Rt 3.24 min; MS m/z 361/363=[M+H]+ (98%@215 nm)

1H NMR (500 MHz, DMSO-d6) δ 10.04 (s, 1H), 9.80 (s, 1H), 9.18 (s, 1H), 7.97 (t, J=1.9 Hz, 1H), 7.30-7.24 (m, 2H), 7.21-7.14 (m, 2H), 7.10 (dd, J=8.6, 2.7 Hz, 1H), 6.80 (d, J=8.6 Hz, 1H), 3.59 (s, 2H), 1.21 (s, 9H).

Example 7

N-[4-[[2-(5-Chloro-2-hydroxy-phenyl)acetyl]amino]-2-pyridyl]-2,2-dimethyl-propanamide

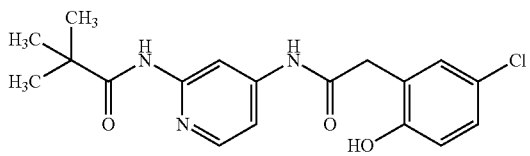 [SMILES: CC(C)(C)C(=O)Nc1cc(NC(=O)Cc2cc(Cl)ccc2O)ccn1]

Step 1: 2-(5-Chloro-2-methoxy-phenyl)-N-(2-chloro-4-pyridyl)acetamide

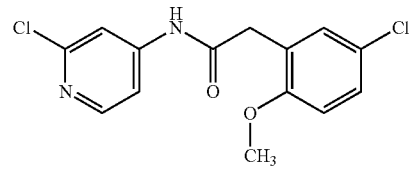 [SMILES: COc1ccc(Cl)cc1CC(=O)Nc1ccnc(Cl)c1]

The title compound was prepared from 2-(5-chloro-2-methoxy-phenyl)acetic acid and 2-chloropyridin-4-amine analogously to Example 1.2 step 1.

LC-MS (Method C): Rt 1.12 min; MS m/z 311.1=[M+H]+ (100%@215 nm)

1H NMR (500 MHz, Chloroform-d) δ 8.23 (d, J=5.6 Hz, 1H), 7.91 (s, 1H), 7.49 (d, J=1.7 Hz, 1H), 7.32-7.27 (m, 3H), 6.91 (d, J=8.7 Hz, 1H), 3.95 (s, 3H), 3.69 (s, 2H).

Step 2: N-[4-[[2-(5-Chloro-2-methoxy-phenyl)acetyl]amino]-2-pyridyl]-2,2-dimethyl-propanamide

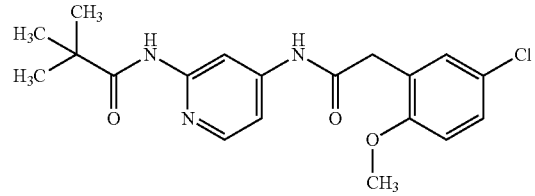 [SMILES: COc1ccc(Cl)cc1CC(=O)Nc1ccnc(NC(=O)C(C)(C)C)c1]

A suspension of 2-(5-chloro-2-methoxy-phenyl)-N-(2-chloro-4-pyridyl)acetamide (step 1) (100%, 50 mg, 0.16 mmol), 2,2-dimethylpropanamide (33 mg, 0.32 mmol) and potassium carbonate (44 mg, 0.32 mmol) in 1,4-dioxane (1 mL) and DMF (0.2 mL) was degassed with N$_2$ for 5 min. XantPhos Pd-G3 (15 mg, 0.02 mmol) added and the sealed tube was heated to 120° C. using microwave radiation for 45 min followed by 130° C. for 30 min. The resulting mixture was concentrated in vacuo and purification of the crude residue by chromatography on silica eluting with EtOAc in heptanes afforded the title compound as a colourless glass.

LC-MS (Method C): Rt 1.06 min; MS m/z 376.0=[M+H]+ (54%@215 nm)

1H NMR (500 MHz, Chloroform-d) δ 8.16 (d, J=6.1 Hz, 1H), 7.90 (t, J=6.4 Hz, 2H), 7.29-7.27 (m, 1H), 7.24 (d, J=2.5 Hz, 1H), 6.89 (d, J=8.8 Hz, 1H), 3.95 (s, 3H), 3.81 (s, 2H), 1.39 (s, 9H).

Step 3: N-[4-[[2-(5-Chloro-2-hydroxy-phenyl)acetyl]amino]-2-pyridyl]-2,2-dimethyl-propanamide The title compound was prepared from N-[4-[[2-(5-chloro-2-methoxy-phenyl)acetyl]amino]-2-pyridyl]-2,2-dimethyl-propanamide (step 2) and 1M BBr$_3$ in DCM analogously to Example 1 step 4.

LC-MS (Method A): Rt 2.17 min; MS m/z 362.1=[M+H]+ (100%@215 nm)

1H NMR (500 MHz, Methanol-d4) δ 8.25 (d, J=1.8 Hz, 1H), 8.15 (d, J=6.3 Hz, 1H), 7.50 (dd, J=6.3, 2.0 Hz, 1H), 7.18 (d, J=2.6 Hz, 1H), 7.09 (dd, J=8.6, 2.6 Hz, 1H), 6.78 (d, J=8.6 Hz, 1H), 3.73 (s, 2H), 1.32 (s, 9H).

Example 7.1

N-[4-[[2-(5-Chloro-2-hydroxy-phenyl)acetyl]amino]-2-pyridyl]cyclohexane carboxamide

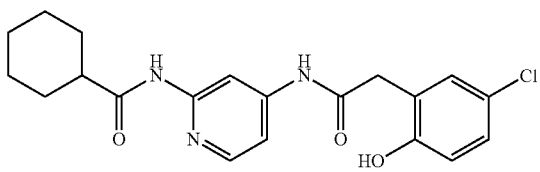 [SMILES: O=C(Cc1cc(Cl)ccc1O)Nc1ccnc(NC(=O)C2CCCCC2)c1]

The title compound was prepared from 2-(5-chloro-2-methoxy-phenyl)-N-(2-chloro-4-pyridyl)acetamide (Example 7 step 1) and cyclohexanecarboxamide analogously to Example 7 step 2 and 3.

LC-MS (Method A): Rt 2.51 min; MS m/z 388.3=[M+H]+ (99%@215 nm)

1H NMR (500 MHz, Methanol-d4) δ 8.14 (d, J=6.7 Hz, 1H), 8.11 (d, J=2.0 Hz, 1H), 7.43 (dd, J=6.7, 2.0 Hz, 1H), 7.18 (d, J=2.6 Hz, 1H), 7.10 (dd, J=8.6, 2.6 Hz, 1H), 6.78 (d, J=8.6 Hz, 1H), 3.75 (s, 2H), 2.47 (tt, J=11.6, 3.5 Hz, 1H), 1.97-1.89 (m, 2H), 1.85 (dt, J=12.5, 3.1 Hz, 2H), 1.73 (d, J=12.5 Hz, 1H), 1.53 (qd, J=12.5, 3.1 Hz, 2H), 1.43-1.22 (m, 3H).

Example 8

5-[[2-(4-tert-Butyl-2-fluoro-5-hydroxy-phenyl)acetyl]amino]-N-(1-cyano-1-methyl-ethyl)thiophene-2-carboxamide

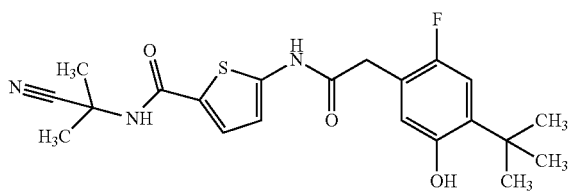 [SMILES: CC(C)(C#N)NC(=O)c1ccc(NC(=O)Cc2cc(O)c(C(C)(C)C)cc2F)s1]

Step 1:
2-(4-tert-Butyl-2-fluoro-5-methoxy-phenyl)acetic acid

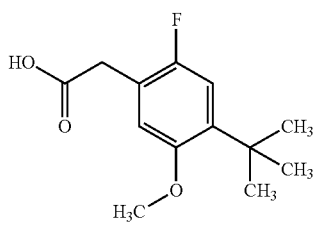

A solution of 2-(2-fluoro-5-methoxy-phenyl)acetic acid (5.0 g, 27.15 mmol) in DCE (181.01 mL) was treated with tert-butanol (31.16 mL, 325.8 mmol) and concentrated sulfuric acid (17.37 mL, 325.8 mmol). After stirring for 1 h, additional tert-butanol (10.0 mL, 105 mmol) and concentrated sulfuric acid (5.8 mL, 109 mmol) were added and the mixture was stirred overnight. The resulting mixture was diluted with water (150 mL) and the phases were separated. The aqueous layer was extracted with DCM (3×150 mL). The combined organic extracts were washed with brine, dried over Na₂SO₄ and concentrated in vacuo. The residue was diluted with MeOH (100 mL) and treated with 2M HCl in MeOH (100 mL, freshly prepared from thionyl chloride) and the mixture was heated at reflux for 40 min. The resulting mixture was concentrated in vacuo and the residue was dissolved in DCM (150 mL), washing with saturated aqueous sodium bicarbonate solution (150 mL). The aqueous washes were further extracted with DCM (3×100 mL) and the combined organic extracts were dried over Na₂SO₄ and concentrated in vacuo. Purification by chromatography on silica eluting with 0-10% EtOAc in heptanes afforded the methyl ester intermediate. The material was dissolved in 1M LiOH (80 mL) and THF (80 mL) and stirred for 1 h. The volatiles were removed in vacuo and the aqueous solution was acidified with HCl resulting in precipitation of a solid. The solid was washed with excess water and dried to afford the title compound as a pale-yellow solid.

LC-MS (Method C): Rt 1.16 min; no ionisation (98%@215 nm)

1H NMR (500 MHz, DMSO-d6) δ 6.93 (d, J=6.1 Hz, 1H), 6.92 (s, 1H), 3.77 (s, 3H), 3.54 (s, 2H), 1.31 (s, 9H).

Step 2:
2-(4-tert-Butyl-2-fluoro-5-hydroxy-phenyl)acetic acid

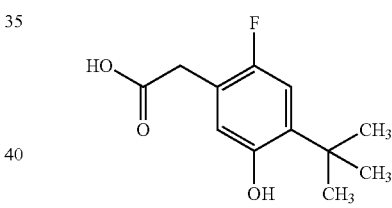

A cooled (0° C.) solution of 2-(4-tert-butyl-2-fluoro-5-methoxy-phenyl)acetic acid (step 1) (600 mg, 2.5 mmol) in DCM (12 mL) and treated with 1M BBr₃ in DCM (7.49 mL, 7.49 mmol) and the mixture was warmed to room temperature and stirred for 3 days. The resulting mixture was diluted with water (20 mL), stirred for 5 min then diluted with DCM (30 mL) and water (20 mL). The phases were separated and the aqueous further extracted with DCM (30 mL). The combined organic extracts were dried over Na₂SO₄ and concentrated in vacuo to give a brown oil. The oil was dissolved in THF (5 mL) and treated with 2M aqueous LiOH (2 mL), stirring at room temperature for 20 min. The resulting mixture was acidified to pH 1-2 by the dropwise addition of 1M HCl then diluted with EtOAc (40 mL) and water (30 mL). The phases were separated and the organic portion was washed with brine (30 mL), dried over Na₂SO₄ and concentrated in vacuo to afford the title compound as a brown oil LC-MS (Method C): Rt 1.07 min; no ionisation (97%@215 nm)

1H NMR (500 MHz, DMSO-d6) δ 12.30 (s (br), 1H), 9.27 (s, 1H), 6.85 (d, J=11.9 Hz, 1H), 6.67 (d, J=7.0 Hz, 1H), 3.45 (s, 2H), 1.32 (s, 9H).

Step 3: Methyl 5-[[2-(4-tert-butyl-2-fluoro-5-hydroxy-phenyl)acetyl]amino]thiophene-2-carboxylate

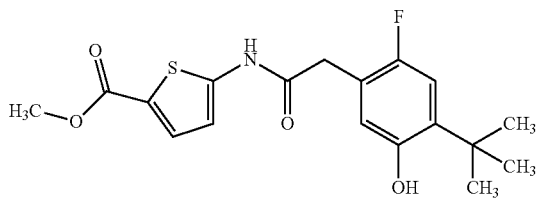 [SMILES: COC(=O)c1ccc(NC(=O)Cc2cc(O)c(C(C)(C)C)cc2F)s1]

To a solution of methyl 5-aminothiophene-2-carboxylate (219 mg, 1.39 mmol), 2-(4-tert-butyl-2-fluoro-5-hydroxy-phenyl)acetic acid (step 2)(75%, 350 mg, 1.16 mmol) and DIPEA (0.26 mL, 1.51 mmol) in DMF (4 mL) was added HATU (485 mg, 1.28 mmol) and the mixture was stirred at room temperature for 4 h. The resulting mixture was diluted with EtOAc (30 mL) and water (30 mL) and the phases were separated. The organic portion was washed with water (30 mL), brine (30 mL), dried over $Na_2SO_4$ and concentrated in vacuo. Purification of the crude material by chromatography on silica eluting with 0-100% EtOAc in heptanes afforded the title compound as a orange solid.

LC-MS (Method C): Rt 1.21 min; MS m/z 366.1=[M+H]+ (84%@215 nm)

1H NMR (400 MHz, DMSO-d6) δ 11.87 (s, 1H), 9.33 (s, 1H), 7.60 (d, J=4.2 Hz, 1H), 6.88 (d, J=11.9 Hz, 1H), 6.74-6.69 (m, 2H), 3.76 (s, 3H), 3.65 (s, 2H), 1.32 (s, 9H).

Step 4: 5-[[2-(4-tert-Butyl-2-fluoro-5-hydroxy-phenyl)acetyl]amino]thiophene-2-carboxylic acid

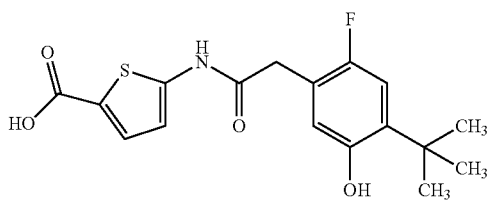 [SMILES: CC(C)(C)c1cc(F)c(CC(=O)Nc2ccc(C(=O)O)s2)cc1O]

2M LiOH (0.72 mL, 1.44 mmol) was added to a solution of methyl 5-[[2-(4-tert-butyl-2-fluoro-5-hydroxy-phenyl)acetyl]amino]thiophene-2-carboxylate (step 3) (84%, 314 mg, 0.72 mmol) in THF (2 mL) and water (2 mL) and the mixture was heated to 50° C. overnight. The resulting mixture was concentrated in vacuo to remove the majority of the THF and then acidified to pH 1-2 by the dropwise addition of 1M HCl. The mixture was partitioned between EtOAc (15 mL) and water (15 mL) and the phases were separated. The organic portion was washed with brine (15 mL), dried over $Na_2SO_4$ and concentrated in vacuo to afford the title compound as an orange oil.

LC-MS (Method C): Rt 1.11 min; MS m/z 352.0=[M+H]+ (98%@215 nm)

1H NMR (400 MHz, DMSO-d6) δ 11.78 (s, 1H), 9.33 (s, 1H), 7.52 (d, J=4.1 Hz, 1H), 6.87 (d, J=11.9 Hz, 1H), 6.73 (d, J=7.0 Hz, 1H), 6.70 (d, J=4.2 Hz, 1H), 3.64 (s, 2H), 1.32 (s, 9H).

Step 5: 5-[[2-(4-tert-Butyl-2-fluoro-5-hydroxy-phenyl)acetyl]amino]-N-(1-cyano-1-methyl-ethyl)thiophene-2-carboxamide HATU (133 mg, 0.35 mmol) was added to a solution of 5-[[2-(4-tert-butyl-2-fluoro-5-hydroxy-phenyl)acetyl]amino]thiophene-2-carboxylic acid (step 4) (70%, 175 mg, 0.35 mmol), 2-amino-2-methyl-propanenitrile hydrochloride (63 mg, 0.52 mmol) and DIPEA (0.15 mL, 0.87 mmol) in DMF (3 mL) and the mixture was stirred at room temperature overnight. The resulting mixture was partitioned between EtOAc (20 mL) and water (20 mL) and the phases were separated. The organic portion was washed with washed with brine (15 mL), dried over $Na_2SO_4$ and concentrated in vacuo. Purification of the crude material by preparative HPLC (acidic pH, standard elution method) afforded the title compound as an off-white solid.

LC-MS (Method A): Rt 3.30 min; MS m/z 418.2=[M+H]+ (99%@215 nm)

1H NMR (500 MHz, DMSO-d6) δ 11.69 (s, 1H), 9.33 (s, 1H), 8.49 (s, 1H), 7.65 (d, J=4.2 Hz, 1H), 6.87 (d, J=11.9 Hz, 1H), 6.74 (d, J=6.9 Hz, 1H), 6.68 (d, J=4.2 Hz, 1H), 3.64 (s, 2H), 1.66 (s, 6H), 1.32 (s, 9H).

Example 9

5-[[2-[2-Fluoro-5-hydroxy-4-(2-hydroxy-1,1-dimethyl-ethyl)phenyl]acetyl]amino]-N-[1-(trifluoromethyl)cyclopropyl]thiophene-2-carboxamide

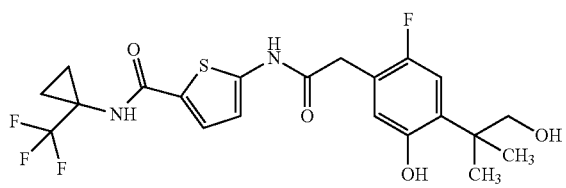 [SMILES: CC(C)(CO)c1cc(F)c(CC(=O)Nc2ccc(C(=O)NC3(C(F)(F)F)CC3)s2)cc1O]

Intermediate A: 2-(5-Fluoro-3,3-dimethyl-2-oxo-benzofuran-6-yl)acetic acid

Step A1: 2-(4-Bromo-2-fluoro-5-methoxy-phenyl)acetic acid

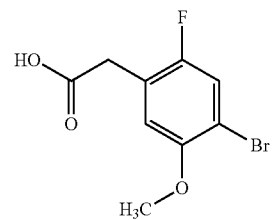

To a cooled (0° C.) solution of 2-(2-fluoro-5-methoxy-phenyl)acetic acid (45 g, 244.4 mmol) in MeCN (1.2 L) was added dropwise a solution of bromine (12.63 mL, 219.9 mmol) in MeCN (100 mL) over a period of 10 min. The resulting mixture was allowed to warm to room temperature gradually without removing the ice bath (~1.5 h). Additional bromine (4.21 mL, 73.3 mmol) in MeCN (50 mL) was added dropwise to the mixture at 0° C. which was stirred at room temperature for a further 3.5 h. Further bromine (4.21 mL, 73.3 mmol) in MeCN (50 mL) was added at room temperature and mixture was stirred at room temperature for 30 min. The reaction was quenched carefully with saturated aqueous sodium sulfite (~700 mL) until the bright orange colour had disappeared. The colourless solution was diluted with brine (200 mL) and EtOAc (200 mL), stirred vigorously for 10 min. The organic layer was separated and the aqueous layer was extracted further with EtOAc (200 mL). The organic layers were combined, dried over Na₂SO₄ and concentrated in vacuo to obtain the crude product as a white solid. The crude product was recrystallised by dissolving the solid in AcOH (700 mL), then treated with water (4 L). The mixture was stirred to mix the solvents whereupon crystals gradually appeared. The mixture was kept at room temperature for 1 h and then at 0° C. for 3 h. Filtration followed by vacuum drying at 40° C. afforded the title compound as a fluffy white solid.

LC-MS (Method C): Rt 1.07 min; (99%@215 nm)

¹H NMR (500 MHz, DMSO-d6) δ 12.55 (br s, 1H), 7.50 (d, J=8.9 Hz, 1H), 7.13 (d, J=6.6 Hz, 1H), 3.81 (s, 3H), 3.61 (d, J=1.3 Hz, 2H).

Step A2: Benzyl 2-(4-bromo-2-fluoro-5-methoxy-phenyl)acetate

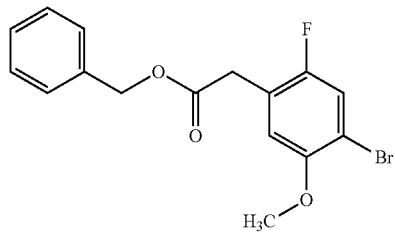 [SMILES: COc1cc(CC(=O)OCc2ccccc2)c(F)cc1Br]

A mixture of 2-(4-bromo-2-fluoro-5-methoxy-phenyl) acetic acid (step A1)(15 g, 57.02 mmol) and K₂CO₃ (15.76 g, 114.0 mmol) in DMF (140 mL) was treated with benzylbromide (7.45 mL, 62.7 mmol) and stirred at room temperature for 18 h. The resulting mixture was filtered and concentrated in vacuo. The residue was dissolved in EtOAc (300 mL) and sequentially washed with brine (200 mL) and saturated aqueous sodium bicarbonate (2×200 mL). The organic layer was dried over Na₂SO₄ and concentrated in vacuo. Purification by chromatography on silica eluting with 0-20% EtOAc in heptanes afforded the title compound as a colourless solid.

LC-MS (Method G): Rt 1.13 min; (95%@215 nm)

¹H NMR (500 MHz, DMSO-d6) δ 7.53 (d, J=8.9 Hz, 1H), 7.40-7.31 (m, 5H), 7.15 (d, J=6.6 Hz, 1H), 5.14 (s, 2H), 3.81-3.78 (m, 5H).

Step A3: Methyl 2-[4-(2-benzyloxy-2-oxo-ethyl)-5-fluoro-2-methoxy-phenyl]-2-methyl-propanoate

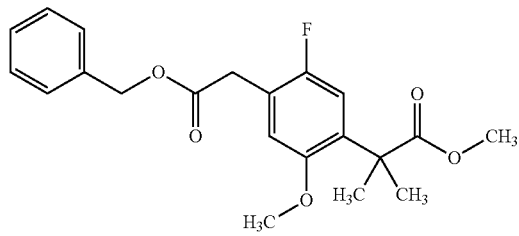 [SMILES: COC(=O)C(C)(C)c1cc(F)c(CC(=O)OCc2ccccc2)cc1OC]

Benzyl 2-(4-bromo-2-fluoro-5-methoxy-phenyl)acetate (step A2) (5.0 g, 14.16 mmol), ZnF₂ (1.1 g, 10.62 mmol) and Pd(PtBu₃)₂ (0.36 g, 0.71 mmol) were added to a reaction vessel and placed under a nitrogen atmosphere. A solution of (1-methoxy-2-methyl-prop-1-enoxy)-trimethyl-silane (5.75 mL, 28.31 mmol) in degassed DMF (50 mL) was added and the reaction mixture was heated to 80° C. for 18 h. The resulting mixture was filtered and concentrated in vacuo. The residue was dissolved in EtOAc (100 mL) and washed with brine (2×50 mL) and the organic layer was dried over Na₂SO₄ and concentrated in vacuo. Purification by chromatography on silica eluting with 0-30% EtOAc in heptanes the title compound as a pale yellow oil.

LC-MS (Method A): Rt 3.99 min; MS m/z 375.3=[M+H]+ (92%@215 nm)

¹H NMR (400 MHz, DMSO-d6) δ 7.40-7.30 (m, 5H), 7.09 (d, J=11.0 Hz, 1H), 6.98 (d, J=6.5 Hz, 1H), 5.14 (s, 2H), 3.76 (s, 2H), 3.66 (s, 3H), 3.53 (s, 3H), 1.40 (s, 6H).

Step A4: 2-(5-Fluoro-3,3-dimethyl-2-oxo-benzofuran-6-yl)acetic acid

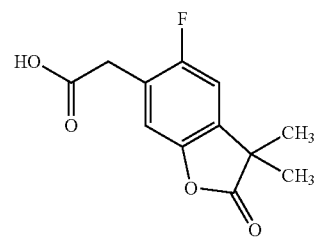 [SMILES: CC1(C)C(=O)Oc2cc(CC(=O)O)c(F)cc21]

1M BBr₃ in DCM (34.13 mL, 34.1 mmol) was added to a cooled (0° C.) mixture of methyl 2-[4-(2-benzyloxy-2-oxo-ethyl)-5-fluoro-2-methoxy-phenyl]-2-methyl-propanoate (step A3) (92%, 2777 mg, 6.83 mmol) in dry DCM (60 mL). The resulting mixture was allowed to warm to room temperature and stirred for 4.5 h. The reaction mixture was re-cooled to 0° C. and water (50 mL) was added. Stirring continued whilst gradually warming to room temperature over 30 min. The resulting mixture was diluted with DCM (80 mL) and water (80 mL) and the phases were separated. The aqueous portion was extracted with EtOAc (80 mL) then the combined organic extracts were dried over Na₂SO₄ and concentrated in vacuo to give the crude product as a brown oil. Purification of the crude product by C18 reverse phase chromatography eluting with 10-100% MeCN/water (+0.1% formic acid) afforded the title compound as a pale yellow solid.

LC-MS (Method H): Rt 1.19 min; (98%@215 nm)

¹H NMR (500 MHz, DMSO-d6) δ 12.56 (br. s, 1H), 7.42 (d, J=8.9 Hz, 1H), 7.25 (d, J=5.8 Hz, 1H), 3.64 (d, J=1.5 Hz, 2H), 1.44 (s, 6H).

Intermediate B: 5-Amino-N-[1-(trifluoromethyl)cyclopropyl]thiophene-2-carboxamide Step B1: 5-Nitro-N-[1-(trifluoromethyl)cyclopropyl]thiophene-2-carboxamide

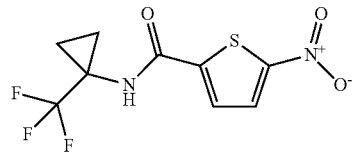 [SMILES: O=C(NC1(C(F)(F)F)CC1)c1ccc([N+](=O)[O-])s1]

To a mixture of 5-nitrothiophene-2-carboxylic acid (400 mg, 2.31 mmol) and HATU (1054 mg, 2.77 mmol) in DMF (10 mL) was added 1-(trifluoromethyl)cyclopropanamine hydrochloride (411 mg, 2.54 mmol) followed by DIPEA (0.97 mL, 5.54 mmol) and the reaction mixture was stirred at room temperature for 1 h. The resulting mixture was diluted with EtOAc (40 mL) and water (40 mL) and the phases were separated. The organic portion was washed with water (40 mL), brine (40 mL) then dried over $Na_2SO_4$ and concentrated in vacuo. Purification of the crude material by chromatography on silica eluting with 0-100% EtOAc in heptanes afforded the title compound as an off-white solid.

LC-MS (Method C): Rt 1.12 min; MS m/z 280.9=[M+H]+ (100%@215 nm)

1H NMR (400 MHz, DMSO-d6) δ 9.66 (s, 1H), 8.14 (d, J=4.4 Hz, 1H), 7.86 (d, J=4.4 Hz, 1H), 1.38-1.29 (m, 2H), 1.23-1.15 (m, 2H).

Step B2: 5-Amino-N-[1-(trifluoromethyl)cyclopropyl]thiophene-2-carboxamide

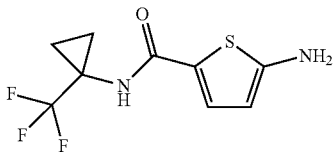 [SMILES: Nc1ccc(C(=O)NC2(C(F)(F)F)CC2)s1]

A mixture of 5-nitro-N-[1-(trifluoromethyl)cyclopropyl]thiophene-2-carboxamide (step B1) (596 mg, 2.13 mmol) in EtOH (20 mL) under a nitrogen atmosphere was treated with Pd on carbon (10%, 225 mg, 0.21 mmol) and placed under a hydrogen atmosphere. After stirring at room temperature for 2 h, the resulting mixture was filtered through Celite® (filter material) and washed with EtOH. The filtrate was concentrated in vacuo and purification of the crude product by chromatography on KP-NH silica eluting with EtOAc in heptanes afforded the title compound as a yellow oil.

LC-MS (Method G): Rt 0.67 min; MS m/z 251.1=[M+H]+ (97%@215 nm)

1H NMR (400 MHz, DMSO-d6) δ 8.55 (s, 1H), 7.38 (d, J=4.1 Hz, 1H), 6.34 (s, 2H), 5.81 (d, J=4.1 Hz, 1H), 1.27-1.23 (m, 2H), 1.10-1.05 (m, 2H).

Final Step: Intermediate A+Intermediate B

5-[[2-[2-Fluoro-5-hydroxy-4-(2-hydroxy-1,1-dimethyl-ethyl)phenyl]acetyl]amino]-N-[1-(trifluoromethyl)cyclopropyl]thiophene-2-carboxamide To a solution of 5-amino-N-[1-(trifluoromethyl)cyclopropyl]thiophene-2-carboxamide (Intermediate B) (80%, 134 mg, 0.43 mmol) and 2-(5-fluoro-3,3-dimethyl-2-oxo-benzofuran-6-yl)acetic acid (Intermediate A) (98%, 114 mg, 0.47 mmol) in DMF (3 mL) was added DIPEA (149 μL, 0.85 mmol) followed by 50% T3P® solution in EtOAc (0.38 mL, 0.64 mmol) and the reaction mixture was stirred at room temperature for 30 min. The resulting mixture was diluted with EtOAc (15 mL) and water (15 mL) and the phases were separated. The organic portion was washed with water (15 mL), brine (15 mL), dried over $Na_2SO_4$ and concentrated in vacuo to give the crude intermediate as a yellow/orange oil. The oil was dissolved in THF (3 mL) and cooled to −78° C. 4M LiBH4 in THF (107 μL, 0.43 mmol) was added dropwise and the resulting mixture was allowed to warm to room temperature, stirring for 1 h. The mixture was cooled to 0° C. and the reaction was quenched by the dropwise addition of 1M HCl (5 mL). The resulting mixture was diluted with EtOAc (20 mL) and water (15 mL) and the phases were separated. The aqueous portion was further extracted with EtOAc (20 mL) and the combined organic extracts were dried over $Na_2SO_4$ and concentrated in vacuo. Purification of the crude material by preparative HPLC (acidic pH, early elution method) afforded the title compound as a white solid.

LC-MS (Method A): Rt 2.76 min; MS m/z 475.3=[M+H]+ (100%@215 nm)

1H NMR (400 MHz, DMSO-d6) δ 11.65 (s, 1H), 9.38 (s, 1H), 8.95 (s, 1H), 7.61 (d, J=4.2 Hz, 1H), 6.89 (d, J=12.1 Hz, 1H), 6.71 (d, J=7.0 Hz, 1H), 6.65 (d, J=4.2 Hz, 1H), 4.77 (s, 1H), 3.63 (s, 2H), 3.60 (s, 2H), 1.31-1.22 (m, 8H), 1.15-1.08 (m, 2H).

Biological Example

Automated Whole-Cell Patch Clamp Assay to Detect TMEM16A Activity in Recombinant Cells Cell Culture and Preparation Fisher rat thyroid (FRT) cells stably expressing human TMEM16A (TMEM16Aabc variant; Dr Luis Galietta, Insituto Giannina, Italy) were cultured in T-75 flasks in Hams F-12 media with Coon's modification (Sigma) supplemented with 10% (v/v) foetal bovine serum, penicillin-streptomycin (10,000 U/mL/10000 μg/mL), G-418 (750 μg/mL), L-glutamine (2 mM) and sodium bicarbonate solution (7.5% v/v). At ~90% confluence cells were harvested for experiments by detachment with a 2:1 (v/v) mixture of Detachin (BMS Biotechnology) and 0.25% (w/v) trypsin-EDTA. Cells were diluted to a density of $3.5\text{-}4.5 \times 10^6$ cells/mL with media consisting of CHO-S-SFM II (Sigma), 25 mM HEPES (Sigma) and Soy bean trypsin inhibitor (Sigma).

Whole-Cell Patch Clamp Recording

FRT-TMEM16A cells were whole-cell patch clamped using an automated planar patch clamp system (Qpatch, Sophion). Briefly, once high resistance (GOhm) seals were established between the cells and the planar recording array the patch was ruptured using suction pulses to establish the whole-cell recording configuration of the patch clamp technique. The assay employed the following solutions (all reagents Sigma):

Intracellular solution (mM): N-methyl-D-glucamine 130, $CaCl_2$ 18.2, $MgCl_2$ 1, HEPES 10, EGTA 10, BAPTA 20, Mg-ATP 2, pH 7.25, 325mOsm with sucrose.

Extracellular solution (mM): N-methyl-D-glucamine 130, $CaCl_2$ 2, $MgCl_2$ 1, HEPES 10, pH 7.3, 320 mOsm with sucrose.

The intracellular solution buffers intracellular calcium at levels required to give ~20% activation of the maximal TMEM16A mediated current ($EC_{20}$ for calcium ions). Cells were voltage clamped at a holding potential of −70 mV and a combined voltage step (to +70 mV)/ramp (−90 my to +90 mV) was applied at 0.05 Hz. After a period of current stabilisation test compounds, solubilised in 100% (v/v) DMSO and subsequently diluted into extracellular solution, were applied to generate a cumulative concentration response curve. Each concentration of test compound was incubated for 5 minutes before addition of the next concentration. After the final concentration was tested a supramaximal concentration of either a known active positive modulator or the TMEM16A inhibitor, CaCCinhA01 (Del La Fuente et al, 2008) was added to define the upper and lower limits of the assay.

Compound activity was quantified by measuring the increase in current upon compound addition and expressing this as a percentage increase of baseline TMEM16A current level. Percentage increases in current were determined for each concentration and the data plotted as a function of concentration using either the Qpatch software or Graphpad Prism v6.05 providing the concentration which gave 50% of its maximal effect ($EC_{50}$) and maximum efficacy (percentage of baseline increase).

The method of calculating the results is illustrated in FIG. 1, which shows an example trace from the Qpatch TMEM16A assay. In FIG. 1, $I_{BL}$ equals baseline current, $I_{[\#1]}$ equals the peak current during test compound concentration 1 incubation period and so on.

Peak TMEM16A current at +70 mV was plotted as a function of time over the assay period. Baseline current ($I_{BL}$) was measured after a period of stabilisation. The increase in current for each compound addition was determined by taking the peak current during the incubation period and subtracting the current from the previous recording period and then expressing this as a percentage of the baseline current. For test compound concentration 1 in FIG. 1 this is:

$$(I_{[\#1]} - I_{BL}/I_{BL}) \times 100$$

For each additional concentration tested the increase in current was determined by subtracting the current from the previous incubation period and normalising the baseline value—for test concentration 2 in FIG. 1 this is:

$$(I_{[\#2]} - I_{[\#1]}/I_{BL}) \times 100$$

The values for each test concentration were plotted as a cumulative function of concentration e.g. for test concentration two this would be the sum of the peak changes measured during concentration one plus concentration two.

The results obtained for the example compounds are shown in Table 1, from which it can be seen that the compounds of the present invention are capable of significantly increasing the TMEM16A current level.

TABLE 1

% Potentiation shown by 3.33 µM solution of Test Compounds and Calculated $EC_{50}$ Values

| Example | % Potentiation @ 3.33 µM Avg | $EC_{50}$ Avg (µM) |
|---|---|---|
| 1 | 106.6 | 0.042 |
| 1.1 | 184.1 | 0.44 |
| 1.2 | 236.9 | 0.4 |
| 2 | 127.4 | |
| 3 | 81.3 | |
| 4 | 35.2 | |
| 5 | 41.2 | 2.909 |
| 6 | 68.1 | 0.992 |
| 7 | 156.1 | 0.615 |
| 7.1 | 120.3 | 1.113 |
| 8 | 134.2 | 0.085 |
| 9 | 134.4 | 0.098 |

REFERENCES

Accurso F J, Moss R B, Wilmott R W, Anbar R D, Schaberg A E, Durham T A, Ramsay B W; TIGER-1 Investigator Study Group (2011) Denufosol tetrasodium in patients with cystic fibrosis and normal to mildly impaired lung function. Am J Respir Crit Care Med, 183(5):627-634.

Boucher R C (2007) Evidence for airway surface dehydration as the initiating event in CF airway disease. J Intern Med., 261(1):5-16.

Caputo A, Caci E, Ferrera L, Pedemonte N, Barsanti C, Sondo E, Pfeffer U, Ravazzolo R, Zegarra-Moran O & Galietta L J (2008) TMEM16A, a membrane protein associated with calcium-dependent chloride channel activity. Science, 322(5901):590-594.

Del La Fuente R, Namkung W, Mills A & Verkman A S (2008) Small molecule screen identifies inhibitors of a human intestinal calcium-activated chloride channel. Mol Pharmacol, 73(3):758-768.

Kellerman D, Rossi Mospan A, Engels J, Schaberg A, Gorden J & Smiley L (2008) Denufosol: a review of studies with inhaled P2Y(2) agonists that led to Phase 2. Pulm Pharmacol Ther, 21(4):600-607.

Kunzelmann K & Mall M (2003) Pharmacotherapy of the ion transport defect in cystic fibrosis: role of purinergic receptor agonists and other potential therapeutics. Am J Respir Med, 2(4):299-309.

Matsui H, Grubb B R, Tarran R, Randell S H, Gatzy J T, Davis C W and Boucher R C (1998) Evidence for periciliary liquid layer depletion, not abnormal ion composition, in the pathogenesis of cystic fibrosis airways disease. Cell, 95(7):1005-15.

Moss R B (2013) Pitfalls of drug development: lessons learned from trials of denufosol in cystic fibrosis. J Pediatr, 162(4):676-680.

Pedemonte N & Galietta L J (2014) Structure and function of TMEM16 proteins (anoctamins). Physiol Rev, 94(2):419-459.

Pezzulo A A, Tang X X, Hoegger M J, Abou Alaiwa M H, Ramachandran S, Moninger T O, Karp P H, Wohlford-Lenan C L, Haagsman H P, van Eijk M, Banfi B, Horswill A R, Stoltz D A, McCray P B Jr, Welsh M J & Zabner J (2012) reduced airway surface pH impairs bacterial killing in the porcine cystic fibrosis lung. Nature, 487(7405):109-113.

Yang Y D, Cho H, Koo J Y, Tak M H, Cho Y, Shim W S, Park S P, Lee J, Lee B, Kim B M, Raouf R, Shin Y K & Oh U (2008) TMEM16 confers receptor-activated calcium-dependent chloride conductance. Nature, 455(7217):1210-1215.

The invention claimed is:

1. A compound of formula (I):

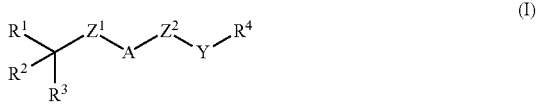

or a tautomer, a stereoisomer, an isotopic variant, a pharmaceutically acceptable salt, or solvate thereof, wherein A is

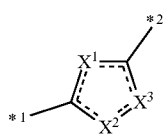

where
one of $X^1$, $X^2$, $X^3$ is S and the other two of $X^1$, $X^2$ and $X^3$ are CH;

=== represents a single or a double bond such that the ring A is aromatic;

*[1] indicates the point of attachment to $Z^1$ and *[2] indicates the point of attachment to $Z^2$;

each of $Z^1$ and $Z^2$ is independently selected from *—C(O)NH— and *—NHC(O)—, where * indicates the point of attachment to the ring A;

$R^1$ is H, CN, C(O)OR$^{12}$, $C_{1-3}$ alkyl, $C_{2-3}$ alkenyl or $C_{2-3}$ alkynyl, any of which alkyl, alkenyl or alkynyl groups are optionally substituted with one or more substituents, selected from fluoro, OR$^{12}$, N(R$^{12}$)$_2$, C(O)OR$^{12}$, C(O)N(R$^{12}$)$_2$, C(O)R$^{12}$ and N(R$^{13}$)C(O)R$^{12}$;

$R^2$ is H or $C_{1-6}$ alkyl optionally substituted with OR$^{12}$; and wherein each $R^{12}$ and $R^{13}$ is independently selected from H, $C_{1-6}$ alkyl and $C_{1-6}$ fluoroalkyl, $R^3$ is:
$C_{1-6}$ alkyl, $C_{2-6}$ alkenyl or $C_{2-6}$ alkynyl, any of which $C_{1-6}$ alkyl, $C_{2-6}$ alkenyl or $C_{2-6}$ alkynyl groups are optionally substituted with one or more substituents selected from fluoro, CN, R$^{14}$ OR$^{14}$, OR$^{15}$, N(R$^{15}$)$_2$, C(O)OR$^{15}$, C(O)N(R$^{15}$)$_2$, N(R$^{16}$)C(O)R$^{15}$, N(R$^{15}$)S(O)$_2$R$^{14}$, N(R$^{15}$)S(O)$_2$R$^{16}$ and N(R$^{15}$)C(O)OR$^{16}$; or $R^3$ is:
a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, OR$^{17}$ and N(R$^{17}$)$_2$;

wherein $R^{14}$ is a 6- to 10-membered aryl or 5- to 10-membered heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OR$^{17}$ and N(R$^{17}$)$_2$; wherein each R$^{17}$ is independently H, $C_{1-4}$ alkyl or $C_{1-4}$ haloalkyl;

wherein each R$^{15}$ and R$^{16}$ is independently H, $C_{1-6}$ alkyl or $C_{1-6}$ haloalkyl; or $R^2$ and $R^3$ together with the carbon atom to which they are attached combine to form a 3- to 10-membered carbocyclic or heterocyclic ring system optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$; or $R^1$, $R^2$ and $R^3$ together with the carbon atom to which they are attached combine to form a bridged 5- to 10-membered carbocyclic or heterocyclic ring system or phenyl, any of which carbocyclic or heterocyclic ring systems or phenyl groups are optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$; each R$^9$ is independently selected from H, $C_{1-6}$ alkyl or $C_{1-6}$ haloalkyl;

Y is —CH$_2$— or —CH(CH$_3$)—;

$R^4$ is a
6- to 14-membered aryl, 5- to 14-membered heteroaryl or a 5- to 10-membered carbocyclic ring system, any of which is optionally substituted with one or more substituents selected from: halo, CN, nitro, R$^{19}$, OR$^{19}$, OR$^6$, SR$^6$, NR$^6$R$^7$, C(O)R$^6$, C(O)R$^{19}$, C(O)OR$^6$, C(O)N(R$^6$)(R$^7$), N(R$^7$)C(O)R$^6$;

$C_{1-6}$ alkyl or O($C_{1-6}$ alkyl) either of which is optionally substituted with one or more substituents selected from halo, CN, nitro, R$^{19}$, OR$^6$, SR$^6$, NR$^6$R$^7$, C(O)R$^6$C(O)OR$^6$, C(O)N(R$^6$)(R$^7$) and N(R$^7$)C(O)R$^6$; and when $R^4$ is not fully aromatic in character, oxo;

wherein R$^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, O($C_{1-4}$ alkyl), O($C_{1-4}$ haloalkyl);

R$^6$ is H, $C_{1-6}$ alkyl, $C_{1-6}$ haloalkyl, benzyl, 3- to 7-membered carbocyclyl or 3- to 7-membered heterocyclyl;

R$^7$ is H, $C_{1-6}$ alkyl or $C_{1-6}$ haloalkyl; or

R$^6$ and R$^7$ together with the nitrogen atom to which they are attached form a 4 to 7-membered heterocyclic ring optionally containing one or more further heteroatoms and optionally substituted with one or more substituents selected from $C_{1-4}$ alkyl, oxo and halo.

2. The compound of claim 1 having formula (Ia), (Ib) or (Ic):

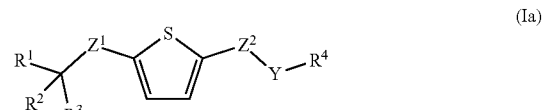

(Ia)

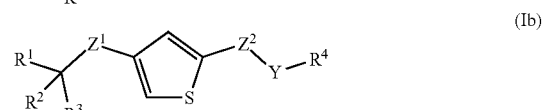

(Ib)

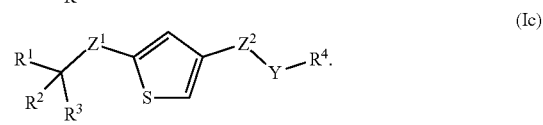

(Ic)

3. The compound according to claim 1, wherein Y is —CH$_2$—.

4. The compound according to claim 1, wherein:
R$^4$ is a 6- to 11-membered aryl group selected from phenyl, naphthyl, indanyl, 1,2,3,4-tetrahydronaphthyl and benzocycloheptanyl, any of which is unsubstituted or substituted as defined in claim 1; or R$^4$ is a 5- to 10-membered heteroaryl group selected from pyridyl, quinolinyl, quinoxalinyl, indazolyl, indolyl, benzoxazolyl, dihydrobenzofuranyl, furyl and thienyl, any of which is unsubstituted or substituted as defined in claim 1; or R$^4$ is a carbocyclyl group selected from cyclohexyl and adamantyl, any of which is unsubstituted or substituted as defined in claim 1.

5. The compound of claim 1 having formula (Ii):

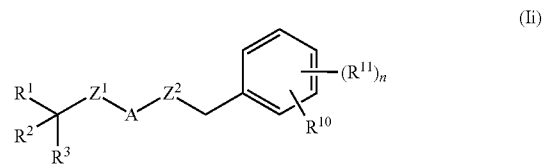

(Ii)

wherein
R$^{10}$ is H, OH, halo, C$_{1-6}$ alkyl, —O(C$_{1-6}$ alkyl);
each R$^{11}$ is independently H, halo, OH, CN, C$_{1-6}$ alkyl, C$_{1-6}$ haloalkyl, —O(C$_{1-6}$ alkyl) or C(O)O—(C$_{1-6}$ alkyl); and
n is 1 or 2; or
a compound of formula (Iii) or (Iiii):

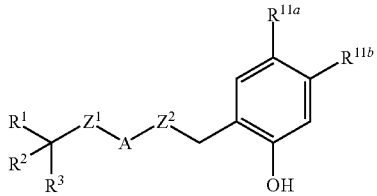
(Iii)

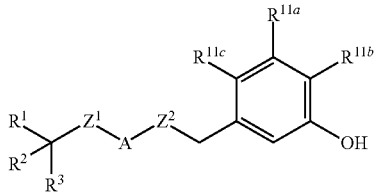
(Iiii)

wherein
R$^{11a}$ is H, halo, C$_{1-4}$ alkyl, C$_{1-4}$ haloalkyl or C(O)O(C$_{1-4}$ alkyl);
R$^{11b}$ is H, halo, C$_{1-4}$ alkyl or C$_{1-4}$ haloalkyl; and
R$^{11c}$ is H, halo, CN, C$_{1-4}$ alkyl or C$_{1-4}$ haloalkyl.

6. The compound of claim 5 having formula (Iai), (Ibi) or (Ici):

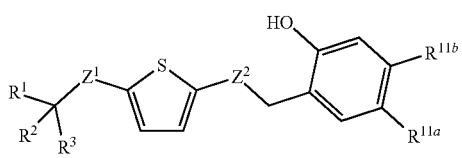
(Iai)

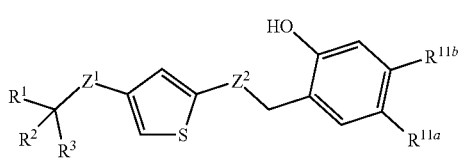
(Ibi)

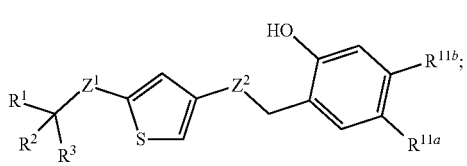
(Ici)

a compound of formula (Iaii), (Ibii) or (Icii):

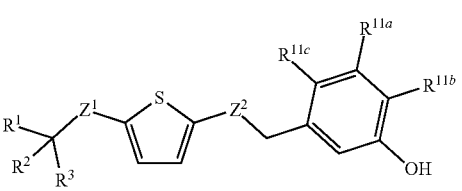
(Iaii)

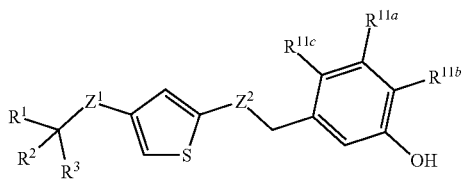
(Ibii)

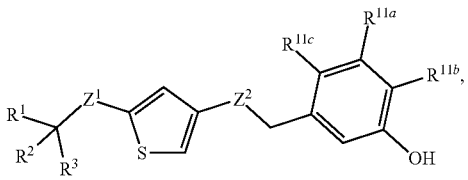
(Icii)

wherein R$^{11a}$, R$^{11b}$ and R$^{11c}$ are as defined in claim 5.

7. The compound according to claim 5, wherein:
the compound is a compound of formula (Iai), (Ibi), or (Ici), and either
R$^{11a}$ is H, halo, C$_{1-4}$ alkyl or C(O)O(C$_{1-4}$ alkyl) and R$^{11b}$ is H; or
both R$^{11a}$ and R$^{11b}$ are halo; or
the compound is a compound of formula (Iaii), (Ibii), or (Icii), and
R$^{11a}$ is H; and
R$^{11b}$ is C$_{1-4}$ alkyl, C$_{1-4}$ alkyl substituted with OH or C$_{1-4}$ haloalkyl; and
R$^{11c}$ is H, halo, methyl or ethyl.

8. A compound selected from:
N-tert-Butyl-5-[[2-(5-chloro-2-hydroxy-phenyl)acetyl]amino]thiophene-2-carboxamide (Compound 1);
N-tert-Butyl-5-[[2-(5-chloro-2-hydroxy-phenyl)acetyl]amino]thiophene-3-carboxamide (Compound 1.2);
N-tert-Butyl-4-[[2-(5-chloro-2-hydroxy-phenyl)acetyl]amino]thiophene-2-carboxamide (Compound 1.3);
5-[[2-(4-tert-Butyl-2-fluoro-5-hydroxy-phenyl)acetyl]amino]-N-(1-cyano-1-methyl-ethyl)thiophene-2-carboxamide (Compound 8);
5-[[2-[2-Fluoro-5-hydroxy-4-(2-hydroxy-1,1-dimethyl-ethyl)phenyl]acetyl]amino]-N-[1-(trifluoromethyl)cyclopropyl]thiophene-2-carboxamide (Compound 9); and
pharmaceutically acceptable salts and solvates thereof.

9. A pharmaceutical composition comprising an effective amount of a compound according to claim 1 and a pharmaceutically acceptable excipient.

10. A method for the treatment of diseases and conditions affected by modulation of TMEM16A, the method comprising administering to a patient in need of such treatment an effective amount of a compound according to claim 1, wherein the diseases and conditions affected by modulation of TMEM16A are selected from chronic obstructive pulmonary disease (COPD), chronic bronchitis, emphysema, bronchiectasis, asthma, primary ciliary dyskinesia, dry mouth (xerostomia), Sjorgen's syndrome, intestinal hypermobility, cholestasis and dry eyes.

11. The method of claim 10, wherein the diseases and conditions affected by modulation of TMEM16A are selected from chronic obstructive pulmonary disease (COPD), chronic bronchitis, emphysema, bronchiectasis, asthma, primary ciliary dyskinesia.

12. A process for the preparation of a compound according to claim 1 comprising:

(A) for compound of formula (I) in which $Z^1$ is *—C(O)NH—, $Z^2$ is *—NHC(O)— and A is:

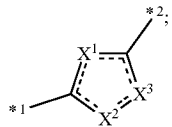

reacting a compound of formula (II):

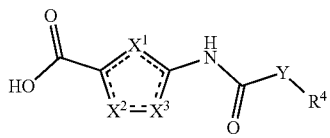

(II)

wherein $X^1$, $X^2$, $X^3$, Y and $R^4$ are as defined in claim 1;
with a compound of formula (III):

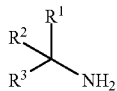

(III)

wherein $R^1$, $R^2$ and $R^3$ are as defined in formula (I);
in the presence of a coupling reagent and under basic conditions; or (B) for a compound of formula (I) in which $Z^1$ is *—NHC(O)— and $Z^2$ is *—C(O)NH—: reacting a compound of formula (X):

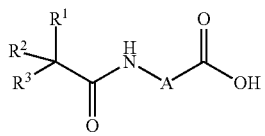

(X)

wherein $R^1$, $R^2$, $R^3$ and A are as defined in claim 1;
with a compound of formula (XI):

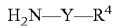

(XI)

wherein Y and $R^4$ are as defined in claim 1;
using a coupling agent under basic conditions; or (C) for a compound of general formula (I) in which $Z^1$ is *—NHC(O)— and $Z^2$ is *—C(O)NH—:
reacting a compound of formula (XV) as defined above with a compound of formula (XVI):

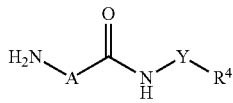

(XVI)

wherein A, Y and $R^4$ are as defined in claim 1;
under basic conditions; or (D) for a compound of formula (I) in which $Z^1$ is *—C(O)NH— and $Z^2$ is *—C(O)NH—: reacting a compound of formula (XX):

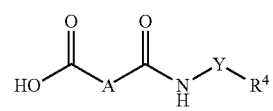

(XX)

wherein A, Y and $R^4$ are as defined in claim 1;
with a compound of formula (III) as defined above;
in the presence of a coupling agent under basic conditions; or (E) for a compound of formula (I) in which $Z^1$ is *—C(O)NH— and $Z^2$ is *—C(O)NH—:
reacting a compound of formula (XXV):

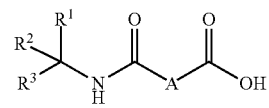

(XXV)

wherein $R^1$, $R^2$, $R^3$ and A are as defined in claim 1;
with a compound of formula (XI) as defined above;
in the presence of a coupling agent under basic conditions; or (F) for a compound of formula (I) in which $Z^1$ is *—NHC(O)— and $Z^2$ is *—NHC(O)—:
reacting a compound of formula (XXX):

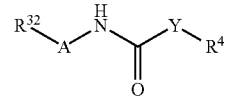

(XXX)

wherein A, Y and $R^4$ are as defined in claim 1 and $R^{32}$ is halo;
with a compound of formula (XXXI)

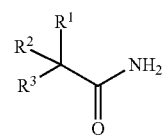

(XXXI)

wherein $R^1$, $R^2$ and $R^3$ are as defined in claim 1;
in the presence of a phosphorus ligand, a palladium catalyst and a base; or (G) for a compound of formula (I) in which $Z^1$ is *—NHC(O)—, $Z^2$ is *—NHC(O)—, Y is —CH$_2$— and $R^4$ is 2-hydroxy-5-chlorophenyl:

reacting a compound of formula (XXXV):

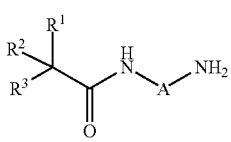

(XXXV)

wherein $R^1$, $R^2$, $R^3$ and A are as defined in claim 1;
with 5-chloro-3H-benzofuran-2-one, which has the structure:

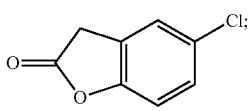

or
(H) converting a compound of formula (I) as defined in claim 1 in which either $R^3$; $R^1$, $R^2$ and $R^3$ together; or $R^4$ includes a phenyl group substituted with alkoxy to a compound of general formula (I) as defined in claim 1 in which either $R^3$; $R^1$, $R^2$ and $R^3$ together; or $R^4$ includes a phenyl group substituted with OH by treatment with boron tribromide.

13. A compound of formula (II), (X), (XVI), (XX), (XXV), (XXX) or (XXXV),

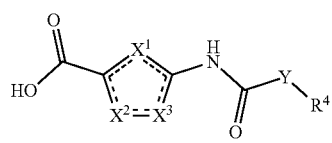

(II)

wherein
one of $X^1$, $X^2$, $X^3$ is S and the other two of $X^1$, $X^2$ and $X^3$ are CH;
Y is —$CH_2$— or —$CH(CH_3)$—;
$R^4$ is a
- 6- to 14-membered aryl, 5- to 14-membered heteroaryl or a 5- to 10-membered carbocyclic ring system, any of which is optionally substituted with one or more substituents selected from: halo, CN, nitro, $R^{19}$, $OR^{19}$, $OR^6$, $SR^6$, $NR^6R^7$, $C(O)R^6$, $C(O)R^{19}$, $C(O)OR^6$, $C(O)N(R^6)(R^7)$, $N(R^7)C(O)R^6$;
- $C_{1-6}$ alkyl or $O(C_{1-6}$ alkyl) either of which is optionally substituted with one or more substituents selected from halo, CN, nitro, $R^{19}$, $OR^6$, $SR^6$, $NR^6R^7$, $C(O)R^6C(O)OR^6$, $C(O)N(R^6)(R^7)$ and $N(R^7)C(O)R^6$, and
when $R^4$ is not fully aromatic in character, oxo;
wherein $R^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, $O(C_{1-4}$ alkyl), $O(C_{1-4}$ haloalkyl);
$R^6$ is H, $C_{1-6}$ alkyl, $C_{1-6}$ haloalkyl, benzyl, 3- to 7-membered carbocyclyl or 3- to 7-membered heterocyclyl;

$R^7$ is H, $C_{1-6}$ alkyl or $C_{1-6}$ haloalkyl; or
$R^6$ and $R^7$ together with the nitrogen atom to which they are attached form a 4 to 7-membered heterocyclic ring optionally containing one or more further heteroatoms and optionally substituted with one or more substituents selected from $C_{1-4}$ alkyl, oxo and halo;

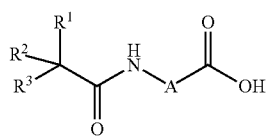

(X)

wherein
A is

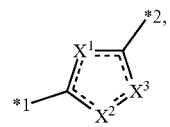

one of $X^1$, $X^2$, $X^3$ is S and the other two of $X^1$, $X^2$ and $X^3$ are CH;
=== represents a single or a double bond such that the ring A is aromatic;
*$^1$ indicates the point of attachment to

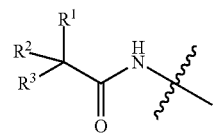

and *$^2$ indicates the point of attachment to

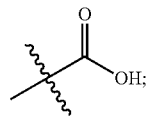 [SMILES: *C(=O)O]

$R^1$ is H, CN, $C(O)OR^{12}$, $C_{1-3}$ alkyl, $C_{2-3}$ alkenyl or $C_{2-3}$ alkynyl, any of which alkyl, alkenyl or alkynyl groups are optionally substituted with one or more substituents, selected from fluoro, $OR^{12}$, $N(R^{12})_2$, $C(O)OR^{12}$, $C(O)N(R^{12})_2$, $C(O)R^{12}$ and $N(R^{13})C(O)R^{12}$;
$R^2$ is H or $C_{1-6}$ alkyl optionally substituted with $OR^{12}$; and
wherein each $R^{12}$ and $R^{13}$ is independently selected from H, $C_{1-6}$ alkyl and $C_{1-6}$ fluoroalkyl,
$R^3$ is:
$C_{1-6}$ alkyl, $C_{2-6}$ alkenyl or $C_{2-6}$ alkynyl, any of which $C_{1-6}$ alkyl, $C_{2-6}$ alkenyl or $C_{2-6}$ alkynyl groups are optionally substituted with one or more substituents selected from fluoro, CN, $R^{14}$ $OR^{14}$, $OR^{15}$, $N(R^{15})_2$, $C(O)OR^{15}$, $C(O)N(R^{15})_2$, $N(R^{16})C(O)R^{15}$, $N(R^{15})S(O)_2R^{14}$, $N(R^{15})S(O)_2R^{16}$ and $N(R^{15})C(O)OR^{16}$; or $R^3$ is:
- a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, $OR^{17}$ and $N(R^{17})_2$;

wherein $R^{14}$ is a 6- to 10-membered aryl or 5- to 10-membered heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, $OR^{17}$ and $N(R^{17})_2$; wherein each $R^{17}$ is independently H, $C_{1-4}$ alkyl or $C_{1-4}$ haloalkyl;

wherein each $R^{15}$ and $R^{16}$ is independently H, $C_{1-6}$ alkyl or $C_{1-6}$ haloalkyl; or $R^2$ and $R^3$ together with the carbon atom to which they are attached combine to form a 3- to 10-membered carbocyclic or heterocyclic ring system optionally substituted with one or more substituents selected from halo, CN, $OR^9$, $N(R^9)_2$, $C(O)OR^9$, $C(O)N(R^9)_2$, $C(O)R^9$, $N(R)C(O)R^9$ and $C_{1-4}$ alkyl optionally substituted with halo, $OR^9$ or $N(R^9)_2$; or $R^1$, $R^2$ and $R^3$ together with the carbon atom to which they are attached combine to form a bridged 5- to 10-membered carbocyclic or heterocyclic ring system or phenyl, any of which carbocyclic or heterocyclic ring systems or phenyl groups are optionally substituted with one or more substituents selected from halo, CN, $OR^9$, $N(R^9)_2$, $C(O)OR^9$, $C(O)N(R^9)_2$, $C(O)R^9$, $N(R)C(O)R^9$ and $C_{1-4}$ alkyl optionally substituted with halo, $OR^9$ or $N(R^9)_2$; each $R^9$ is independently selected from H, $C_{1-6}$ alkyl or $C_{1-6}$ haloalkyl;

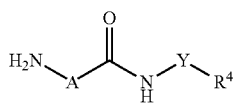

(XVI)

wherein
A is

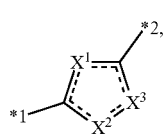

one of $X^1$, $X^2$, $X^3$ is S and the other two of $X^1$, $X^2$ and $X^3$ are CH;

=== represents a single or a double bond such that the ring A is aromatic;

*1 indicates the point of attachment to

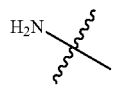

and *2 indicates the point of attachment to

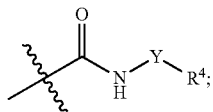

Y is —$CH_2$— or —$CH(CH_3)$—;

$R^4$ is a
- 6- to 14-membered aryl, 5- to 14-membered heteroaryl or a 5- to 10-membered carbocyclic ring system, any of which is optionally substituted with one or more substituents selected from: halo, CN, nitro, $R^{19}$, $OR^{19}$, $OR^6$, $SR^6$, $NR^6R^7$, $C(O)R^6$, $C(O)R^{19}$, $C(O)OR^6$, $C(O)N(R^6)(R^7)$, $N(R)C(O)R^6$;
- $C_{1-6}$ alkyl or $O(C_{1-6}$ alkyl) either of which is optionally substituted with one or more substituents selected from halo, CN, nitro, $R^{19}$, $OR^6$, $SR^6$, $NR^6R^7$, $C(O)R^6C(O)OR^6$, $C(O)N(R^6)(R^7)$ and $N(R^7)C(O)R^6$, and when $R^4$ is not fully aromatic in character, oxo;
- wherein $R^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, $O(C_{1-4}$ alkyl), $O(C_{1-4}$ haloalkyl);
- $R^6$ is H, $C_{1-6}$ alkyl, $C_{1-6}$ haloalkyl, benzyl, 3- to 7-membered carbocyclyl or 3- to 7-membered heterocyclyl;
- $R^7$ is H, $C_{1-6}$ alkyl or $C_{1-6}$ haloalkyl; or
- $R^6$ and $R^7$ together with the nitrogen atom to which they are attached form a 4 to 7-membered heterocyclic ring optionally containing one or more further heteroatoms and optionally substituted with one or more substituents selected from $C_{1-4}$ alkyl, oxo and halo;

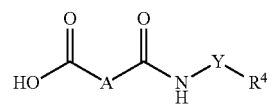

(XX)

wherein
A is

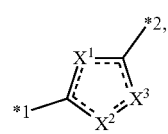

one of $X^1$, $X^2$, $X^3$ is S and the other two of $X^1$, $X^2$ and $X^3$ are CH;

=== represents a single or a double bond such that the ring A is aromatic;

*¹ indicates the point of attachment to

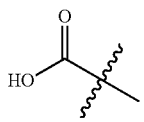

and *² indicates the point of attachment to

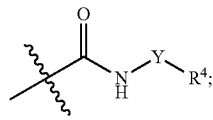

Y is —CH₂— or —CH(CH₃)—;
R⁴ is a
- 6- to 14-membered aryl, 5- to 14-membered heteroaryl or a 5- to 10-membered carbocyclic ring system, any of which is optionally substituted with one or more substituents selected from: halo, CN, nitro, $R^{19}$, $OR^{19}$, $OR^6$, $SR^6$, $NR^6R^7$, $C(O)R^6$, $C(O)R^{19}$, $C(O)OR^6$, $C(O)N(R^6)(R^7)$, $N(R^7)C(O)R^6$;
- $C_{1-6}$ alkyl or $O(C_{1-6}$ alkyl) either of which is optionally substituted with one or more substituents selected from halo, CN, nitro, $R^{19}$, $OR^6$, $SR^6$, $NR^6R^7$, $C(O)R^6C(O)OR^6$, $C(O)N(R^6)(R^7)$ and $N(R^7)C(O)R^6$; and
when R⁴ is not fully aromatic in character, oxo;
  wherein $R^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, $O(C_{1-4}$ alkyl), $O(C_{1-4}$ haloalkyl);
  R⁶ is H, $C_{1-6}$ alkyl, $C_{1-6}$ haloalkyl, benzyl, 3- to 7-membered carbocyclyl or 3- to 7-membered heterocyclyl;
  R⁷ is H, $C_{1-6}$ alkyl or $C_{1-6}$ haloalkyl; or
  R⁶ and R⁷ together with the nitrogen atom to which they are attached form a 4 to 7-membered heterocyclic ring optionally containing one or more further heteroatoms and optionally substituted with one or more substituents selected from $C_{1-4}$ alkyl, oxo and halo;

(XXV)

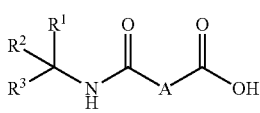

wherein
A is

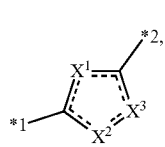

one of $X^1$, $X^2$, $X^3$ is S and the other two of $X^1$, $X^2$ and $X^3$ are CH;
=== represents a single or a double bond such that the ring A is aromatic;
*¹ indicates the point of attachment to

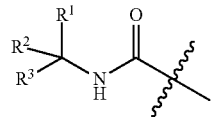

and *² indicates the point of attachment to

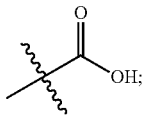 [SMILES: *C(=O)O]

R¹ is H, CN, $C(O)OR^{12}$, $C_{1-3}$ alkyl, $C_{2-3}$ alkenyl or $C_{2-3}$ alkynyl, any of which alkyl, alkenyl or alkynyl groups are optionally substituted with one or more substituents, selected from fluoro, $OR^{12}$, $N(R^{12})_2$, $C(O)OR^{12}$, $C(O)N(R^{12})_2$, $C(O)R^{12}$ and $N(R^{13})C(O)R^{12}$;
R² is H or $C_{1-6}$ alkyl optionally substituted with $OR^{12}$; and
  wherein each $R^{12}$ and $R^{13}$ is independently selected from H, $C_{1-6}$ alkyl and $C_{1-6}$ fluoroalkyl,
R³ is:
  $C_{1-6}$ alkyl, $C_{2-6}$ alkenyl or $C_{2-6}$ alkynyl, any of which $C_{1-6}$ alkyl, $C_{2-6}$ alkenyl or $C_{2-6}$ alkynyl groups are optionally substituted with one or more substituents selected from fluoro, CN, $R^{14}$ $OR^{14}$, $OR^{15}$, $N(R^{15})_2$, $C(O)OR^{15}$, $C(O)N(R^{15})_2$, $N(R^{16})C(O)R^{15}$, $N(R^{15})S(O)_2R^{14}$, $N(R^{15})S(O)_2R^{16}$ and $N(R^{15})C(O)OR^{16}$; or
R³ is:
  a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, $OR^{17}$ and $N(R^{17})_2$;
  wherein $R^{14}$ is a 6- to 10-membered aryl or 5- to 10-membered heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, $OR^{17}$ and $N(R^{17})_2$;
    wherein each $R^{17}$ is independently H, $C_{1-4}$ alkyl or $C_{1-4}$ haloalkyl;
  wherein each $R^{15}$ and $R^{16}$ is independently H, $C_{1-6}$ alkyl or $C_{1-6}$ haloalkyl; or
  R² and R³ together with the carbon atom to which they are attached combine to form a 3- to 10-membered carbocyclic or heterocyclic ring system optionally substituted with one or more substituents selected from halo, CN, $OR^9$, $N(R^9)_2$, $C(O)OR^9$, $C(O)N(R^9)_2$, $C(O)R^9$, $N(R)C(O)R^9$ and $C_{1-4}$ alkyl optionally substituted with halo, $OR^9$ or $N(R^9)_2$; or R¹, R² and R³ together with the carbon atom to which they are attached combine to form a bridged 5- to 10-membered carbocyclic or heterocyclic ring system or phenyl, any of which carbocyclic or heterocyclic ring systems or phenyl groups are optionally substituted with one or more substituents selected from halo, CN, $OR^9$, $N(R^9)_2$, $C(O)OR^9$, $C(O)N(R^9)_2$, $C(O)R^9$, $N(R)C(O)R^9$ and $C_{1-4}$ alkyl optionally substituted with halo, $OR^9$ or $N(R^9)_2$; each $R^9$ is independently selected from H, $C_{1-6}$ alkyl or $C_{1-6}$ haloalkyl;

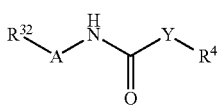
(XXX)

wherein
$R^{32}$ is halo;
A is

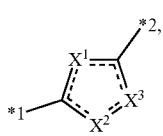

one of $X^1$, $X^2$, $X^3$ is S and the other two of $X^1$, $X^2$ and $X^3$ are CH;
=== represents a single or a double bond such that the ring A is aromatic;
*¹ indicates the point of attachment to $R^{32}$ and *² indicates the point of attachment to

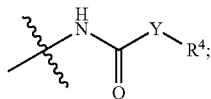

Y is —CH₂— or —CH(CH₃)—;
$R^4$ is a
 6- to 14-membered aryl, 5- to 14-membered heteroaryl or a 5- to 10-membered carbocyclic ring system, any of which is optionally substituted with one or more substituents selected from: halo, CN, nitro, $R^{19}$, $OR^{19}$, $OR^6$, $SR^6$, $NR^6R^7$, $C(O)R^6$, $C(O)R^{19}$, $C(O)OR^6$, $C(O)N(R^6)(R^7)$, $N(R)C(O)R^6$,
 $C_{1-6}$ alkyl or $O(C_{1-6}$ alkyl) either of which is optionally substituted with one or more substituents selected from halo, CN, nitro, $R^{19}$, $OR^6$, $SR^6$ $NR^6R^7$, $C(O)R^6 C(O)OR^6$, $C(O)N(R^6)(R^7)$ and $N(R^7)C(O)R^6$; and
when $R^4$ is not fully aromatic in character, oxo;
 wherein $R^{19}$ is a 5- or 6-membered aryl or heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, OH, $O(C_{1-4}$ alkyl), $O(C_{1-4}$ haloalkyl);

$R^6$ is H, $C_{1-6}$ alkyl, $C_{1-6}$ haloalkyl, benzyl, 3- to 7-membered carbocyclyl or 3- to 7-membered heterocyclyl;
$R^7$ is H, $C_{1-6}$ alkyl or $C_{1-6}$ haloalkyl; or
$R^6$ and $R^7$ together with the nitrogen atom to which they are attached form a 4 to 7-membered heterocyclic ring optionally containing one or more further heteroatoms and optionally substituted with one or more substituents selected from $C_{1-4}$ alkyl, oxo and halo;

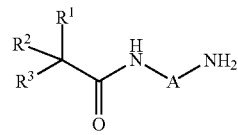
(XXXV)

wherein
A is

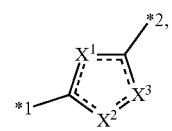

one of $X^1$, $X^2$, $X^3$ is S and the other two of $X^1$, $X^2$ and $X^3$ are CH;
=== represents a single or a double bond such that the ring A is aromatic;
*¹ indicates the point of attachment to

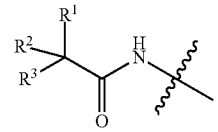

and *² indicates the point of attachment to

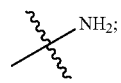

$R^1$ is H, CN, $C(O)OR^{12}$, $C_{1-3}$ alkyl, $C_{2-3}$ alkenyl or $C_{2-3}$ alkynyl, any of which alkyl, alkenyl or alkynyl groups are optionally substituted with one or more substituents, selected from fluoro, $OR^{12}$, $N(R^{12})_2$, $C(O)OR^{12}$, $C(O)N(R^{12})_2$, $C(O)R^{12}$ and $N(R^{13})C(O)R^{12}$;
$R^2$ is H or $C_{1-6}$ alkyl optionally substituted with $OR^{12}$; and
 wherein each $R^{12}$ and $R^{13}$ is independently selected from H, $C_{1-6}$ alkyl and $C_{1-6}$ fluoroalkyl,
$R^3$ is:
 $C_{1-6}$ alkyl, $C_{2-6}$ alkenyl or $C_{2-6}$ alkynyl, any of which $C_{1-6}$ alkyl, $C_{2-6}$ alkenyl or $C_{2-6}$ alkynyl groups are optionally substituted with one or more substituents selected from fluoro, CN, $R^{14}$ $OR^{14}$, $OR^{15}$, $N(R^{15})_2$, $C(O)OR^{15}$, $C(O)N(R^{15})_2$, $N(R^{16})C(O)R^{15}$, $N(R^{15})S(O)_2R^{14}$, $N(R^{15})S(O)_2R^{16}$ and $N(R^{15})C(O)OR^{16}$; or $R^3$ is:
- a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, $OR^{17}$ and $N(R^{17})_2$;

wherein $R^{14}$ is a 6- to 10-membered aryl or 5- to 10-membered heteroaryl ring system or a 3- to 7-membered carbocyclic or heterocyclic ring system, any of which aryl, heteroaryl, carbocyclic or heterocyclic ring systems are optionally substituted with one or more substituents selected from halo, $C_{1-4}$ alkyl, $C_{1-4}$ haloalkyl, $OR^{17}$ and $N(R^{17})_2$; wherein each $R^{17}$ is independently H, $C_{1-4}$ alkyl or $C_{1-4}$ haloalkyl;

wherein each $R^{15}$ and $R^{16}$ is independently H, $C_{1-6}$ alkyl or $C_{1-6}$ haloalkyl; or $R^2$ and $R^3$ together with the carbon atom to which they are attached combine to form a 3- to 10-membered carbocyclic or heterocyclic ring system optionally substituted with one or more substituents selected from halo, CN, $OR^9$, $N(R^9)_2$, $C(O)OR^9$, $C(O)N(R^9)_2$, $C(O)R^9$, $N(R^9)C(O)R^9$ and $C_{1-4}$ alkyl optionally substituted with halo, $OR^9$ or $N(R^9)_2$; or $R^1$, $R^2$ and $R^3$ together with the carbon atom to which they are attached combine to form a bridged 5- to 10-membered carbocyclic or heterocyclic ring system or phenyl, any of which carbocyclic or heterocyclic ring systems or phenyl groups are optionally substituted with one or more substituents selected from halo, CN, $OR^9$, $N(R^9)_2$, $C(O)OR^9$, $C(O)N(R^9)_2$, $C(O)R^9$, $N(R)C(O)R^9$ and $C_{1-4}$ alkyl optionally substituted with halo, $OR^9$ or $N(R^9)_2$; each $R^9$ is independently selected from H, $C_{1-6}$ alkyl or $C_{1-6}$ haloalkyl.

\* \* \* \* \*